US012780913B2

(12) United States Patent
Xiao et al.

(10) Patent No.: US 12,780,913 B2
(45) Date of Patent: Nov. 3, 2026

(54) ANTI-CD47/ANTI-PD-L1 ANTIBODY AND APPLICATIONS THEREOF

(71) Applicant: NANJING SANHOME PHARMACEUTICAL CO., LTD., Nanjing (CN)

(72) Inventors: Yang Xiao, Nanjing (CN); Yongqiang Zhu, Nanjing (CN); Liwen Zhao, Nanjing (CN); Wenming Wu, Nanjing (CN); Guo Zhou, Nanjing (CN); Cheng Luo, Nanjing (CN); Xue Li, Nanjing (CN)

(73) Assignee: NANJING SANHOME PHARMACEUTICAL CO., LTD., Nanjing (CN)

(*) Notice: Subject to any disclaimer, the term of this patent is extended or adjusted under 35 U.S.C. 154(b) by 1102 days.

(21) Appl. No.: 17/802,904

(22) PCT Filed: Feb. 26, 2021

(86) PCT No.: PCT/CN2021/078132
§ 371 (c)(1),
(2) Date: Aug. 26, 2022

(87) PCT Pub. No.: WO2021/170082
PCT Pub. Date: Sep. 2, 2021

(65) Prior Publication Data

US 2023/0090014 A1 Mar. 23, 2023

(30) Foreign Application Priority Data

Feb. 28, 2020 (CN) ........................ 202010128900.X

(51) Int. Cl.

| | |
|---|---|
| ***C07K 16/28*** | (2006.01) |
| ***A61P 35/00*** | (2006.01) |
| *A61K 39/00* | (2006.01) |

(52) U.S. Cl.
CPC .......... *C07K 16/2803* (2013.01); *A61P 35/00* (2018.01); *C07K 16/2827* (2013.01); *A61K 2039/505* (2013.01); *C07K 2317/24* (2013.01); *C07K 2317/31* (2013.01); *C07K 2317/76* (2013.01); *C07K 2317/92* (2013.01)

(58) Field of Classification Search
CPC ............ C07K 16/2803; C07K 16/2827; C07K 2317/24; C07K 2317/31; C07K 2317/76; C07K 2317/92; A61P 35/00; A61K 2039/505
See application file for complete search history.

(56) References Cited

U.S. PATENT DOCUMENTS

| | | | | |
|---|---|---|---|---|
| 2020/0157223 A1 | 5/2020 | Song et al. | | |
| 2021/0230277 A1* | 7/2021 | Liu | ......................... | A61P 35/00 |
| 2022/0119520 A1* | 4/2022 | Wang | ................. | C07K 16/2803 |

FOREIGN PATENT DOCUMENTS

| | | | | | |
|---|---|---|---|---|---|
| CA | 3084626 | A1 | | 6/2019 | |
| CA | 3081117 | A1 | | 7/2019 | |
| CN | 107459578 | A | | 12/2017 | |
| CN | 107973854 | A | * | 5/2018 | ......... C07K 16/2827 |
| CN | 108864290 | A | | 11/2018 | |
| WO | WO2019079549 | A1 | | 4/2019 | |
| WO | WO2020043188 | A1 | * | 8/2019 | ......... C07K 16/2803 |

OTHER PUBLICATIONS

International Search Report issued in International Application No. PCT/CN2021/078132, mailed Jun. 1, 2021.
Brown, M. et al., "Tolerance to Single, but Not Multiple, Amino Acid Replacements in Antibody $V_H$ CDR2: A Means of Minimizing 8 Cell Wastage from Somatic Hypermutation?" *The Journal of Immunology*, 156 (1996): 3285-3291.
Extended European Search Report issued in European Patent Application No. 21760510.4, dated Feb. 23, 2024.
Liu, B. et al., "Elimination of tumor by CD47 /PD-L 1 dual-targeting fusion protein that engages innate and adaptive immune responses," *MABS*, 10.2 (2018): 315-324.
Winkler, K. et al., "Changing the Antigen Binding Specificity by Single Point Mutations of an Anti-p24 (HIV-1) Antibody," *The Journal of Immunology*, 165 (2000): 4505-4514.
Zhang, X. et al., "Insights into CD47/SIRPa axis-targeting tumor immunotherapy," *Antibody Therapeutics*, 1.2 (2018): 27-32.

* cited by examiner

*Primary Examiner* — Peter J Reddig
*Assistant Examiner* — Estella M. Gustilo
(74) *Attorney, Agent, or Firm* — pH IP Law

(57) ABSTRACT

Provided are an anti-CD47/anti-PD-L1 antibody, a pharmaceutical composition of the anti-CD47/anti-PD-L1 antibody, and applications thereof. The anti-CD47/anti-PD-L1 antibody provides antitumor activity, is free of significant red blood cell toxicity, and is applicable in preparing an antitumor medicament.

17 Claims, 13 Drawing Sheets

Specification includes a Sequence Listing.

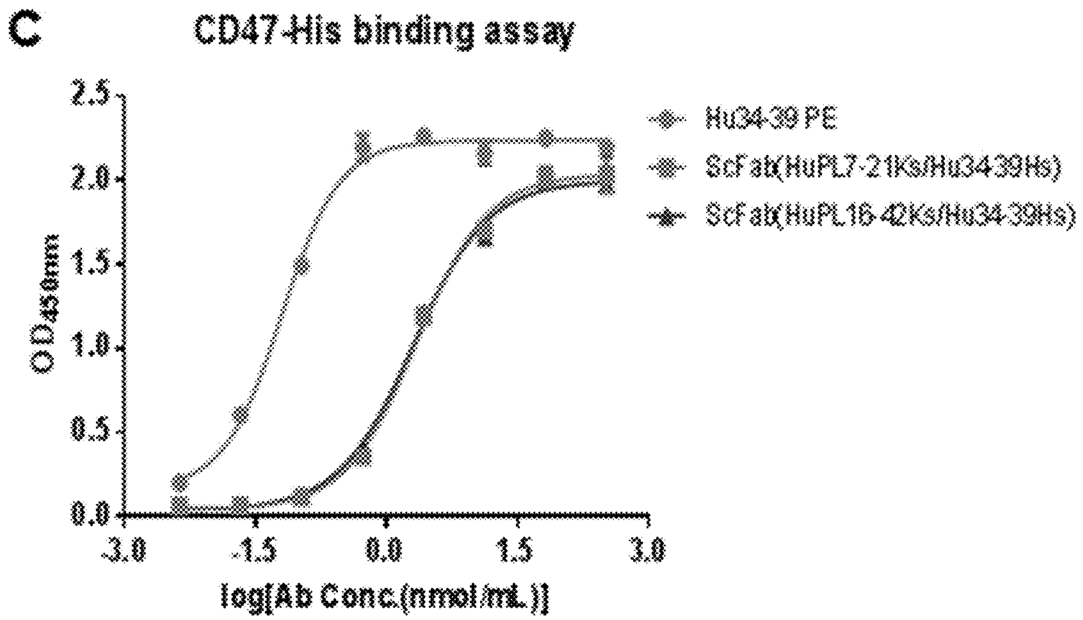
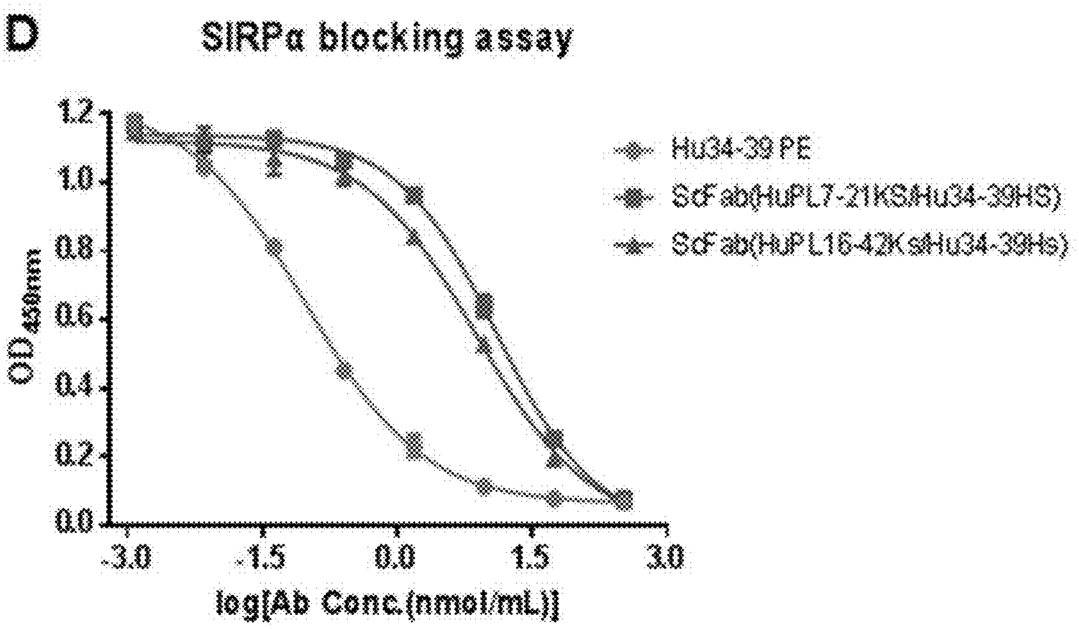
FIG. 11-cont.

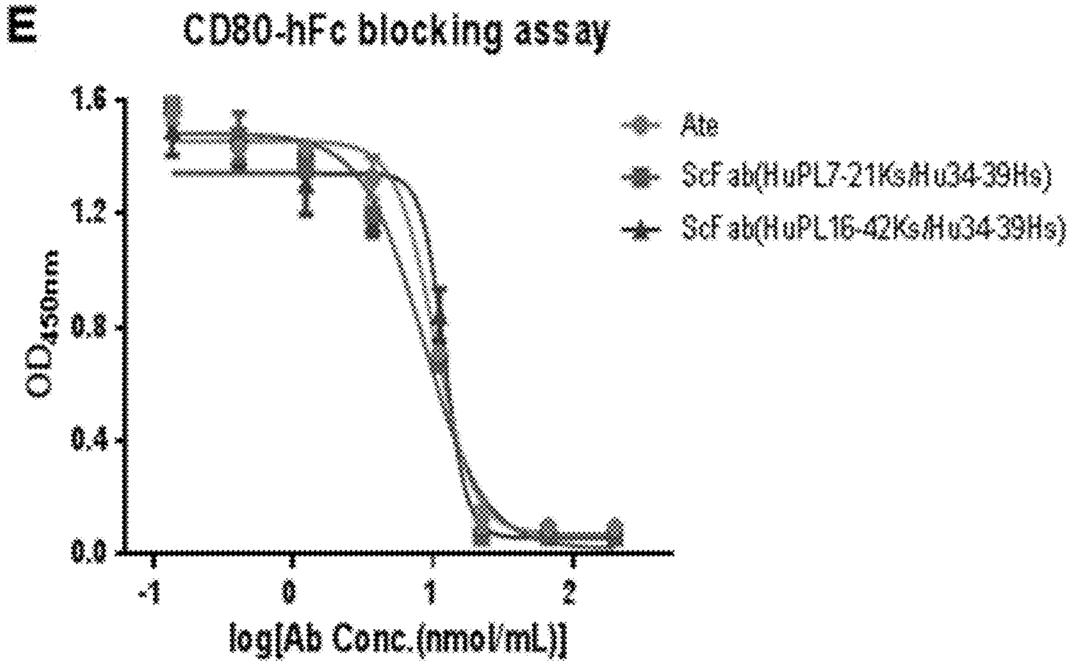
FIG. 11-cont.

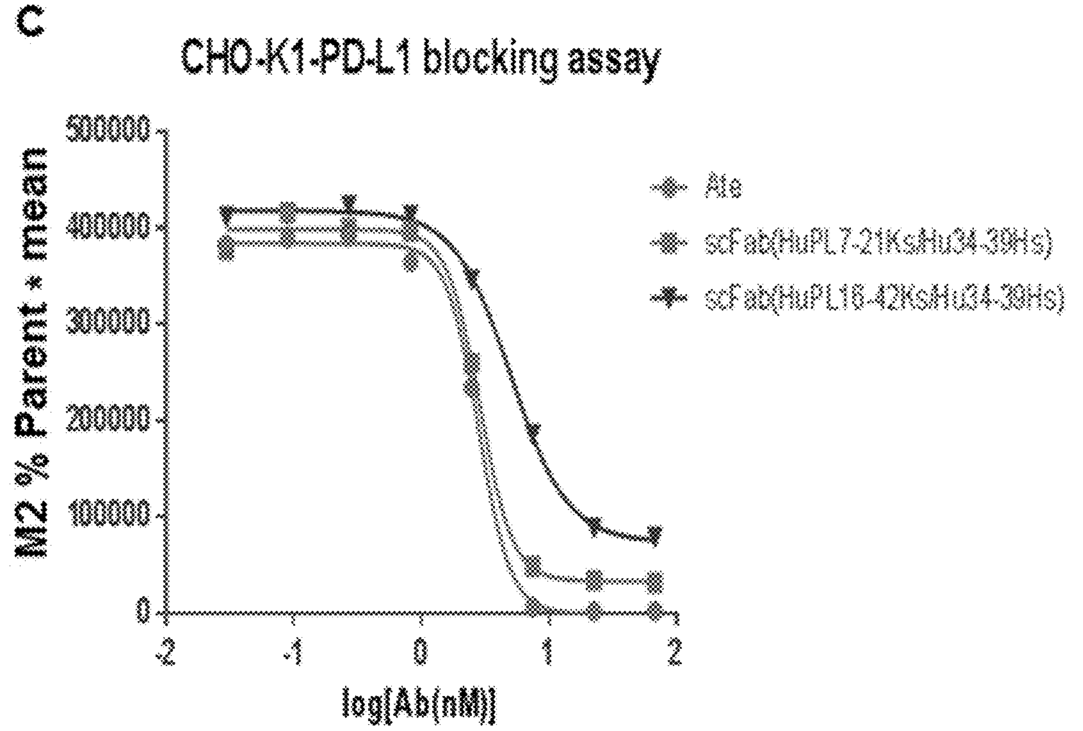
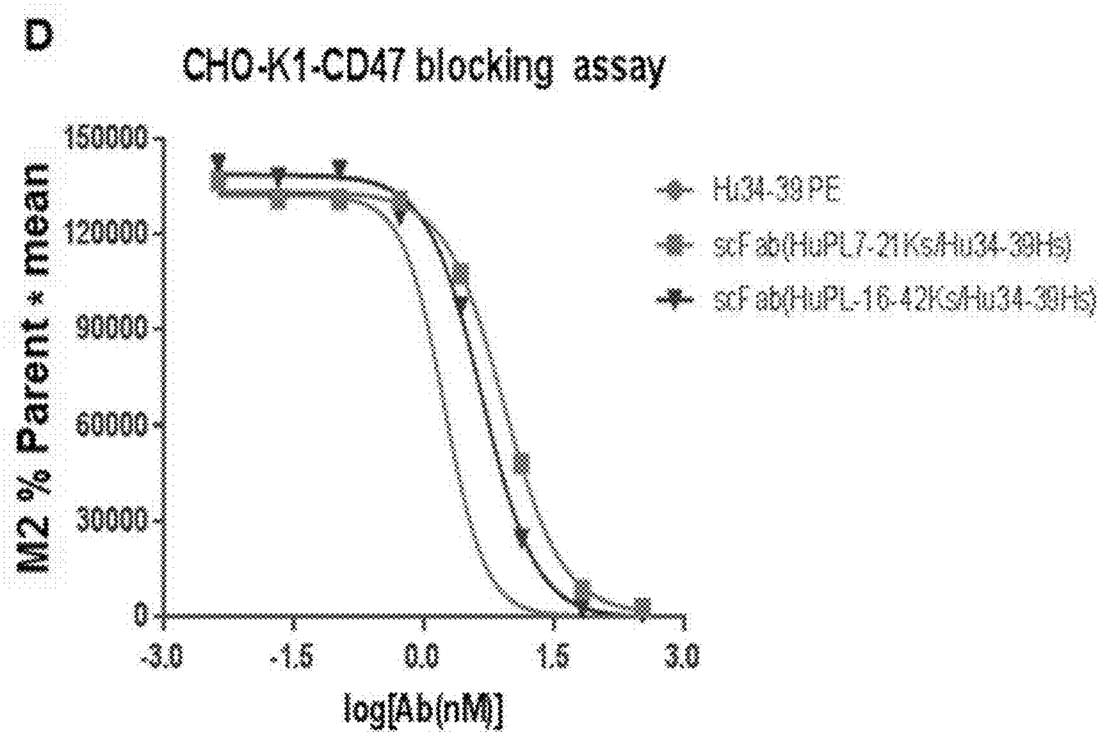
FIG. 12-cont.

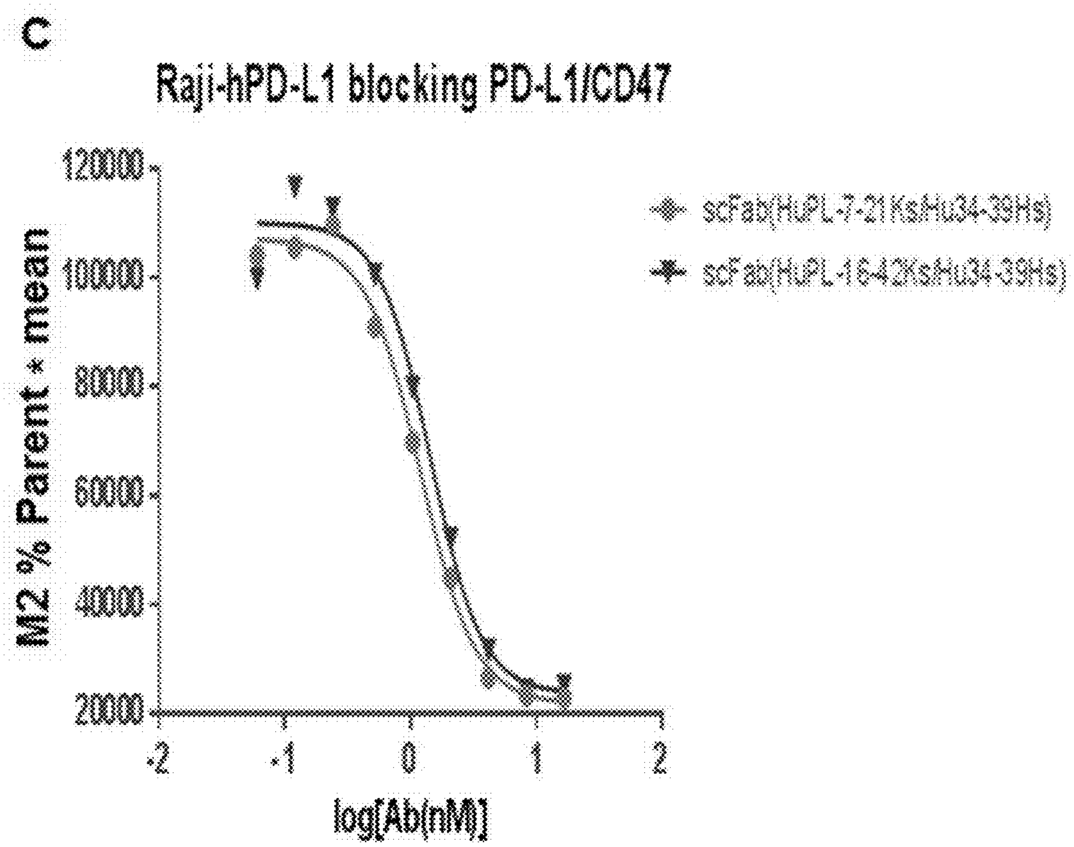
FIG. 13-cont.

ANTI-CD47/ANTI-PD-L1 ANTIBODY AND APPLICATIONS THEREOF

CROSS-REFERENCE TO RELATED APPLICATIONS

This application is a national phase application under 35 U.S.C. § 371 of International Application No. PCT/CN2021/078132 filed on Feb. 26, 2021, which claims the priority of Chinese Patent Application No. 202010128900.X filed on Feb. 28, 2020, and the disclosures of each of which are hereby incorporated by reference in its entirety.

REFERENCE TO A SEQUENCE LISTING

Pursuant to 37 C.F.R. 1.821(c), a sequence listing is submitted herewith as an ASCII compliant text file named "UNIT.P0085US_ST25.txt", created on Aug. 26, 2022, and having a size of 118,504 bytes. The content of the aforementioned file is hereby incorporated by reference in its entirety.

FIELD

The present disclosure relates to the technical field of antibody drugs, and in particular, to an anti-CD47/anti-PD-L1 antibody, a pharmaceutical composition comprising the anti-CD47/anti-PD-L1 antibodies, and uses thereof.

BACKGROUND

CD47 protein, also known as integrin-associated protein (IAP), is a five-span transmembrane glycoprotein belonging to the IgG superfamily and widely expressed in different tissues and cells. CD47 can bind to the ligand TSP-1 or SIRPα to regulate different cellular functions, including migration, adhesion and apoptosis of cells, axon extension, cytokine production as well as T cell activation. SIRPα is a transmembrane protein containing a typical immunoreceptor tyrosine-based inhibitory motif (ITIM), and mainly expressed on the surface of the cell membrane of myeloid hematopoietic cells, such as macrophages, dendritic cells, etc. The binding of CD47 to SIRPα leads to phosphorylation of ITIMs and consequent recruitment of SHP-1/SHP-2, which further inhibit the accumulation of myosin IIA in phagocytic synapses, and ultimately inhibit the phagocytic function of phagocytes.

The "immune escape" of tumor cells is considered as the main mechanism of tumorigenesis, tumor development and drug resistance. Through high expression of CD47 molecules, which interact with SIRPα on the surface of macrophages, tumor cells can significantly inhibit the phagocytic activity of macrophages and avoid being swallowed by macrophages. When the binding of CD47 to SIRPα is blocked, the immune suppression or immune tolerance caused by tumor can be eliminated, and tumor cells can be effectively killed. This provides a very powerful theoretical basis for targeting CD47 as a target of targeted tumor immunotherapy.

In recent years, numerous studies have been conducted on various treatments targeting CD47/SIRPα signaling pathway at home and abroad. Among them, antibodies blocking CD47 are believed to be the most promising tumor treatment regimen. The effectiveness of monoclonal antibodies blocking human CD47 have been confirmed in diverse preclinical models. However, since red blood cells and platelets also express CD47 molecules, when the antibodies block the interaction between CD47 and SIRPα, it is likely that these cells may lose the protection of "don't eat me" signal and thereby be subjected to phagocytosis by macrophages. Therefore, the side effects of anti-CD47 antibody, such as degradation of platelets, agglutination of red blood cells, depletion of red blood cells, and anemia, etc. should be considered and avoided when applying anti-CD47 antibody.

Programmed death ligand 1 (PD-L1), also known as cluster of differentiation 274 (CD274) or B7 homolog 1 (B7-H1), is a 40 kDa type I transmembrane protein that plays a major role in suppressing the immune system during specific events such as pregnancy, tissue allotransplantation, autoimmune diseases and other disease states such as hepatitis. Binding of PD-L1 to PD-1 or B7.1 transmits an inhibitory signal that reduces the proliferation of $CD8^+$ T cells in lymph nodes, and supplementation of PD-1 is also able to control the accumulation of T cells specific for foreign antigens in lymph nodes through apoptosis mediated by the gene Bcl-2.

The up-regulation of PD-L1 has been shown to allow cancers to evade the host immune system. Analysis of tumor samples from patients with renal cell carcinoma reveals that high PD-L1 expression in tumors was associated with increased tumor aggressiveness and increased risk of death. Many PD-L1 inhibitors are in development as immuno-oncology therapies and are showing promising results in clinical trials.

The CD47-SIRPα signaling pathway not only activates innate immunity, but further kills tumors in the way that macrophages present tumor antigens to CD8+T and CD4+ T cells to promote T cell activation. Therefore, it is possible to develop a bifunctional fusion protein targeting CD47 and PD-L1 comprising a CD47-binding portion and a PD-L1-binding portion, which can block not only the binding of PD-L1 to PD-1 but also the binding of CD47 to SIRPα, and thus bridge the innate and adaptive immune signaling pathways, resulting in better antitumor activity, tumor targeting and lower toxicity on red blood cells.

SUMMARY

The present disclosure provides an anti-CD47/anti-PD-L1 antibody comprising an anti-CD47 antibody or antigen-binding fragment thereof and an anti-PD-L1 antibody or antigen-binding fragment thereof, wherein the anti-CD47 antibody or antigen-binding fragment thereof comprises a first heavy chain variable region and/or a first light chain variable region, wherein the first heavy chain variable region comprises a complementarity determining region 1 of the first heavy chain variable region (H1CDR1), a complementarity determining region 2 of the first heavy chain variable region (H1CDR2) and/or a complementarity determining region 3 of the first heavy chain variable region (H1CDR3); and the first light chain variable region comprises a complementarity determining region 1 of the first light chain variable region (L1CDR1), a complementarity determining region 2 of the first light chain variable region (L1CDR2) and/or a complementarity determining region 3 of the first light chain variable region (L1CDR3); and the anti-PD-L1 antibody or antigen-binding fragment thereof is an antibody or antigen-binding fragment thereof that specifically binds to PD-L1.

In some embodiments, the present disclosure provides an anti-CD47/anti-PD-L1 antibody comprising an anti-CD47 antibody or antigen-binding fragment thereof and an anti-PD-L1 antibody or antigen-binding fragment thereof, wherein the anti-CD47 antibody or antigen-binding fragment thereof comprises a first heavy chain variable region and a first light chain variable region, wherein:

(1) the first heavy chain variable region comprises H1CDR1, H1CDR2 and H1CDR3 selected from the group consisting of:

(a1) amino acid sequences set forth in SEQ ID NOs: 1, 2 and 3;

(a2) amino acid sequences set forth in SEQ ID NOs: 10, 2 and 11;

(a3) amino acid sequences set forth in SEQ ID NOs: 4, 5 and 6;

(a4) amino acid sequences set forth in SEQ ID NOs: 7, 8 and 9; and (a5) amino acid sequences having at least 85% sequence identity to the amino acid sequences set forth in (a1), (a2), (a3) or (a4); and (2) the first light chain variable region comprises L1CDR1, L1CDR2 and L1CDR3 selected from the group consisting of:

(a6) amino acid sequences set forth in SEQ ID NOs: 12, 13 and 14;

(a7) amino acid sequences set forth in SEQ ID NOs: 15, 16 and 17;

(a8) amino acid sequences set forth in SEQ ID NOs: 18, 19 and 20;

(a9) amino acid sequences having at least 85% sequence identity to the amino acid sequences set forth in (a6), (a7) or (a8).

In some embodiments, the anti-CD47 antibody or antigen-binding fragment thereof of the anti-CD47/anti-PD-L1 antibody comprises:

the first heavy chain variable region comprising H1CDR1, H1CDR2 and H1CDR3 with amino acid sequences set forth in SEQ ID NOs: 1, 2 and 3, or with amino acid sequences having at least 85% sequence identity to the amino acid sequences set forth in SEQ ID NOs: 1, 2 and 3, respectively, and the first light chain variable region comprising L1CDR1, L1CDR2 and L1CDR3 with amino acid sequences set forth in SEQ ID NOs: 12, 13 and 14, or with amino acid sequences having at least 85% sequence identity to the amino acid sequences set forth in SEQ ID NOs: 12, 13 and 14, respectively;

the first heavy chain variable region comprising H1CDR1, H1CDR2 and H1CDR3 with amino acid sequences set forth in SEQ ID NOs: 10, 2 and 11, or with amino acid sequences having at least 85% sequence identity to the amino acid sequences set forth in SEQ ID NOs: 10, 2 and 11, respectively, and the first light chain variable region comprising L1CDR1, L1CDR2 and L1CDR3 with amino acid sequences set forth in SEQ ID NOs: 12, 13 and 14, or with amino acid sequences having at least 85% sequence identity to the amino acid sequences set forth in SEQ ID NOs: 12, 13 and 14, respectively;

the first heavy chain variable region comprising H1CDR1, H1CDR2 and H1CDR3 with amino acid sequences set forth in SEQ ID NOs: 4, 5 and 6, or with amino acid sequences having at least 85% sequence identity to the amino acid sequences set forth in SEQ ID NOs: 4, 5 and 6, respectively, and the first light chain variable region comprising L1CDR1, L1CDR2 and L1CDR3 with amino acid sequences set forth in SEQ ID NOs: 15, 16 and 17, or with amino acid sequences having at least 85% sequence identity to the amino acid sequences set forth in SEQ ID NOs: 15, 16 and 17, respectively; or the first heavy chain variable region comprising H1CDR1, H1CDR2 and H1CDR3 with amino acid sequences set forth in SEQ ID NOs: 7, 8 and 9, or with amino acid sequences having at least 85% sequence identity to the amino acid sequences set forth in SEQ ID NOs: 7, 8 and 9, respectively, and the first light chain variable region comprising L1CDR1, L1CDR2 and L1CDR3 with amino acid sequences set forth in SEQ ID NOs: 18, 19 and 20, or with amino acid sequences having at least 85% sequence identity to the amino acid sequences set forth in SEQ ID NOs: 18, 19 and 20, respectively.

In some embodiments, the anti-CD47 antibody or antigen-binding fragment thereof of the anti-CD47/anti-PD-L1 antibody comprises a first heavy chain variable region and a first light chain variable region, wherein:

(1) the first heavy chain variable region comprises an amino acid sequence selected from the group consisting of:

(b1) amino acid sequences set forth in SEQ ID NOs: 21, 22, 23 and 27, (b2) amino acid sequences derived from the amino acid sequences set forth in (b1) by substitution, deletion or addition of one or more amino acids and functionally identical or similar to the amino acid sequences set forth in (b1), and (b3) amino acid sequences having at least 80% sequence identity to the amino acid sequences set forth in (b1); and (2) the first light chain variable region comprises an amino acid sequence selected from the group consisting of:

(b4) amino acid sequences set forth in SEQ ID NOs: 24, 25, 26 and 28, (b5) amino acid sequences derived from the amino acid sequences set forth in (b4) by substitution, deletion or addition of one or more amino acids and functionally identical or similar to the amino acid sequences set forth in (b4), and (b6) amino acid sequences having at least 80% sequence identity to the amino acid sequences set forth in (b4).

In some embodiments, the anti-CD47 antibody or antigen-binding fragment thereof of the anti-CD47/anti-PD-L1 antibody comprises a first heavy chain variable region and a first light chain variable region, wherein:

the first heavy chain variable region comprises an amino acid sequence selected from the group consisting of: an amino acid sequence set forth in SEQ ID NO: 21, amino acid sequences derived from SEQ ID NO: 21 by substitution, deletion or addition of one or more amino acids and functionally identical to SEQ ID NO: 21, and amino acid sequences having at least 85% sequence identity to SEQ ID NO: 21; and the first light chain variable region comprises an amino acid sequence selected from the group consisting of: an amino acid sequence set forth in SEQ ID NO: 24, amino acid sequences derived from SEQ ID NO: 24 by substitution, deletion or addition of one or more amino acids and functionally identical to SEQ ID NO: 24, and amino acid sequences having at least 85% sequence identity to SEQ ID NO: 24;

the first heavy chain variable region comprises an amino acid sequence selected from the group consisting of: an amino acid sequence set forth in SEQ ID NO: 22, amino acid sequences derived from SEQ ID NO: 22 by substitution, deletion or addition of one or more amino acids and functionally identical to SEQ ID NO: 22, and amino acid sequences having at least 85% sequence identity to SEQ ID NO: 22; and the first light chain variable region comprises an amino acid sequence selected from the group consisting of: an amino acid sequence set forth in SEQ ID NO: 25, amino acid sequences derived from SEQ ID NO: 25 by substitution, deletion or addition of one or more amino acids and functionally identical to SEQ ID NO: 25, and amino acid sequences having at least 85% sequence identity to SEQ ID NO: 25;

the first heavy chain variable region comprises an amino acid sequence selected from the group consisting of: an amino acid sequence set forth in SEQ ID NO: 23, amino acid sequences derived from SEQ ID NO: 23 by substitution, deletion or addition of one or more amino acids and functionally identical to SEQ ID NO: 23, and amino acid sequences having at least 85% sequence identity to SEQ ID NO: 23; and the first light chain variable region comprises an amino acid sequence selected from the group consisting of: an amino acid sequence set forth in SEQ ID NO: 26, amino acid sequences derived from SEQ ID NO: 26 by substitution, deletion or addition of one or more amino acids and functionally identical to SEQ ID NO: 26, and amino acid sequences having at least 85% sequence identity to SEQ ID NO: 26;

the first heavy chain variable region comprises an amino acid sequence selected from the group consisting of: an amino acid sequence set forth in SEQ ID NO: 27, amino acid sequences derived from SEQ ID NO: 27 by substitution, deletion or addition of one or more amino acids and functionally identical to SEQ ID NO: 27, and amino acid sequences having at least 85% sequence identity to SEQ ID NO: 27; and the first light chain variable region comprises an amino acid sequence selected from the group consisting of: an amino acid sequence set forth in SEQ ID NO: 24, amino acid sequences derived from SEQ ID NO: 24 by substitution, deletion or addition of one or more amino acids and functionally identical to SEQ ID NO: 24, and amino acid sequences having at least 85% sequence identity to SEQ ID NO: 24; or the first heavy chain variable region comprises an amino acid sequence selected from the group consisting of: an amino acid sequence set forth in SEQ ID NO: 23, amino acid sequences derived from SEQ ID NO: 23 by substitution, deletion or addition of one or more amino acids and functionally identical to SEQ ID NO: 23, and amino acid sequences having at least 85% sequence identity to SEQ ID NO: 23; and the first light chain variable region comprises an amino acid sequence selected from the group consisting of: an amino acid sequence set forth in SEQ ID NO: 28, amino acid sequences derived from SEQ ID NO: 28 by substitution, deletion or addition of one or more amino acids and functionally identical to SEQ ID NO: 28, and amino acid sequences having at least 85% sequence identity to SEQ ID NO: 28.

In some embodiments, the anti-CD47 antibody or antigen-binding fragment thereof of the anti-CD47/anti-PD-L1 antibody is a humanized antibody or antigen-binding fragment thereof comprising a first heavy chain variable region and a first light chain variable region, wherein:

(1) the first heavy chain variable region comprises an amino acid sequence selected from the group consisting of:

(c1) amino acid sequences set forth in SEQ ID NOs: 29, 30 and 31, (c2) amino acid sequences derived from the amino acid sequences set forth in (c1) by substitution, deletion or addition of one or more amino acids and functionally identical or similar to the amino acid sequences set forth in (c1), and (c3) amino acid sequences having at least 80% sequence identity to the amino acid sequences set forth in (c1); and (2) the first light chain variable region comprises an amino acid sequence selected from the group consisting of:

(c4) amino acid sequences set forth in SEQ ID NOs: 32, 33 and 34, (c5) amino acid sequences derived from the amino acid sequences set forth in (c4) by substitution, deletion or addition of one or more amino acids and functionally identical or similar to the amino acid sequences set forth in (c4), and (c6) amino acid sequences having at least 80% sequence identity to the amino acid sequences set forth in (c4).

In some embodiments, the anti-CD47 antibody or antigen-binding fragment thereof of the anti-CD47/anti-PD-L1 antibody is a humanized antibody or antigen-binding fragment thereof comprising a first heavy chain variable region and a first light chain variable region, wherein:

the first heavy chain variable region comprises an amino acid sequence selected from the group consisting of: an amino acid sequence set forth in SEQ ID NO: 29, amino acid sequences derived from SEQ ID NO: 29 by substitution, deletion or addition of one or more amino acids and functionally identical to SEQ ID NO: 29, and amino acid sequences having at least 85% sequence identity to SEQ ID NO: 29; and the first light chain variable region comprises an amino acid sequence selected from the group consisting of: an amino acid sequence set forth in SEQ ID NO: 32, amino acid sequences derived from SEQ ID NO: 32 by substitution, deletion or addition of one or more amino acids and functionally identical to SEQ ID NO: 32, and amino acid sequences having at least 85% sequence identity to SEQ ID NO: 32;

the first heavy chain variable region comprises an amino acid sequence selected from the group consisting of: an amino acid sequence set forth in SEQ ID NO: 30, amino acid sequences derived from SEQ ID NO: 30 by substitution, deletion or addition of one or more amino acids and functionally identical to SEQ ID NO: 30, and amino acid sequences having at least 85% sequence identity to SEQ ID NO: 30; and the first light chain variable region comprises an amino acid sequence selected from the group consisting of: an amino acid sequence set forth in SEQ ID NO: 33, amino acid sequences derived from SEQ ID NO: 33 by substitution, deletion or addition of one or more amino acids and functionally identical to SEQ ID NO: 33, and amino acid sequences having at least 85% sequence identity to SEQ ID NO: 33; or the first heavy chain variable region comprises an amino acid sequence selected from the group consisting of: an amino acid sequence set forth in SEQ ID NO: 31, amino acid sequences derived from SEQ ID NO: 31 by substitution, deletion or addition of one or more amino acids and functionally identical to SEQ ID NO: 31, and amino acid sequences having at least 85% sequence identity to SEQ ID NO: 31; and the first light chain variable region comprises an amino acid sequence selected from the group consisting of: an amino acid sequence set forth in SEQ ID NO: 34, amino acid sequences derived from SEQ ID NO: 34 by substitution, deletion or addition of one or more amino acids and functionally identical to SEQ ID NO: 34, and amino acid sequences having at least 85% sequence identity to SEQ ID NO: 34.

In some embodiments, the present disclosure provides an anti-CD47/anti-PD-L1 antibody comprising an anti-CD47 antibody or antigen-binding fragment thereof and an anti-PD-L1 antibody or antigen-binding fragment thereof, wherein:

the anti-CD47 antibody or antigen-binding fragment thereof comprises a first heavy chain variable region and a first light chain variable region, wherein:

(1) the first heavy chain variable region comprises H1CDR1, H1CDR2 and H1CDR3 with amino acid sequences set forth in SEQ ID NOs: 4, 5 and 6, or with amino acid sequences having at least 85% sequence identity to the amino acid sequences set forth in SEQ ID NOs: 4, 5 and 6, respectively; and (2) the first light chain variable region comprises L1CDR1, L1CDR2 and L1CDR3 with amino acid sequences set forth in SEQ ID NOs: 15, 16 and 17, or with amino acid sequences having at least 85% sequence identity to the amino acid sequences set forth in SEQ ID NOs: 15, 16 and 17, respectively.

In some preferred embodiments, the present disclosure provides an anti-CD47/anti-PD-L1 antibody comprising an anti-CD47 antibody or antigen-binding fragment thereof and an anti-PD-L1 antibody or antigen-binding fragment thereof, wherein the anti-PD-L1 antibody or antigen-binding fragment thereof comprises a second heavy chain variable region and/or a second light chain variable region, wherein the second heavy chain variable region comprises a complementarity determining region 1 of the second heavy chain variable region (H2CDR1), a complementarity determining region 2 of the second heavy chain variable region (H2CDR2) and/or a complementarity determining region 3 of the second heavy chain variable region (H2CDR3); and the second light chain variable region comprises a complementarity determining region 1 of the second light chain variable region (L2CDR1), a complementarity determining region 2 of the second light chain variable region (L2CDR2) and/or a complementarity determining region 3 of the second light chain variable region (L2CDR3).

Further preferably, in some embodiments, the present disclosure provides an anti-CD47/anti-PD-L1 antibody comprising an anti-CD47 antibody or antigen-binding fragment thereof and an anti-PD-L1 antibody or antigen-binding fragment thereof, wherein the anti-CD47 antibody or antigen-binding fragment thereof is as defined in the above embodiments, and the anti-PD-L1 antibody or antigen-binding fragment thereof comprises a second heavy chain variable region and a second light chain variable region, wherein:

(1) the second heavy chain variable region comprises H2CDR1, H2CDR2 and H2CDR3 selected from the group consisting of:

(A1) amino acid sequences set forth in SEQ ID NOs: 75, 76 and 77;

(A2) amino acid sequences set forth in SEQ ID NOs: 81, 82 and 83;

(A3) amino acid sequences set forth in SEQ ID NOs: 87, 88 and 89;

(A4) amino acid sequences set forth in SEQ ID NOs: 93, 94 and 95; and (A5) amino acid sequences having at least 85% sequence identity to the amino acid sequences set forth in (A1), (A2), (A3) or (A4); and (2) the second light chain variable region comprises L2CDR1, L2CDR2 and L2CDR3 selected from the group consisting of:

(A6) amino acid sequences set forth in SEQ ID NOs: 78, 79 and 80;

(A7) amino acid sequences set forth in SEQ ID NOs: 84, 85 and 86;

(A8) amino acid sequences set forth in SEQ ID NOs: 90, 91 and 92;

(A9) amino acid sequences set forth in SEQ ID NOs: 96, 97 and 98; and (A10) amino acid sequences having at least 85% sequence identity to the amino acid sequences set forth in (A6), (A7), (A8) or (A9).

In some specific embodiments, the present disclosure provides an anti-CD47/anti-PD-L1 antibody comprising an anti-CD47 antibody or antigen-binding fragment thereof and an anti-PD-L1 antibody or antigen-binding fragment thereof, wherein:

the anti-CD47 antibody or antigen-binding fragment thereof comprises a first heavy chain variable region and a first light chain variable region, wherein:

(1) the first heavy chain variable region comprises H1CDR1, H1CDR2 and H1CDR3 comprising amino acid sequences set forth in SEQ ID NOs: 4, 5 and 6, or amino acid sequences having at least 85% sequence identity to the amino acid sequences set forth in SEQ ID NOs: 4, 5 and 6, respectively; and (2) the first light chain variable region comprises L1CDR1, L1CDR2 and L1CDR3 comprising amino acid sequences set forth in SEQ ID NOs: 15, 16 and 17, or amino acid sequences having at least 85% sequence identity to the amino acid sequences set forth in SEQ ID NOs: 15, 16 and 17, respectively; and the anti-PD-L1 antibody or antigen-binding fragment thereof comprises a second heavy chain variable region and a second light chain variable region, wherein:

(1) the second heavy chain variable region comprises H2CDR1, H2CDR2 and H2CDR3 selected from the group consisting of:

(A1) amino acid sequences set forth in SEQ ID NOs: 75, 76 and 77;

(A2) amino acid sequences set forth in SEQ ID NOs: 81, 82 and 83;

(A3) amino acid sequences set forth in SEQ ID NOs: 87, 88 and 89;

(A4) amino acid sequences set forth in SEQ ID NOs: 93, 94 and 95; and (A5) amino acid sequences having at least 85% sequence identity to the amino acid sequences set forth in (A1), (A2), (A3) or (A4); and (2) the second light chain variable region comprises L2CDR1, L2CDR2 and L2CDR3 selected from the group consisting of:

(A6) amino acid sequences set forth in SEQ ID NOs: 78, 79 and 80;

(A7) amino acid sequences set forth in SEQ ID NOs: 84, 85 and 86;

(A8) amino acid sequences set forth in SEQ ID NOs: 90, 91 and 92;

(A9) amino acid sequences set forth in SEQ ID NOs: 96, 97 and 98; and (A10) amino acid sequences having at least 85% sequence identity to the amino acid sequences set forth in (A6), (A7), (A8) or (A9).

In a specific embodiment, the present disclosure provides an anti-CD47/anti-PD-L1 antibody comprising an anti-CD47 antibody or antigen-binding fragment thereof and an anti-PD-L1 antibody or antigen-binding fragment thereof. The first heavy chain variable region of the anti-CD47 antibody or antigen-binding fragment thereof comprises H1CDR1, H1CDR2 and H1CDR3 comprising amino acid sequences set forth in SEQ ID NOs: 4, 5 and 6, or amino acid sequences having at least 85% sequence identity to the amino acid sequences set forth in SEQ ID NOs: 4, 5 and 6, respectively, and the first light chain variable region comprises L1CDR1, L1CDR2 and L1CDR3 comprising amino acid sequences set forth in SEQ ID NOs: 15, 16 and 17, or amino acid sequences having at least 85% sequence identity to the amino acid sequences set forth in SEQ ID NOs: 15, 16 and 17, respectively. The second heavy chain variable region of the anti-PD-L1 antibody or antigen-binding fragment thereof comprises H2CDR1, H2CDR2 and H2CDR3 comprising amino acid sequences set forth in SEQ ID NOs: 75, 76 and 77, or amino acid sequences having at least 85% sequence identity to the amino acid sequences set forth in SEQ ID NOs: 75, 76 and 77, respectively, and the second light chain variable region comprises L2CDR1, L2CDR2 and L2CDR3 comprising amino acid sequences set forth in SEQ ID NOs: 78, 79 and 80, or amino acid sequences having at least 85% sequence identity to the amino acid sequences set forth in SEQ ID NOs: 78, 79 and 80, respectively.

In a specific embodiment, the present disclosure provides an anti-CD47/anti-PD-L1 antibody comprising an anti-CD47 antibody or antigen-binding fragment thereof and an anti-PD-L1 antibody or antigen-binding fragment thereof. The first heavy chain variable region of the anti-CD47 antibody or antigen-binding fragment thereof comprises H1CDR1, H1CDR2 and H1CDR3 comprising amino acid sequences set forth in SEQ ID NOs: 4, 5 and 6, or amino acid sequences having at least 85% sequence identity to the amino acid sequences set forth in SEQ ID NOs: 4, 5 and 6, respectively, and the first light chain variable region comprises L1CDR1, L1CDR2 and L1CDR3 comprising amino acid sequences set forth in SEQ ID NOs: 15, 16 and 17, or amino acid sequences having at least 85% sequence identity to the amino acid sequences set forth in SEQ ID NOs: 15, 16 and 17, respectively. The second heavy chain variable region of the anti-PD-L1 antibody or antigen-binding fragment thereof comprises H2CDR1, H2CDR2 and H2CDR3 comprising amino acid sequences set forth in SEQ ID NOs: 81, 82 and 83, or amino acid sequences having at least 85% sequence identity to the amino acid sequences set forth in SEQ ID NOs: 81, 82 and 83, respectively, and the second light chain variable region comprises L2CDR1, L2CDR2 and L2CDR3 comprising amino acid sequences set forth in SEQ ID NOs: 84, 85 and 86, or amino acid sequences having at least 85% sequence identity to the amino acid sequences set forth in SEQ ID NOs: 84, 85 and 86, respectively.

In a specific embodiment, the present disclosure provides an anti-CD47/anti-PD-L1 antibody comprising an anti-CD47 antibody or antigen-binding fragment thereof and an anti-PD-L1 antibody or antigen-binding fragment thereof. The first heavy chain variable region of the anti-CD47 antibody or antigen-binding fragment thereof comprises H1CDR1, H1CDR2 and H1CDR3 comprising amino acid sequences set forth in SEQ ID NOs: 4, 5 and 6, or amino acid sequences having at least 85% sequence identity to the amino acid sequences set forth in SEQ ID NOs: 4, 5 and 6, respectively, and the first light chain variable region comprises L1CDR1, L1CDR2 and L1CDR3 comprising amino acid sequences set forth in SEQ ID NOs: 15, 16 and 17, or amino acid sequences having at least 85% sequence identity to the amino acid sequences set forth in SEQ ID NOs: 15, 16 and 17, respectively. The second heavy chain variable region of the anti-PD-L1 antibody or antigen-binding fragment thereof comprises H2CDR1, H2CDR2 and H2CDR3 comprising amino acid sequences set forth in SEQ ID NOs: 87, 88 and 89, or amino acid sequences having at least 85% sequence identity to the amino acid sequences set forth in SEQ ID NOs: 87, 88 and 89, respectively, and the second light chain variable region comprises L2CDR1, L2CDR2 and L2CDR3 comprising amino acid sequences set forth in SEQ ID NOs: 90, 91 and 92, or amino acid sequences having at least 85% sequence identity to the amino acid sequences set forth in SEQ ID NOs: 90, 91 and 92, respectively.

In a specific embodiment, the present disclosure provides an anti-CD47/anti-PD-L1 antibody comprising an anti-CD47 antibody or antigen-binding fragment thereof and an anti-PD-L1 antibody or antigen-binding fragment thereof. The first heavy chain variable region of the anti-CD47 antibody or antigen-binding fragment thereof comprises H1CDR1, H1CDR2 and H1CDR3 comprising amino acid sequences set forth in SEQ ID NOs: 4, 5 and 6, or amino acid sequences having at least 85% sequence identity to the amino acid sequences set forth in SEQ ID NOs: 4, 5 and 6, respectively, and the first light chain variable region comprises L1CDR1, L1CDR2 and L1CDR3 comprising amino acid sequences set forth in SEQ ID NOs: 15, 16 and 17, or amino acid sequences having at least 85% sequence identity to the amino acid sequences set forth in SEQ ID NOs: 15, 16 and 17, respectively. The second heavy chain variable region of the anti-PD-L1 antibody or antigen-binding fragment thereof comprises H2CDR1, H2CDR2 and H2CDR3 comprising amino acid sequences set forth in SEQ ID NOs: 93, 94 and 95, or amino acid sequences having at least 85% sequence identity to the amino acid sequences set forth in SEQ ID NOs: 93, 94 and 95, respectively, and the second light chain variable region comprises L2CDR1, L2CDR2 and L2CDR3 comprising amino acid sequences set forth in SEQ ID NOs: 96, 97 and 98, or amino acid sequences having at least 85% sequence identity to the amino acid sequences set forth in SEQ ID NOs: 96, 97 and 98, respectively.

In some specific embodiments, for the anti-CD47/anti-PD-L1 antibody according to the present disclosure, the anti-CD47 antibody or antigen-binding fragment thereof and the anti-PD-L1 antibody or antigen-binding fragment thereof are each independently a murine-derived antibody, a chimeric antibody, a humanized antibody or a fully human antibody.

In some specific embodiments, the present disclosure provides an anti-CD47/anti-PD-L1 antibody, wherein the anti-CD47 antibody or antigen-binding fragment thereof comprises a first heavy chain variable region and a first light chain variable region, wherein:

(1) the first heavy chain variable region comprises an amino acid sequence selected from the group consisting of:

(b1) amino acid sequences set forth in SEQ ID NO: 22 and SEQ ID NO: 30, (b2) amino acid sequences derived from the amino acid sequences set forth in (b1) by substitution, deletion or addition of one or more amino acids and functionally identical or similar to the amino acid sequences set forth in (b1), and (b3) amino acid sequences having at least 80% sequence identity to the amino acid sequences set forth in (b1); and (2) the first light chain variable region comprises an amino acid sequence selected from the group consisting of:

(b4) amino acid sequences set forth in SEQ ID NO: 25 and SEQ ID NO: 33, (b5) amino acid sequences derived from the amino acid sequences set forth in (b4) by substitution, deletion or addition of one or more amino acids and functionally identical or similar to the amino acid sequences set forth in (b4), and (b6) amino acid sequences having at least 80% sequence identity to the amino acid sequences set forth in (b4); and the anti-PD-L1 antibody or antigen-binding fragment thereof comprises a second heavy chain variable region and a second light chain variable region, wherein:

(1) the second heavy chain variable region comprises an amino acid sequence selected from the group consisting of:

(B1) amino acid sequences set forth in SEQ ID NOs: 99, 100, 101, 102, 110, 111, 112, 113, 114, 119, 120, 121, 122 and 123, (B2) amino acid sequences derived from the amino acid sequences set forth in (B1) by substitution, deletion or addition of one or more amino acids and functionally identical or similar to the amino acid sequences set forth in (B1), and (B3) amino acid sequences having at least 80% sequence identity to the amino acid sequences set forth in (B1); and (2) the second light chain variable region comprises an amino acid sequence selected from the group consisting of:

(B4) amino acid sequences set forth in SEQ ID NOs: 103, 104, 105, 106, 115, 116, 117, 118, 124, 125 and 126, (B5) amino acid sequences derived from the amino acid sequences set forth in (B4) by substitution, deletion or addition of one or more amino acids and functionally identical or similar to the amino acid sequences set forth in (B4), and (B6) amino acid sequences having at least 80% sequence identity to the amino acid sequences set forth in (B4).

In some specific embodiments, the present disclosure provides an anti-CD47/anti-PD-L1 antibody, wherein the first heavy chain variable region comprises an amino acid sequence selected from the group consisting of: an amino acid sequence set forth in SEQ ID NO: 22, amino acid sequences derived from SEQ ID NO: 22 by substitution, deletion or addition of one or more amino acids and functionally identical to SEQ ID NO: 22, and amino acid sequences having at least 85% sequence identity to SEQ ID NO: 22; and the first light chain variable region comprises an amino acid sequence selected from the group consisting of: an amino acid sequence set forth in SEQ ID NO: 25, amino acid sequences derived from SEQ ID NO: 25 by substitution, deletion or addition of one or more amino acids and functionally identical to SEQ ID NO: 25, and amino acid sequences having at least 85% sequence identity to SEQ ID NO: 25.

In some specific embodiments, the present disclosure provides an anti-CD47/anti-PD-L1 antibody, wherein the first heavy chain variable region has an amino acid sequence selected from the group consisting of: an amino acid sequence set forth in SEQ ID NO: 22, amino acid sequences derived from SEQ ID NO: 22 by substitution, deletion or addition of one or more amino acids and functionally identical to SEQ ID NO: 22, and amino acid sequences comprising H1CDR1, H1CDR2 and H1CDR3 set forth in SEQ ID NOs: 4, 5 and 6 and having at least 85% sequence identity to SEQ ID NO: 22; and the first light chain variable region comprises an amino acid sequence selected from the group consisting of: an amino acid sequence set forth in SEQ ID NO: 25, amino acid sequences derived from SEQ ID NO: 25 by substitution, deletion or addition of one or more amino acids and functionally identical to SEQ ID NO: 25, and amino acid sequences comprising L1CDR1, L1CDR2 and L1CDR3 set forth in SEQ ID NOs: 15, 16 and 17 and having at least 85% sequence identity to SEQ ID NO: 25.

In some specific embodiments, for the anti-CD47/anti-PD-L1 antibody according to the present disclosure, the anti-CD47 antibody or the anti-PD-L1 antibody may be a murine-derived antibody, which further comprises a heavy chain constant region of murine-derived IgG1, IgG2, IgG3, IgG4, or a variant thereof, and a light chain constant region of murine-derived kappa chain or a variant thereof.

In some preferred embodiments, for the anti-CD47/anti-PD-L1 antibody according to the present disclosure, the murine-derived anti-CD47 antibody further comprises a heavy chain constant region of murine-derived IgG1, IgG2, or a variant thereof, and a light chain constant region of murine-derived kappa chain or a variant thereof.

In some specific embodiments, the present disclosure provides an anti-CD47/anti-PD-L1 antibody, wherein the anti-CD47 antibody or antigen-binding fragment thereof comprises a first heavy chain variable region and a first light chain variable region, wherein:

(1) the first heavy chain variable region comprises an amino acid sequence selected from the group consisting of:

(c1) an amino acid sequence set forth in SEQ ID NO: 30, (c2) amino acid sequences derived from the amino acid sequences set forth in (c1) by substitution, deletion or addition of one or more amino acids and functionally identical or similar to the amino acid sequences set forth in (c1), and (c3) amino acid sequences having at least 80% sequence identity to the amino acid sequences set forth in (c1); and (2) the first light chain variable region comprises an amino acid sequence selected from the group consisting of:

(c4) an amino acid sequence set forth in SEQ ID NO: 33, (c5) amino acid sequences derived from the amino acid sequences set forth in (c4) by substitution, deletion or addition of one or more amino acids and functionally identical or similar to the amino acid sequences set forth in (c4), and (c6) amino acid sequences having at least 80% sequence identity to the amino acid sequences set forth in (c4); and the anti-PD-L1 antibody or antigen-binding fragment thereof comprises a second heavy chain variable region and a second light chain variable region, wherein:

(1) the second heavy chain variable region comprises an amino acid sequence selected from the group consisting of:

(C1) amino acid sequences set forth in SEQ ID NOs: 110, 111, 112, 113, 114, 119, 120, 121, 122 and 123, (C2) amino acid sequences derived from the amino acid sequences set forth in (C1) by substitution, deletion or addition of one or more amino acids and functionally identical or similar to the amino acid sequences set forth in (C1), and (C3) amino acid sequences having at least 80% sequence identity to the amino acid sequences set forth in (C1); and (2) the second light chain variable region comprises an amino acid sequence selected from the group consisting of:

(C4) amino acid sequences set forth in SEQ ID NOs: 115, 116, 117, 118, 124, 125 and 126, (C5) amino acid sequences derived from the amino acid sequences set forth in (C4) by substitution, deletion or addition of one or more amino acids and functionally identical or similar to the amino acid sequences set forth in (C4), and (C6) amino acid sequences having at least 80% sequence identity to the amino acid sequences set forth in (C4).

In some specific embodiments, the present disclosure provides an anti-CD47/anti-PD-L1 antibody, wherein the first heavy chain variable region comprises an amino acid sequence selected from the group consisting of: an amino acid sequence set forth in SEQ ID NO: 30, amino acid sequences derived from SEQ ID NO: 30 by substitution, deletion or addition of one or more amino acids and functionally identical to SEQ ID NO: 30, and amino acid sequences having at least 85% sequence identity to SEQ ID NO: 30; and the first light chain variable region comprises an amino acid sequence selected from the group consisting of: an amino acid sequence set forth in SEQ ID NO: 33, amino acid sequences derived from SEQ ID NO: 33 by substitution, deletion or addition of one or more amino acids and functionally identical to SEQ ID NO: 33, and amino acid sequences having at least 85% sequence identity to SEQ ID NO: 33; and the second heavy chain variable region comprises an amino acid sequence selected from the group consisting of: amino acid sequences set forth in SEQ ID NOs: 110, 111, 112, 113 and 114, amino acid sequences derived from SEQ ID NO: 110, 111, 112, 113 or 114 by substitution, deletion or addition of one or more amino acids and functionally identical to SEQ ID NO: 110, 111, 112, 113 or 114, and amino acid sequences having at least 85% sequence identity to SEQ ID NO: 110, 111, 112, 113 or 114; and the second light chain variable region comprises an amino acid sequence selected from the group consisting of: amino acid sequences set forth in SEQ ID NOs: 115, 116, 117 and 118, amino acid sequences derived from SEQ ID NO: 115, 116, 117 or 118 by substitution, deletion or addition of one or more amino acids and functionally identical to SEQ ID NO: 115, 116, 117 or 118, and amino acid sequences having at least 85% sequence identity to SEQ ID NO: 115, 116, 117 or 118.

In some specific embodiments, the present disclosure provides an anti-CD47/anti-PD-L1 antibody, wherein the first heavy chain variable region comprises an amino acid sequence selected from the group consisting of: an amino acid sequence set forth in SEQ ID NO: 30, amino acid sequences derived from SEQ ID NO: 30 by substitution, deletion or addition of one or more amino acids and functionally identical to SEQ ID NO: 30, and amino acid sequences having at least 85% sequence identity to SEQ ID NO: 30; and the first light chain variable region comprises an amino acid sequence selected from the group consisting of: an amino acid sequence set forth in SEQ ID NO: 33, amino acid sequences derived from SEQ ID NO: 33 by substitution, deletion or addition of one or more amino acids and functionally identical to SEQ ID NO: 33, and amino acid sequences having at least 85% sequence identity to SEQ ID NO: 33; and the second heavy chain variable region comprises an amino acid sequence selected from the group consisting of: amino acid sequences set forth in SEQ ID NOs: 119, 120, 121, 122 and 123, amino acid sequences derived from SEQ ID NO: 119, 120, 121, 122 or 123 by substitution, deletion or addition of one or more amino acids and functionally identical to SEQ ID NO: 119, 120, 121, 122 or 123, and amino acid sequences having at least 85% sequence identity to SEQ ID NO: 119, 120, 121, 122 or 123; and the second light chain variable region comprises an amino acid sequence selected from the group consisting of: amino acid sequences set forth in SEQ ID NOs: 124, 125 and 126, amino acid sequences derived from SEQ ID NO: 124, 125 or 126 by substitution, deletion or addition of one or more amino acids and functionally identical to SEQ ID NO: 124, 125 or 126, and amino acid sequences having at least 85% sequence identity to SEQ ID NO: 124, 125 or 126.

In some specific embodiments, the present disclosure provides an anti-CD47/anti-PD-L1 antibody, wherein the first heavy chain variable region comprises an amino acid sequence selected from the group consisting of: an amino acid sequence set forth in SEQ ID NO: 30, amino acid sequences derived from SEQ ID NO: 30 by substitution, deletion or addition of one or more amino acids and functionally identical to SEQ ID NO: 30, and amino acid sequences comprising H1CDR1, H1CDR2 and H1CDR3 set forth in SEQ ID NOs: 4, 5 and 6 and having at least 85% sequence identity to SEQ ID NO: 30; and the first light chain variable region comprises an amino acid sequence selected from the group consisting of: an amino acid sequence set forth in SEQ ID NO: 33, amino acid sequences derived from SEQ ID NO: 33 by substitution, deletion or addition of one or more amino acids and functionally identical to SEQ ID NO: 33, and amino acid sequences comprising L1CDR1, L1CDR2 and L1CDR3 set forth in SEQ ID NOs: 15, 16 and 17 and having at least 85% sequence identity to SEQ ID NO: 33; and the second heavy chain variable region comprises an amino acid sequence selected from the group consisting of: amino acid sequences set forth in SEQ ID NOs: 110, 111, 112, 113 and 114, amino acid sequences derived from SEQ ID NO: 110, 111, 112, 113 or 114 by substitution, deletion or addition of one or more amino acids and functionally identical to SEQ ID NO: 110, 111, 112, 113 or 114, and amino acid sequences comprising H2CDR1, H2CDR2 and H2CDR3 set forth in SEQ ID NOs: 75, 76 and 77 and having at least 85% sequence identity to SEQ ID NO: 110, 111, 112, 113 or 114; and the second light chain variable region comprises an amino acid sequence selected from the group consisting of: amino acid sequences set forth in SEQ ID NOs: 115, 116, 117 and 118, amino acid sequences derived from SEQ ID NO: 115, 116, 117 or 118 by substitution, deletion or addition of one or more amino acids and functionally identical to SEQ ID NO: 115, 116, 117 or 118, and amino acid sequences comprising L2CDR1, L2CDR2 and L2CDR3 set forth in SEQ ID NOs: 78, 79 and 80 and having at least 85% sequence identity to SEQ ID NO: 115, 116, 117 or 118.

In some specific embodiments, the present disclosure provides an anti-CD47/anti-PD-L1 antibody, wherein the first heavy chain variable region comprises an amino acid sequence selected from the group consisting of: an amino acid sequence set forth in SEQ ID NO: 30, amino acid sequences derived from SEQ ID NO: 30 by substitution, deletion or addition of one or more amino acids and functionally identical to SEQ ID NO: 30, and amino acid sequences comprising H1CDR1, H1CDR2 and H1CDR3 set forth in SEQ ID NOs: 4, 5 and 6 and having at least 85% sequence identity to SEQ ID NO: 30; and the first light chain variable region comprises an amino acid sequence selected from the group consisting of: an amino acid sequence set forth in SEQ ID NO: 33, amino acid sequences derived from SEQ ID NO: 33 by substitution, deletion or addition of one or more amino acids and functionally identical to SEQ ID NO: 33, and amino acid sequences comprising L1CDR1, L1CDR2 and L1CDR3 set forth in SEQ ID NOs: 15, 16 and 17 and having at least 85% sequence identity to SEQ ID NO: 33; and the second heavy chain variable region comprises an amino acid sequence selected from the group consisting of: amino acid sequences set forth in SEQ ID NOs: 110, 111, 112, 113 and 114, amino acid sequences derived from SEQ ID NO: 110, 111, 112, 113 or 114 by substitution, deletion or addition of one or more amino acids and functionally identical to SEQ ID NO: 110, 111, 112, 113 or 114, and amino acid sequences comprising H2CDR1, H2CDR2 and H2CDR3 set forth in SEQ ID NOs: 87, 88 and 89 and having at least 85% sequence identity to SEQ ID NO: 110, 111, 112, 113 or 114; and the second light chain variable region comprises an amino acid sequence selected from the group consisting of: amino acid sequences set forth in SEQ ID NOs: 115, 116, 117 and 118, amino acid sequences derived from SEQ ID NO: 115, 116, 117 or 118 by substitution, deletion or addition of one or more amino acids and functionally identical to SEQ ID NO: 115, 116, 117 or 118, and amino acid sequences comprising L2CDR1, L2CDR2 and L2CDR3 set forth in SEQ ID NOs: 90, 91 and 92 and having at least 85% sequence identity to SEQ ID NO: 115, 116, 117 or 118.

In some specific embodiments, the present disclosure provides an anti-CD47/anti-PD-L1 antibody, wherein the first heavy chain variable region comprises an amino acid sequence selected from the group consisting of: an amino acid sequence set forth in SEQ ID NO: 30, amino acid sequences derived from SEQ ID NO: 30 by substitution, deletion or addition of one or more amino acids and functionally identical to SEQ ID NO: 30, and amino acid sequences comprising H1CDR1, H1CDR2 and H1CDR3 set forth in SEQ ID NOs: 4, 5 and 6 and having at least 85%, at least 90%, at least 95%, or at least 98% sequence identity to SEQ ID NO: 30; and the first light chain variable region comprises an amino acid sequence selected from the group consisting of: an amino acid sequence set forth in SEQ ID NO: 33, amino acid sequences derived from SEQ ID NO: 33 by substitution, deletion or addition of one or more amino acids and functionally identical to SEQ ID NO: 33, and amino acid sequences comprising L1CDR1, L1CDR2 and L1CDR3 set forth in SEQ ID NOs: 15, 16 and 17 and having at least 85%, at least 90%, at least 95%, or at least 98% sequence identity to SEQ ID NO: 33; and the second heavy chain variable region comprises an amino acid sequence selected from the group consisting of: an amino acid sequence set forth in SEQ ID NO: 112, amino acid sequences derived from SEQ ID NO: 112 by substitution, deletion or addition of one or more amino acids and functionally identical to SEQ ID NO: 112, and amino acid sequences comprising H2CDR1, H2CDR2 and H2CDR3 set forth in SEQ ID NOs: 75, 76 and 77 and having at least 85%, at least 90%, at least 95%, or at least 98% sequence identity to SEQ ID NO: 112; and the second light chain variable region comprises an amino acid sequence selected from the group consisting of: an amino acid sequence set forth in SEQ ID NO: 116, amino acid sequences derived from SEQ ID NO: 116 by substitution, deletion or addition of one or more amino acids and functionally identical to SEQ ID NO: 116, and amino acid sequences comprising L2CDR1, L2CDR2 and L2CDR3 set forth in SEQ ID NOs: 78, 79 and 80 and having at least 85%, at least 90%, at least 95%, or at least 98% sequence identity to SEQ ID NO: 116.

In other specific embodiments, the present disclosure provides an anti-CD47/anti-PD-L1 antibody, wherein the first heavy chain variable region comprises an amino acid sequence selected from the group consisting of: an amino acid sequence set forth in SEQ ID NO: 30, amino acid sequences derived from SEQ ID NO: 30 by substitution, deletion or addition of one or more amino acids and functionally identical to SEQ ID NO: 30, and amino acid sequences comprising H1CDR1, H1CDR2 and H1CDR3 set forth in SEQ ID NOs: 4, 5 and 6 and having at least 85%, at least 90%, at least 95%, or at least 98% sequence identity to SEQ ID NO: 30; and the first light chain variable region comprises an amino acid sequence selected from the group consisting of: an amino acid sequence set forth in SEQ ID NO: 33, amino acid sequences derived from SEQ ID NO: 33 by substitution, deletion or addition of one or more amino acids and functionally identical to SEQ ID NO: 33, and amino acid sequences comprising L1CDR1, L1CDR2 and L1CDR3 set forth in SEQ ID NOs: 15, 16 and 17 and having at least 85%, at least 90%, at least 95%, or at least 98% sequence identity to SEQ ID NO: 33; and the second heavy chain variable region comprises an amino acid sequence selected from the group consisting of: an amino acid sequence set forth in SEQ ID NO: 123, amino acid sequences derived from SEQ ID NO: 123 by substitution, deletion or addition of one or more amino acids and functionally identical to SEQ ID NO: 123, and amino acid sequences comprising H2CDR1, H2CDR2 and H2CDR3 set forth in SEQ ID NOs: 87, 88 and 89 and having at least 85%, at least 90%, at least 95%, or at least 98% sequence identity to SEQ ID NO: 123; and the second light chain variable region comprises an amino acid sequence selected from the group consisting of: an amino acid sequence set forth in SEQ ID NO: 126, amino acid sequences derived from SEQ ID NO: 126 by substitution, deletion or addition of one or more amino acids and functionally identical to SEQ ID NO: 126, and amino acid sequences comprising L2CDR1, L2CDR2 and L2CDR3 set forth in SEQ ID NOs: 90, 91 and 92 and having at least 85%, at least 90%, at least 95%, or at least 98% sequence identity to SEQ ID NO: 126.

In some embodiments, the present disclosure provides an anti-CD47/anti-PD-L1 humanized antibody, wherein the heavy chain comprises a heavy chain constant region of humanized IgG1, IgG2, IgG3, IgG4, or a variant thereof, and the light chain comprises a light chain constant region of humanized kappa chain, lambda chain, or a variant thereof.

In a preferred embodiment of the present disclosure, the murine-derived anti-CD47/anti-PD-L1 antibody may further comprise a light chain constant region of murine-derived kappa chain, lambda chain, or a variant thereof, and/or further comprise a heavy chain constant region of murine-derived IgG1, IgG2, IgG3, IgG4, or a variant thereof.

In a specific embodiment of the present disclosure, for the anti-CD47/anti-PD-L1 antibody according to the present disclosure, the light chain of the anti-CD47 antibody or antigen-binding fragment thereof further comprises a light chain constant region of murine-derived kappa chain, lambda chain, or mutant sequences thereof. The heavy chain of the anti-CD47 antibody or antigen-binding fragment thereof further comprises a heavy chain constant region of murine-derived IgG1, IgG2, IgG3, IgG4, or mutant sequences thereof, preferably a heavy chain constant region of humanized IgG1, IgG2 or IgG4.

In some specific embodiments, for the anti-CD47/anti-PD-L1 antibody according to the present disclosure, the anti-CD47 humanized antibody or antigen-binding fragment thereof further comprises a heavy chain constant region of humanized IgG1, IgG2, IgG3, IgG4, or a variant thereof, and a light chain constant region of humanized kappa chain, lambda chain, or a variant thereof. In some preferred embodiments, the anti-CD47 humanized antibody or antigen-binding fragment thereof of the present disclosure further comprises a heavy chain constant region of humanized IgG1, IgG2, IgG4, or a variant thereof, and a light chain constant region of humanized kappa chain or a variant thereof.

In a preferred embodiment of the present disclosure, for the anti-CD47/anti-PD-L1 antibody according to the present disclosure, the antibody heavy chain of the anti-PD-L1 antibody or antigen-binding fragment thereof further comprises a heavy chain constant region of murine-derived IgG1, IgG2, IgG3, IgG4, or mutant sequences thereof, preferably a heavy chain constant region of humanized IgG or mutant sequences thereof; and the antibody light chain of the anti-PD-L1 antibody or antigen-binding fragment thereof further comprises a light chain constant region of murine-derived kappa chain, lambda chain, or mutant sequences thereof.

In some specific embodiments, for the anti-CD47/anti-PD-L1 antibody according to the present disclosure, the anti-PD-L1 humanized antibody or antigen-binding fragment thereof further comprises a heavy chain constant region of humanized IgG1, IgG2, IgG3, IgG4, or a variant thereof, and a light chain constant region of humanized kappa chain, lambda chain, or a variant thereof. In some preferred embodiments, the anti-CD47 humanized antibody or antigen-binding fragment thereof of the present disclosure further comprises a heavy chain constant region of humanized IgG4 or a variant thereof, and a light chain constant region of humanized kappa chain or a variant thereof.

In some embodiments, the present disclosure provides an anti-CD47/anti-PD-L1 antibody, wherein the anti-CD47 antibody or antigen-binding fragment thereof and the anti-PD-L1 antibody or antigen-binding fragment thereof are each independently Fab, Fv, sFv or $F(ab)_2$. In a specific embodiment, the anti-CD47/anti-PD-L1 antibody provided by the present disclosure is $scF(ab)_2$.

Preferably, the anti-CD47/anti-PD-L1 antibody in the above embodiments of the present disclosure is an anti-CD47/anti-PD-L1 bispecific antibody. In some embodiments, the bispecific antibody is a human antibody or a humanized antibody. In some embodiments, one of the binding sites is for CD47 and the other is for any other antigen. In some embodiments, one of the binding sites is for CD47 and the other is for PD-L1. In some embodiments, the bispecific antibody binds to two different epitopes of CD47. The bispecific antibodies can also be used to localize a cytotoxic agent to cells expressing CD47. These antibodies possess a CD47 binding arm and a binding arm of a cytotoxic agent such as saporin, anti-interferon-α, *vinca* alkaloids, ricin A chain, methotrexate or radioisotope haptens. The bispecific antibody of the present disclosure may be prepared as a full-length antibody or antibody fragments (e.g., $F(ab')_2$ bispecific antibody).

Methods for preparing bispecific antibodies are known in the art. Traditionally, the recombination and preparation of bispecific antibodies are based on the co-expression of two heavy chain-light chain pairs of immunoglobulin, where the two heavy chains have different specificities (Millstein and Cuello, Nature 305: 537 (1983)). Due to the random assortment of immunoglobulin heavy and light chains, the quadromas may produce a mixture of 10 different antibody molecules, only one of which has the correct bispecific structure. Purification of this correct molecule is usually carried out by an affinity chromatography, which is rather cumbersome and product yield is low. Similar methods are disclosed in WO93/08829 and Traunecker et al., EMBOJ. 10:3655 (1991).

According to a different method, an antibody variable region with the desired binding specificities (antibody-antigen binding sites) is fused to an immunoglobulin constant region. In some embodiments, it is fused to an immunoglobulin heavy chain constant region comprising at least a portion of the hinge region, CH2 and CH3 regions. In some embodiments, the first heavy chain constant region (CH1) comprising the site necessary for binding to the light chain is present in at least a portion of the fusion. The DNA encoding the fusion fragment of the immunoglobulin heavy chain and, if desired, the immunoglobulin light chain, are inserted into separate expression vectors and co-transfected into a suitable host organism. This provides great flexibility for adjusting the mutual ratios of the three polypeptide fragments in embodiments where unequal ratios of the three polypeptide chains used in the construction provide optimal yields. However, it is possible to insert the coding sequences for two or all three polypeptide chains into one expression vector when at least two polypeptide chains are expressed in equal ratios to produce high yields or when the ratios are not of particular interest.

In one embodiment, the bispecific antibody is comprised of a hybrid immunoglobulin heavy chain with a first binding site in one arm and a hybrid immunoglobulin heavy chain-light chain pair in the other arm (providing a second binding site). Since the presence of the immunoglobulin light chain in only one half of the bispecific molecule provides a convenient separation route, this asymmetric structure facilitates separation of the desired bispecific material from the undesired immunoglobulin chain composition. This method is disclosed in WO 94/04690. For further information on the production of bispecific antibodies, reference could be made to, e.g., Suresh et al., Methods in Enzymology 121: 210 (1986).

According to another method, the interface between a pair of antibody molecules may be engineered to maximize the percentage of heterodimers recovered from recombinant cell culture. The interface comprises at least a portion of the CH3 domain of the antibody constant region. In this method, one or more small amino acids on the side chain at the interface of the first antibody molecule are replaced with big amino acids (e.g., tyrosine or tryptophan). By replacing big amino acids on the side chain with smaller amino acids (e.g., alanine or threonine), a compensatory "hole" of the same or similar size as the large side chain is created at the interface of the second antibody molecule. This provides a mechanism for heterodimers with increased yield than other undesired end products such as homodimers.

Bispecific antibodies include cross-linked or "heteroconjugated" antibodies. For example, a heteroconjugated antibody may be conjugated to avidin and the other heteroconjugated antibody may be conjugated to biotin. Heteroconjugated antibodies can be prepared using any convenient cross-linking method. Suitable crosslinking agents are well known in the art and disclosed in U.S. Pat. No. 4,676,980, along with a number of crosslinking techniques.

The bispecific antibody of the present disclosure may be produced from antibody fragments. For example, bispecific antibodies may be prepared using chemical ligation techniques. Brennan et al., Science 229: 81 (1985) describes the proteolytic cleavage of intact antibodies to generate $F(ab')_2$ fragments. These fragments are decomposed in the presence of the dithiol complexing agent sodium arsenite (to stabilize adjacent dithiols and prevent the formation of intermolecular disulfide bonds). The resulting Fab' fragments were then converted into thionitrobenzoate (TNB) derivatives. One of the Fab'-TNB derivatives was then reconverted to Fab'-thiol by reduction with mercaptoethylamine and mixed with an equimolar amount of the other Fab'-TNB derivative to form a bispecific antibody.

Fab'-SH fragments may be recovered directly from *E. coli* and these fragments may be chemically coupled to form a bispecific antibody. Shalaby et al., J. Exp. Med. 175: 217-225 (1992) describes the generation of fully humanized bispecific antibody $F(ab')_2$ molecules. Each Fab' fragment is secreted separately from *E. coli* and subjected to targeted chemical coupling in vitro to form a bispecific antibody.

In some embodiments, bispecific antibody fragments of the present disclosure may be produced and isolated directly from recombinant cell culture. For example, bispecific antibodies may be generated using leucine zippers (Kostelny et al., J. Immunol. 148(5): 1547-1553 (1992)). Leucine zipper segments from Fos and Jun proteins were linked to the Fab' portions of two different antibodies by genetic fusion. Antibody homodimers are decomposed at the hinge region to form monomers, which are then reoxidized to form antibody heterodimers. This method can also be used to generate antibody homodimers. Diabody technology provides additional mechanisms for preparing bispecific antibody fragments. The bispecific antibody fragment comprises a heavy chain variable region (VH) and a light chain variable region (VL) joined by a linker that is too short to allow pairing between the two domains on the same chain. Thus, the VH and VL domains on one fragment are forced to pair with the complementary VL and VH domains on the other fragment, thereby forming two antigen binding sites. In another embodiment, bispecific antibody fragments may be constructed by using single-chain Fv (sFv) dimers.

The present disclosure encompasses multi-specific antibodies with more than two binding sites. For example, trispecific antibodies may be prepared. Multi-specific antibodies may be assimilated (and/or dissimilated) more rapidly than bivalent antibodies by cells expressing the antigens to which the antibody binds. The antibody of the present disclosure may be a multi-specific antibody (e.g., a tetravalent antibody) having three or more antigen binding sites that can be readily produced by recombinant expression of nucleic acids encoding antibody polypeptide chains. Multi-specific antibodies may contain a dimerization domain and three or more antigen binding sites. In some embodiments, the dimerization domain comprises (or consists of) an Fc region or a hinge region. In such case, the antibody will comprise an Fc region and three or more antigen binding sites amino-terminal to the Fc region. In some embodiments, the multi-specific antibody comprises (or consists of) three to about eight antigen binding sites. In some embodiments, the multi-specific antibody comprises four antigen binding sites. Multi-specific antibodies comprise at least one polypeptide chain (e.g., two polypeptide chains), wherein the polypeptide chains comprise two or more variable regions. The multi-specific antibody of the present disclosure may further comprise at least two (e.g., four) light chain variable region polypeptides. The multi-specific antibody of the present disclosure may comprise, for example, about two to about eight light chain variable region polypeptides. The light chain variable region polypeptide of the present disclosure comprises a light chain variable region, and optionally, further comprises a CL domain.

In a bispecific antibody comprising a CD47 targeting moiety and a PD-L1 targeting moiety, one of the CD47 targeting moiety and the PD-L1 targeting moiety may be a full-length antibody, and the other may be an antigen binding fragment (e.g., scFv) comprising heavy chain CDRs, light chain CDRs or a combination thereof. A full-length antibody targeting one of the CD47 and PD-L1 proteins and an antigen-binding fragment targeting the other protein can be linked directly or chemically (e.g., covalently) via a peptide linker. The antigen-binding fragment (e.g., scFv) can be linked directly or via a peptide linker to the N-terminal of the full-length antibody (e.g., the N-terminal of the light or heavy chain of the full-length antibody), the C-terminal of the full-length antibody (e.g., of the heavy chain (or Fc or CH3 domain) of the full-length antibody), or both.

In one embodiment, the bispecific antibody may comprise a full-length anti-CD47 antibody, an antigen-binding fragment of an anti-PD-L1 antibody (e.g., scFab, scFv), and a peptide linker between them. In other embodiments, the bispecific antibody may comprise a full-length anti-CD47 antibody, an antigen-binding fragment of an anti-PD-L1 antibody (e.g., scFab, scFv), and a peptide linker between them.

In one embodiment, the scFv of the bispecific antibody may comprise a heavy chain variable region and a light chain variable region in any order. For example, the scFv of the bispecific antibody may comprise a heavy chain variable region and a light chain variable region in the direction from the N-terminal to the C-terminal, and optionally a peptide linker between them, or alternatively, the scFv of the bispecific antibody may comprise a light chain variable region and a heavy chain variable region in the direction from the N-terminal to the C-terminal, and optionally a peptide linker between them.

In some embodiments, the peptide linker may comprise, for example, Gly, Asn, and/or Ser residues, and may also comprise neutral amino acids, such as Thr and/or Ala. Suitable amino acid sequences for peptide linkers may be those known in the art. Meanwhile, the length of the peptide linker may be determined differently within such limits that the function of the fusion protein is not affected. For example, the peptide linker may include a total of about 1 to about 100, about 2 to about 50, or about 5 to about 25 residues selected from the group consisting of Gly, Asn, Ser, Thr, and Ala. In one embodiment, the peptide linker may be represented as $(G_mS_1)_n$(m, 1 and n are independently integers from about 1 to about 10, particularly from about 2 to about 5).

In another embodiment, the PD-L1 targeting moiety and the CD47 targeting moiety may both be full-length antibodies or antigen-binding fragments comprising heavy chain CDRs, light chain CDRs, or a combination thereof.

In another embodiment, the bispecific antibody may be in the form of a heterodimer comprising a first arm and a second arm, the first arm comprising a pair of a first heavy chain and a first light chain targeting one of CD47 and PD-L1 and the second arm comprising a pair of a second heavy chain and a second light chain targeting the other.

In one embodiment, the full-length antibody may be in the form of a full-length immunoglobulin (e.g., IgG, IgM, IgA, IgE, or IgD, such as human IgG, human IgM, human IgA, human IgE, or human IgD), and the antigen-binding fragment may be selected from the group consisting of Fab, Fab', $F(ab')_2$, Fd, Fv, scFv, scFab, single chain antibody, sdFv and the like. For example, the full-length antibody may be in the form of a full-length human IgG (human IgG1, human IgG2, human IgG3 or human IgG4), and the antigen-binding fragment may be scFv.

For example, the antibody described herein may contain a flexible linker, or may be modified to add functional moieties (e.g., PEG, drugs, toxins, or labels).

In some specific embodiments, for the anti-CD47/anti-PD-L1 bispecific antibody according to the present disclosure, the anti-CD47 antibody or antigen-binding fragment thereof has a structure of (VL-CL)-linker-(VH)-IgG4CH, and the anti-PD-L1 antibody or antigen-binding fragment thereof has a structure of (VL-CL)-linker-(VH)-IgG4CH. In some specific embodiments, the peptide linker is in the form of $(GGGGS)_n$, wherein n is 1-12, preferably 3-10, more preferably 6-8, e.g., 6, 7 or 8 GGGGS repeats. In other specific embodiments, the IgG4CH in the (VL-CL)-linker-(VH)-IgG4CH targeting the CD47 moiety is an IgG4 CH fragment containing mutations S228P, L235E, Y349C, T366S, L368A and Y407V to form a "Hole" structure, and the IgG4CH in the (VL-CL)-linker-(VH)-IgG4CH targeting the PD-L1 moiety is an IgG4 CH fragment containing mutations S228P, L235E, T366W and S354C to form a "Knob" structure. In some specific embodiments, in the (VL-CL)-linker-(VH)-IgG4CH targeting the CD47 moiety, the VL has an amino acid sequence of SEQ ID NO: 33, the CL has an amino acid sequence of SEQ ID NO: 131, the VH has an amino acid sequence of SEQ ID NO: 30, and the IgG4 CH has an amino acid sequence of SEQ ID NO: 133; and/or in the (VL-CL)-linker-(VH)-IgG4CH targeting the PD-L1 moiety, the VL has an amino acid sequence of SEQ ID NO: 116, the CL has an amino acid sequence of SEQ ID NO: 131, the VH has an amino acid sequence of SEQ ID NO: 112, and the IgG4 CH has an amino acid sequence of SEQ ID NO: 132. In other specific embodiments, in the (VL-CL)-linker-(VH)-IgG4CH targeting the CD47 moiety, the VL has an amino acid sequence of SEQ ID NO: 33, the CL has an amino acid sequence of SEQ ID NO: 131, the VH has an amino acid sequence of SEQ ID NO: 30, and the IgG4 CH has an amino acid sequence of SEQ ID NO: 133; and/or in the (VL-CL)-linker-(VH)-IgG4CH targeting the PD-L1 moiety, the VL has an amino acid sequence of SEQ ID NO: 126, the CL has an amino acid sequence of SEQ ID NO: 131, the VH has an amino acid sequence of SEQ ID NO: 123, and the IgG4 CH has an amino acid sequence of SEQ ID NO: 132.

Another aspect of the present disclosure provides an anti-PD-L1 antibody or antigen-binding fragment thereof comprising a heavy chain variable region and a light chain variable region, wherein:

(1) the heavy chain variable region comprises CDR1, CDR2 and CDR3 selected from the group consisting of:

(A1) amino acid sequences set forth in SEQ ID NOs: 75, 76 and 77;

(A2) amino acid sequences set forth in SEQ ID NOs: 81, 82 and 83;

(A3) amino acid sequences set forth in SEQ ID NOs: 87, 88 and 89;

(A4) amino acid sequences set forth in SEQ ID NOs: 93, 94 and 95; and (A5) amino acid sequences having at least 85% sequence identity to the amino acid sequences set forth in (A1), (A2), (A3) or (A4); and (2) the light chain variable region comprises CDR1, CDR2 and CDR3 selected from the group consisting of:

(A6) amino acid sequences set forth in SEQ ID NOs: 78, 79 and 80;

(A7) amino acid sequences set forth in SEQ ID NOs: 84, 85 and 86;

(A8) amino acid sequences set forth in SEQ ID NOs: 90, 91 and 92;

(A9) amino acid sequences set forth in SEQ ID NOs: 96, 97 and 98; and (A10) amino acid sequences having at least 85% sequence identity to the amino acid sequences set forth in (A6), (A7), (A8) or (A9).

In some embodiments, the anti-PD-L1 antibody or antigen-binding fragment thereof according to the present disclosure, wherein in the anti-PD-L1 antibody or antigen-binding fragment thereof:

the heavy chain variable region comprises CDR1, CDR2 and CDR3 comprising amino acid sequences set forth in SEQ ID NOs: 75, 76 and 77, or amino acid sequences having at least 85% sequence identity to the amino acid sequences set forth in SEQ ID NOs: 75, 76 and 77, respectively, and the light chain variable region comprises CDR1, CDR2 and CDR3 comprising amino acid sequences set forth in SEQ ID NOs: 78, 79 and 80, or amino acid sequences having at least 85% sequence identity to the amino acid sequences set forth in SEQ ID NOs: 78, 79 and 80, respectively;

the heavy chain variable region comprises CDR1, CDR2 and CDR3 comprising amino acid sequences set forth in SEQ ID NOs: 87, 88 and 89, or amino acid sequences having at least 85% sequence identity to the amino acid sequences set forth in SEQ ID NOs: 87, 88 and 89, respectively, and the light chain variable region comprises CDR1, CDR2 and CDR3 comprising amino acid sequences set forth in SEQ ID NOs: 90, 91 and 92, or amino acid sequences having at least 85% sequence identity to the amino acid sequences set forth in SEQ ID NOs: 90, 91 and 92, respectively; or the heavy chain variable region comprises CDR1, CDR2 and CDR3 comprising amino acid sequences set forth in SEQ ID NOs: 93, 94 and 95, or amino acid sequences having at least 85% sequence identity to the amino acid sequences set forth in SEQ ID NOs: 93, 94 and 95, respectively, and the light chain variable region comprises CDR1, CDR2 and CDR3 comprising amino acid sequences set forth in SEQ ID NOs: 96, 97 and 98, or amino acid sequences having at least 85% sequence identity to the amino acid sequences set forth in SEQ ID NOs: 96, 97 and 98, respectively.

In some embodiments, the anti-PD-L1 antibody or antigen-binding fragment thereof:

(1) the heavy chain variable region comprises an amino acid sequence selected from the group consisting of:

(B1) amino acid sequences set forth in SEQ ID NOs: 99, 100, 101, 102, 110, 111, 112, 113, 114, 119, 120, 121, 122 and 123, (B2) amino acid sequences derived from the amino acid sequences set forth in (B1) by substitution, deletion or addition of one or more amino acids and functionally identical or similar to the amino acid sequences set forth in (B1), and (B3) amino acid sequences having at least 80% sequence identity to the amino acid sequences set forth in (B1); and (2) the light chain variable region comprises an amino acid sequence selected from the group consisting of:

(B4) amino acid sequences set forth in SEQ ID NOs: 103, 104, 105, 106, 115, 116, 117, 118, 124, 125 and 126, (B5) amino acid sequences derived from the amino acid sequences set forth in (B4) by substitution, deletion or addition of one or more amino acids and functionally identical or similar to the amino acid sequences set forth in (B4), and (B6) amino acid sequences having at least 80% sequence identity to the amino acid sequences set forth in (B4).

In some embodiments, the anti-PD-L1 antibody or antigen-binding fragment thereof:

the heavy chain variable region comprises an amino acid sequence selected from the group consisting of: amino acid sequences set forth in SEQ ID NOs: 110, 111, 112, 113 and 114, amino acid sequences derived from SEQ ID NO: 110, 111, 112, 113 or 114 by substitution, deletion or addition of one or more amino acids and functionally identical to SEQ ID NO: 110, 111, 112, 113 or 114, and amino acid sequences having at least 85% sequence identity to SEQ ID NO: 110, 111, 112, 113 or 114; and the light chain variable region comprises an amino acid sequence selected from the group consisting of: amino acid sequences set forth in SEQ ID NOs: 115, 116, 117 and 118, amino acid sequences derived from SEQ ID NO: 115, 116, 117 or 118 by substitution, deletion or addition of one or more amino acids and functionally identical to SEQ ID NO: 115, 116, 117 or 118, and amino acid sequences having at least 85% sequence identity to SEQ ID NO: 115, 116, 117 or 118.

In some embodiments, the anti-PD-L1 antibody or antigen-binding fragment thereof:

the heavy chain variable region comprises an amino acid sequence selected from the group consisting of: amino acid sequences set forth in SEQ ID NOs: 119, 120, 121, 122 and 123, amino acid sequences derived from SEQ ID NO: 119, 120, 121, 122 or 123 by substitution, deletion or addition of one or more amino acids and functionally identical to SEQ ID NO: 119, 120, 121, 122 or 123, and amino acid sequences having at least 85% sequence identity to SEQ ID NO: 119, 120, 121, 122 or 123; and the light chain variable region comprises an amino acid sequence selected from the group consisting of: amino acid sequences set forth in SEQ ID NOs: 124, 125 and 126, amino acid sequences derived from SEQ ID NO: 124, 125 or 126 by substitution, deletion or addition of one or more amino acids and functionally identical to SEQ ID NO: 124, 125 or 126, and amino acid sequences having at least 85% sequence identity to SEQ ID NO: 124, 125 or 126.

In some embodiments, in the anti-PD-L1 antibody or antigen-binding fragment thereof according to the present disclosure, the heavy chain variable region comprises an amino acid sequence selected from the group consisting of: an amino acid sequence set forth in SEQ ID NO: 112, amino acid sequences derived from SEQ ID NO: 112 by substitution, deletion or addition of one or more amino acids and functionally identical to SEQ ID NO: 112, and amino acid sequences comprising H2CDR1, H2CDR2 and H2CDR3 set forth in SEQ ID NOs: 75, 76 and 77 and having at least 85%, at least 90%, at least 95%, or at least 98% sequence identity to SEQ ID NO: 112; and the light chain variable region comprises an amino acid sequence selected from the group consisting of: an amino acid sequence set forth in SEQ ID NO: 116, amino acid sequences derived from SEQ ID NO: 116 by substitution, deletion or addition of one or more amino acids and functionally identical to SEQ ID NO: 116, and amino acid sequences comprising L2CDR1, L2CDR2 and L2CDR3 set forth in SEQ ID NOs: 78, 79 and 80 and having at least 85%, at least 90%, at least 95%, or at least 98% sequence identity to SEQ ID NO: 116.

In some embodiments, in the anti-PD-L1 antibody or antigen-binding fragment thereof according to the present disclosure, the heavy chain variable region comprises an amino acid sequence selected from the group consisting of: an amino acid sequence set forth in SEQ ID NO: 123, amino acid sequences derived from SEQ ID NO: 123 by substitution, deletion or addition of one or more amino acids and functionally identical to SEQ ID NO: 123, and amino acid sequences comprising H2CDR1, H2CDR2 and H2CDR3 set forth in SEQ ID NOs: 87, 88 and 89 and having at least 85%, at least 90%, at least 95%, or at least 98% sequence identity to SEQ ID NO: 123; and the light chain variable region comprises an amino acid sequence selected from the group consisting of: an amino acid sequence set forth in SEQ ID NO: 126, amino acid sequences derived from SEQ ID NO: 126 by substitution, deletion or addition of one or more amino acids and functionally identical to SEQ ID NO: 126, and amino acid sequences comprising L2CDR1, L2CDR2 and L2CDR3 set forth in SEQ ID NOs: 90, 91 and 92 and having at least 85%, at least 90%, at least 95%, or at least 98% sequence identity to SEQ ID NO: 126.

In some embodiments, the anti-PD-L1 antibody or antigen-binding fragment thereof according to the present disclosure is a humanized antibody or a fully human antibody.

Another aspect of the present disclosure provides an isolated nucleic acid. In some embodiments, the isolated nucleic acid according to the present disclosure encodes an anti-CD47/anti-PD-L1 antibody or an anti-PD-L1 antibody of the present disclosure. In some embodiments, the isolated nucleic acid according to the present disclosure encodes an anti-CD47 antibody or antigen-binding fragment thereof of the present disclosure. In other embodiments, the isolated nucleic acid according to the present disclosure encodes an anti-PD-L1 antibody or antigen-binding fragment thereof of the present disclosure.

In a specific embodiment, the nucleotide sequence encoding the first heavy chain variable region SEQ ID NO: 30 is set forth in SEQ ID NO: 36, and the nucleotide sequence encoding the first light chain variable region SEQ ID NO: 33 is set forth in SEQ ID NO: 39. In another specific embodiment, the nucleotide sequence encoding the second heavy chain variable region SEQ ID NO: 112 is set forth in SEQ ID NO: 127, and the nucleotide sequence encoding the second light chain variable region SEQ ID NO: 116 is set forth in SEQ ID NO: 129. In yet another specific embodiment, the nucleotide sequence encoding the second heavy chain variable region SEQ ID NO: 123 is set forth in SEQ ID NO: 128, and the nucleotide sequence encoding the second light chain variable region SEQ ID NO: 126 is set forth in SEQ ID NO: 130.

Another aspect of the present disclosure provides an expression vector. In some embodiments, the expression vector of the present disclosure expresses the anti-CD47/anti-PD-L1 bispecific antibody or the anti-PD-L1 antibody of the present disclosure. In some embodiments, the expression vector of the present disclosure expresses an anti-CD47 antibody or antigen-binding fragment thereof of the present disclosure. In other embodiments, the expression vector of the present disclosure expresses an anti-PD-L1 antibody or antigen-binding fragment thereof of the present disclosure. In some embodiments, the vector expressing the anti-CD47 antibody or antigen-binding fragment thereof of the present disclosure and the vector expressing the anti-PD-L1 antibody or antigen-binding fragment thereof of the present disclosure are the same expression vector. The expression vector according to the present disclosure comprises the isolated nucleic acid molecule of the present disclosure.

Another aspect of the present disclosure provides a host cell transformed with the expression vector as described above.

In some embodiments, the host cell according to the present disclosure is selected from the group consisting of prokaryotic cells and eukaryotic cells. In some embodiments, the host cell is bacteria, preferably *Escherichia coli*. In another preferred embodiment, the host cell is mammalian cell.

Another aspect of the present disclosure provides a method for producing the anti-CD47/anti-PD-L1 bispecific antibody, comprising expressing the antibody in the host cells and isolating the antibody from the host cells.

Another aspect of the present disclosure provides a pharmaceutical composition comprising the anti-CD47/anti-PD-L1 bispecific antibody of the present disclosure and a pharmaceutically acceptable carrier. In some embodiments, the present disclosure provides a pharmaceutical composition comprising the anti-CD47/anti-PD-L1 bispecific antibody of the present disclosure, and additional active components, such as other antibodies, targeted drugs, and the like. In some embodiments, the pharmaceutically acceptable carrier is selected from the group consisting of antioxidants, polypeptides, proteins, hydrophilic polymers, amino acids, saccharides, chelating agents, alditols, ions, and surfactants. In a specific embodiment, the pharmaceutically acceptable carrier is a buffered aqueous solution. In another specific embodiment, the pharmaceutically acceptable carrier is in the form of liposomes.

Another aspect of the present disclosure provides a chimeric antigen receptor (CAR) fusion protein comprising the anti-CD47 antibody or antigen-binding fragment thereof and/or anti-PD-L1 antibody or antigen-binding fragment thereof of the present disclosure. In some embodiments, the chimeric antigen receptor fusion protein comprises the anti-CD47 antibody or antigen-binding fragment thereof of the present disclosure, which is a single-chain variable fragment (scFv) of $V_H$ and $V_L$ against CD47 antigen. In other embodiments, the chimeric antigen receptor fusion protein comprises the anti-PD-L1 antibody or antigen-binding fragment thereof of the present disclosure, which is a single-chain variable fragment (scFv) of $V_H$ and $V_L$ against PD-L1 antigen. In other embodiments, the chimeric antigen receptor fusion protein comprises a first single-chain variable fragment (scFv) of $V_H$ and $V_L$ against CD47 antigen and a second single-chain variable fragment (scFv) of $V_H$ and $V_L$ against PD-L1 antigen. The first scFv against CD47 antigen comprises H1CDR1, H1CDR2 and H1CDR3 of the first heavy chain variable region and L1CDR1, L1CDR2 and L1CDR3 of the first light chain variable region as described in the above embodiments. The second scFv against PD-L1 antigen comprises H2CDR1, H2CDR2 and H2CDR3 of the second heavy chain variable region and L2CDR1, L2CDR2 and L2CDR3 of the second light chain variable region as described in the above embodiments.

The anti-CD47/anti-PD-L1 bispecific antibody of the present disclosure may be combined with a pharmaceutically acceptable carrier, diluent or excipient to prepare a pharmaceutical preparation suitable for oral or parenteral administration. The routes of administration include, but are not limited to oral, intradermal, intramuscular, intraperitoneal, intravenous, intracerebral, intraocular, intratracheal, subcutaneous, and intranasal routes. The preparation may be administered by any means, for example, by infusion or bolus injection, by the means of absorption through epithelium or skin mucosa (for example, oral mucosa or rectum, etc.). Administration can be systemic or local. The preparation can be prepared by methods known in the art, and contains a carrier, diluent or excipient conventionally used in the field of pharmaceutical preparations.

Another aspect of the present disclosure provides a method for treating and/or preventing a disease associated with CD47, PD-L1 or both. The method comprises administering to a subject in need thereof the anti-CD47/anti-PD-L1 bispecific antibody of the present disclosure or the pharmaceutical composition of the present disclosure.

Another aspect of the present disclosure provides use of the anti-CD47/anti-PD-L1 bispecific antibody or the anti-PD-L1 antibody of the present disclosure or the pharmaceutical composition of the present disclosure in the manufacture of a medicament for treating and/or preventing a disease associated with CD47, PD-L1 or both. In some embodiments, the disease associated with CD47, PD-L1, or both includes hematological tumor, lymphoma, breast cancer, lung cancer, gastric cancer, intestinal cancer, esophageal cancer, ovarian cancer, cervical cancer, kidney cancer, bladder cancer, pancreatic cancer, glioma and/or melanoma. The tumor may be any type of tumor that expresses PD-L1 protein, such as bladder cancer, liver cancer, colon cancer, rectal cancer, endometrial cancer, leukemia, lymphoma, pancreatic cancer, lung cancer (e.g., small cell lung cancer, non-small cell lung cancer, etc.), breast cancer, urethral cancer, head and neck cancer, gastrointestinal cancer, gastric cancer, esophageal cancer, ovarian cancer, kidney cancer, melanoma, prostate cancer, thyroid cancer, etc. The tumor may be a primary or metastatic tumor. In some embodiments, the present disclosure provides use of the above anti-CD47/anti-PD-L1 bispecific antibody or the pharmaceutical composition of the present disclosure in the manufacture of anti-tumor drugs. For example, the tumor is selected from hematological tumor, lymphoma, breast cancer, lung cancer, gastric cancer, intestinal cancer, esophageal cancer, ovarian cancer, cervical cancer, kidney cancer, bladder cancer, pancreatic cancer, glioma and melanoma.

The anti-CD47/anti-PD-L1 bispecific antibodies provided by the present disclosure have a significant anti-tumor effect and can significantly inhibit tumor growth without obvious toxicity on red blood cells. The humanized antibodies, of which the immunogenicity is greatly reduced, effectively eliminate the rejection of exogenous monoclonal antibodies by human immune system and can be used in the manufacture of medicaments for the treatment of various tumors with broad market prospects.

Definitions

Unless otherwise defined, the meanings of scientific and technical terms used herein are those commonly understood by those skilled in the art. The nomenclature and techniques used in cell and tissue culture, molecular biology, as well as protein and oligo/polynucleotide chemistry and hybridization described herein are well known and commonly used in the art. Standard techniques are used for recombinant DNA, oligonucleotide synthesis, tissue culture and transformation (e.g. electroporation, lipofection). The enzymatic reaction and purification techniques are carried out according to the manufacturer's instructions or methods commonly used in the art or described herein. The aforementioned techniques and methods are generally used according to what's well known in the art and what's described in the multiple comprehensive and more specific documents cited and discussed in this specification. Reference could be made to, Sambrook et al., Molecular Cloning: A Laboratory Manual (2nd edition, Cold Spring Harbor Laboratory Press, Cold Spring Harbor, New York (1989)). The nomenclature as well as laboratory methods and techniques used in analytical chemistry, synthetic organic chemistry, and medical and pharmaceutical chemistry described herein are well known and commonly used in the art.

In the present disclosure, the term "at least 80% sequence identity" refers to at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity. In the present disclosure, the term "at least 85% sequence identity" refers to at least 85%, 86%, 87%, 88%, 89%, 90%, 91%, 92%, 93%, 94%, 95%, 96%, 97%, 98%, 99%, or 100% sequence identity. In some preferred embodiments, the sequence identity described in the present disclosure may be at least 90%, 91%, 92%, 93%, 94%, 95%, 96%, 97%, 98%, 99%, or 100%. Sequence comparison and determination of identity percentage between two sequences may be performed by the BLASTN/BLASTP algorithm on the website of National Center for Biotechnology Institute.

In an antibody molecule, three hypervariable regions of the light chain and three hypervariable regions of the heavy chain are arranged relative to each other in a three-dimensional space to form an antigen-binding surface. The antigen-binding surface is complementary to the three-dimensional surface of the bound antigen, and the three hypervariable regions of each heavy chain and light chain are referred as "complementarity determining region" or "CDR". The assignment of amino acids to each domain is defined by Kabat "Sequences of Proteins of Immunological Interest" (National Institutes of Health, Bethesda, Maryland (1987 and 1991)) or Chothia and Lesk (J. Mol. Biol. 196:901-917 (1987), Chothia et al., Nature 342:878-883 (1989)).

The "antibody" of the present disclosure refers to a polypeptide or a polypeptide complex that specifically recognizes and binds to an antigen. The antibody may be an intact antibody and any antigen-binding fragments or single chains thereof. The "antibody" of the present disclosure includes any protein or peptide containing at least a portion of an Ig molecule that has the biological activity of binding to an antigen. Examples of the "antibody" of the present disclosure include, but are not limited to, heavy or light chain CDRs or ligand binding portions thereof, heavy or light chain variable regions, heavy or light chain constant regions, framework regions, or any portion thereof.

The "antigen-binding fragment" of the present disclosure includes the following fragment with antigen-binding activity: Fab fragment, Fab' fragment, $F(ab')_2$ fragment, and Fv fragment and scFv fragment that bind to human CD47 or PD-L1. The Fv fragment comprises a first heavy chain variable region and a first light chain variable region of the antibody but no constant region, and it is the smallest antibody fragment with all antigen binding sites. Generally, Fv antibody also comprises a polypeptide linker between the VH and VL domains, and is able to form the structure required for antigen binding. Different linkers may also be utilized to link the two variable regions of antibody to form a polypeptide chain, which is called single-chain antibody or single-chain Fv (scFv). The anti-CD47 or anti-PD-L1 antibody of the present disclosure may be a single-chain variable fragment (scFv), which is derived from the single-chain polypeptide of an antibody and retains the ability to bind to antigen. Examples of scFv include antibody polypeptides generated by recombinant DNA techniques in which the Fv regions of immunoglobulin heavy chain (H chain) and light chain (L chain) fragments are linked via a spacer sequence. Various methods for preparing scFv are well known to those skilled in the art.

The antibody of the present disclosure refers to an immunoglobulin molecule or an immunologically active part thereof, that is, a molecule that contains antigen-binding sites that specifically bind to the antigen (through immunological reaction). "Specific binding" means that an antibody reacts with one or more antigenic determinants of an antigen but does not react with other polypeptides, or it binds to other polypeptides with very low affinity ($Kd>10^{-6}$). Antibodies include but are not limited to polyclonal, monoclonal, chimeric, dAb (domain antibody), single chain, Fab, Fab' and $F(ab')_2$ fragment, Fv, scFv and Fab expression library. A monoclonal antibody (mAb) is the antibody obtained from a single cloned cell line, and the said cell line is not limited to eukaryotic, prokaryotic or phage cloned cell lines. A monoclonal antibody or antigen-binding fragment thereof can be obtained by recombination using, for example, hybridoma technology, recombination technology, phage display technology, and synthesis technology such as CDR grafting, or other existing technology.

The "murine-derived antibody" of the present disclosure is a monoclonal antibody against human CD47 produced according to the knowledge and skills in the art. During the production, the test subject is injected with the CD47 antigen, and then the hybridomas expressing the antibody with the desired sequence or functional property are isolated.

The "chimeric antibody" of the present disclosure is an antibody formed by fusing the variable regions of a murine-derived antibody with the constant regions of a human antibody, which can reduce the immune response induced by the murine-derived antibody. To establish a chimeric antibody, it is necessary to establish a hybridoma secreting murine-derived specific monoclonal antibodies first, clone the variable region genes from the mouse hybridoma cells, and then clone the constant region genes of the human antibody as needed, and chimeric genes formed by linking the mouse variable region with the human constant region genes are inserted into a human vector. Finally, the chimeric antibody is expressed in a eukaryotic system or a prokaryotic system.

The "humanized antibody" of the present disclosure is also called a CDR grafted antibody, which is the antibody produced by grafting mouse CDR sequences into the framework (FR) of a human antibody. Such framework sequences of variable region may be obtained from public DNA databases or public references, for example, from the ImMunoGeneTics (IMGT) website http://imgt.cines.fr or from the Journal of Immunoglobulin, 2001ISBN012441351.

The "bispecific antibody" as used herein refers to a monoclonal antibody that has binding sites for at least two different antigens.

The "peptide linker" as used herein may be those comprising any amino acid from 1 to 10, especially 2 to 50, and may comprise any kind of amino acids without any limitation.

DETAILED DESCRIPTION

Figure 1:
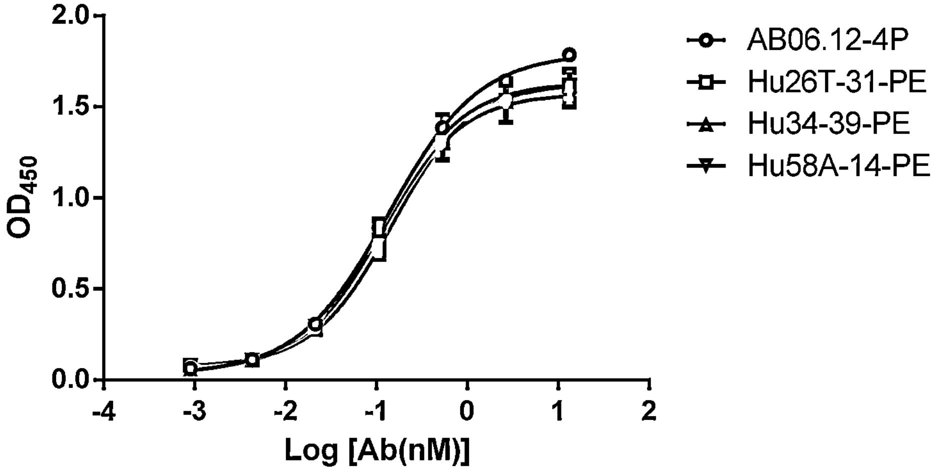
FIG. 1 shows the results of the binding activity assay (ELISA) of the humanized anti-CD47 antibodies to monkey CD47.

The following representative examples are used to illustrate the present disclosure better, rather than to limit the scope of protection of the present disclosure. The experimental methods without conditions indicated in the following examples are usually carried out according to conventional conditions, such as the antibody technology experiment manual and molecular cloning manual of Cold Spring Harbor, or according to the conditions recommended by the raw material or commodity manufacturers. The materials and reagents used in the examples are all commercially available unless otherwise specified.

Example 1 Preparation of CD47 Antigen Protein and Anti-CD47 Positive Control Antibody 1. Construction of Expression Vector of Antigen and Positive Control Antibody (1) Construction of Expression Vector of Antigen A gene fragment encoding the full length of CD47 protein was synthesized, and the amino acid sequence is shown in SEQ ID NO: 41. This fragment was cloned into the eukaryotic expression plasmid pTargeT to generate the CD47 expression plasmid pTargeT-CD47.

The amino acid sequence of the extracellular region of the human CD47 protein was fused with the amino acid sequence of hIgG1-Fc or his-tag, and the designed amino acid sequences are shown in SEQ ID NO: 42 and SEQ ID NO: 43, respectively. After codon optimization of the above sequences encoding amino acids, the tagged extracellular region of CD47 protein coding fragments, CD47-hFc and CD47-his, were synthesized and cloned into the eukaryotic expression plasmid pHR respectively to generate expression plasmids pHR-CD47-hFc and pHR-CD47-his.

The amino acid sequence of the extracellular region of the human CD47 protein was fused with the amino acid sequence of mIgG1-Fc, and the designed amino acid sequence is shown in SEQ ID NO: 44. After codon optimization of the sequence, a complete expression plasmid pcDNA3.1(+)-TPA-CD47-mIgG1-Fc was constructed.

The sequence of SIRPα is shown in SEQ ID NO: 45. After codon optimization of the sequence, a complete expression plasmid pcDNA3.1(+)-SIRPα-myc-His was constructed.

(2) Construction of Expression Vector of Positive Control Antibody

The antibody AB6.12-IgG4P (abbreviated as AB06.12-4P hereinafter) disclosed in the patent application WO2013/119714 was used as a positive control antibody. The amino acid sequences of AB06.12-4P are as follows:

- heavy chain amino acid sequence of AB06.12-4P is shown in SEQ ID NO: 46; and
- light chain amino acid sequence of AB06.12-4P is shown in SEQ ID NO: 47.

The amino acid sequence corresponding to the above antibody sequences were artificially optimized to generate the heavy chain and light chain expression plasmids pcDNA3.1(+)-SHC025-hG4 and pcDNA3.1(+)-SHC025-hk of the positive control antibody AB06.12-4P. The heavy chain fragment was cloned into the eukaryotic expression plasmid pHR containing the light chain constant region of IgG4 to obtain the heavy chain eukaryotic expression plasmid pHR-SHC025-hG4-4PE and the light chain expression plasmid pcDNA3.1(+)-SHC025-hk ofAB06.12-4P.

2. Expression and Purification of Antigen Protein and Positive Control Antibody (1) Construction of Stable Transgenic Cell Line of Antigen Protein CHO-K1 cells (Shanghai Institute of Biochemistry and Cell Biology, Chinese Academy of Sciences) were electrotransfected with eukaryotic expression plasmid pTargeT-CD47 under a square pulse of 15 msec at a voltage of 160V and then cultured in an incubator at 37° C. with 5% $CO_2$. After 24 h, the cells were subjected to selection with culture medium containing 500 μg/ml G418. After 16 days, the positive rate of cell pool was detected by FACS. The cells transfected with plasmid were plated ($1\times10^6$ cells/ml of cell density, 100 μl/well), and incubated with PE mouse anti-human CD47 antibody (BD, 556046). Flow cytometer (BD, FACSJazz) was used to read the mean value at a wavelength of 585 nm, and data analysis was performed using GraphPad.

The positive cell lines were subcloned, and a CHO-K1 cell line was selected, which expressed CD47 at a high level and was named CHO-K1-E5.

(2) Expression of Tagged Antigen Protein and Positive Control Antibody 293F cells were inoculated into a 1L cell culture flask with a density of $0.5\times10^6$ cells/ml. Fresh and pre-warmed FreeStyle 293 expression medium was added to make the total volume 250 mL. The cells were cultured in a humidified $CO_2$ incubator at 37° C. with 8% $CO_2$ overnight. 500 μl of 1 mg/ml PEI solution was added to 8.5 mL FreeStyle 293 expression medium and mixed well. 250 μg of plasmid to be transfected was added to 8.5 ml FreeStyle 293 expression medium and mixed well, wherein, the plasmids encoding tagged antigen, pHR-CD47-hFc, pHR-CD47-his, pcDNA3.1(+)-TPA-CD47-mIgG1-Fc and pcDNA3.1(+)-SIRPα-myc-His, were transfected respectively. The heavy chain plasmid pHR-SHC025-hG4-4PE and the light chain plasmid pcDNA3.1(+)-SHC025-hk of positive control antibody AB06.12-4P were co-transfected. The FreeStyle 293 expression medium containing PEI was added to the expression medium containing plasmids and mixed well, then the mixture was added to the cells, and the cells were cultured in a humidified $CO_2$ incubator at 37° C. with 8% $CO_2$. The cells were fed on the 1st and 3rd day after cell transfection with 2.5 ml of 200 mM glutamine and 5 ml of 180 g/L glucose per flask. The cell culture supernatant was collected when the cell viability dropped to 65%~75%. The cell culture was centrifuged at 1,500 rpm for 5 min to collect the supernatant. The supernatants were centrifuged at 8,000 rpm for 20 min to collect the supernatant again.

(3) Affinity Chromatography Purification

Different affinity chromatography columns were used to perform purification by using AKTA machine (GE, AKTA pure-150) according to the properties of the proteins (see Table 1 for affinity chromatography columns suitable for different proteins). The specific purification steps are as follows.

TABLE 1

Affinity chromatography columns suitable for different proteins

| Protein | Column | Brand | Model |
|---|---|---|---|
| Murine monoclonal antibody (hybridoma)/CD47-mFc | Protein G prepacked column | Bestchrom | Ezfast Protein G 4FF |
| CD47-his/SIRPα-myc-His | NI prepacked column | GE | His Trap, HP 5 ml |
| CD47-hFc/chimeric antibody, humanized antibody | Protein A prepacked column | GE | Hi Trap, Mabselect SuRe 5 ml |
| | Protein A self-packed column | GE | Mabselect LX 18 ml |

Cleaning

The equipment and pipelines were cleaned with ultrapure water for 2 min with a flow rate of 10 mL/min, and then the chromatography system was cleaned with 0.1M NaOH.

Column Connection

The chromatography column was connected to the chromatography equipment and rinsed with ultrapure water for 5 min, and then the chromatography system was rinsed with 0.1M NaOH for 30 min with a retention time of 5 min.

Equilibration

Five CVs (column volume) of 20 mM PB+0.15M NaCl, pH 7.2 was used to equilibrate the column.

Sample Loading

The supernatant from cell culture was loaded to the column with a retention time of 5 min.

Post-Equilibration

Five CVs 20 mM PB+0.15M NaCl, pH 7.2 was used to equilibrate.

Elution

Elution was performed with 50 mM acetic acid (pH=3.4), for a retention time of 5 min. Collection started when UV280 reached about 50 mAu, and stopped when UV280 dropped to about 50 mAu. The sample was adjusted to the pH of 7.0 with 1M Tris-HCl (pH 9.0).

Re-Equilibration

Three CVs of 20 mM PB+0.15M NaCl, pH 7.2, was used to equilibrate with a retention time of 5 min.

On-Column Cleaning

Cleaning was performed with 0.1M NaOH for 30 min with a retention time of 5 min.

Cleaning and Preservation

Cleaning was performed with purified water for 10 minutes, and then 2 CVs of 20% ethanol.

Example 2 Preparation of Anti-CD47 Monoclonal Antibodies

1. Preparation of Hybridomas (1) Animal Immunization

The experimental SJL mice were immunized with different tagged CD47 proteins together with adjuvants. 50 μg of antigen was used for the first shoot, and 25 μg of antigen was used for the subsequent immunization.

The immune adjuvants used in the experiments may be QuickAntibody-Mouse5W (Beijing Biodragon immunotech. Co., Ltd.), TiterMax (Sigma), CpG (GenScript Biotechnology Co., Ltd.), or Alum (thermo) adjuvant. Different tagged CD47 protein samples were added dropwise to the adjuvant solution with vortex to mix thoroughly. The dosages of the adjuvant were referred to the instructions. After the mixture was mixed well and formed a water-in-oil emulsion, the SJL mice were immunized.

Cell lines expressing high level of CD47, such as CCRF-CEM and CHO-K1-E5, were also used to immunize mice to produce antibodies. The cultured human acute lymphoblastic leukemia cells (CCRF-CEM) and CHO-K1-E5 (positive cell line obtained in Example 1) were treated with trypsin and then centrifuged at 1,000 rpm for 5 min. The supernatant was discarded and the cell pellets were resuspended in PBS. Part of the cell sample was taken out for cell counting, and the remaining cell sample was centrifuged at 1,000 rpm for 5 min. The supernatant was discarded and the cell pellet was resuspended in PBS. An appropriate amount of PBS was added to obtain a cell suspension of $1\times10^8$ cells/ml. Each mouse in the experimental group was immunized with $1\times10^7$ cells.

The immunization protocol is shown in Table 2.

TABLE 2

Mouse Immunization Protocol

| Group | Antigen | Adjuvant | Route* |
|---|---|---|---|
| 1 | PBS | None | |
| 2 | CD47-his/CD47-mFc | Quick Antibody-Mouse5W | i.m. |
| 3 | CD47-his/CD47-mFc | Titer Max/CpG/Alum | s.c./i.m. |
| 4 | CD47-mFc | Quick Antibody-Mouse5W | i.m. |
| 5 | CD47-mFc | Titer Max/CpG/Alum | s.c./i.m. |
| 6 | CCRF-CEM/CHO-K1-E5 | None | i.p. |

*i.m.: intramuscular injection; s.c.: subcutaneous injection; i.p.: intraperitoneal injection.

(2) Hybridoma Fusion

Acquisition and preparation of spleen cells. The mice after booster immunization were sacrificed and soaked in 75% alcohol. The spleen was dissected out, ground with a grinding rod, and filtered through a cell strainer to prepare a single cell suspension. The spleen cell suspension was centrifuged at 2,000 rpm for 5 min, and the supernatant was discarded. 2 mL red blood cell lysate was added to lyse red blood cells at room temperature for 2 min and PBS was added to reach 20 mL. After centrifugation at 1,500 rpm for 7 min, the supernatant was discarded. Viable cells were counted after resuspension. The Sp2/0 cells in the culture flask were collected and after centrifuged at 1,000 rpm for 5 min, the supernatant was discarded. Viable cells were counted after resuspension. The spleen cells were mixed with Sp2/0 cells at a ratio of 1:1 and subjected to centrifugation at 1,500 rpm for 7 min, the supernatant was discarded. The cells were resuspended in 20 mL electroporation buffer. After centrifugation at 1,500 rpm for 7 min, the supernatant was discarded and the step was repeated once. The cells were resuspended with an appropriate amount of electroporation buffer to ensure the cell concentration of about $2\times10^7$ cells/mL. The cell suspension was added to a 9 mL electroporation tank for fusion. After fusion, the cell suspension was transferred to 15 mL RPMI 1640 complete medium containing 20% FBS and then left at room temperature for 20 min. The fused cells were resuspended with RPMI 1640 medium containing 1×HAT, 1×BIOMYC3, and 20% FBS. The cell suspension was added to several 96-well cell culture plates at 100 μl/well to ensure that the cell volume per well was about $4\times10^4$ cells/well, and the plates was placed in a 37° C. cell incubator. After 5 days, additional 100 μL of RPMI 1640 complete medium containing 20% FBS, 1×HAT, and 1×BIOMYC-3 was added to each well.

(3) Screening of Hybridoma and Subcloning

After one week of fusion, the supernatants of culture were collected and used for screening the hybridoma supernatants that can bind to CD47-his protein or CD47 on cell surface by ELISA. CD47-his was used to screen for antibodies against CD47 instead of hFc and mFc. The ability of the hybridoma supernatant to block the CD47-SIRPα interaction was analyzed by ELISA. SIRPα-myc-his was coated on ELISA plates. The mixture of recombinant humanized CD47-hFc and hybridoma supernatant was added and incubated for 2 h. HRP-labeled anti-human IgG Fc specific antibody (Jackson Immuno Research) was added and incubated for 1 h. Microplate reader was used to detect absorbance at 450 nm. The hybridoma parent clones showing binding and blocking activities in the screening experiments were expanded. The binding and blocking activities were retested, and the hybridoma positive clones with binding and blocking activities were obtained by screening again.

The positive cell lines were subcloned by the limiting dilution method. After one week of culture, the binding activity to CD47 and the activity of blocking the CD47-SIRPα interaction of the supernatants were detected by ELISA. Three cell lines that showed positive results in the above two tests were obtained, respectively named as SHC025-26, SHC025-34 and SHC025-58.

2. Identification of Antibody Subtypes

The antibody subtypes were identified according to the instructions of the mouse antibody subtype identification kit “SBA Clonotyping Systerm-C57BL/6-HRP” (SouthernBiotech, Cat. No. 5300-05B). The results are shown in Table 3.

TABLE 3

Identification results of antibody subtypes

| Antibody | Antibody subtype |
|---|---|
| SHC025-26 | IgG1/k |
| SHC025-34 | IgG2c/k |
| SHC025-58 | IgG2b/k |

3. Preparation of Monoclonal Antibodies

According to the activity analysis results of the supernatants from cell culture, the parent clones of monoclonal antibodies SHC025-26, SHC025-34, and SHC025-58 were identified and expanded. The culture medium was 1640 medium containing 10% fetal bovine serum, 1×NAEE, 1× sodium pyruvate, and 1% penicillin-streptomycin double antibiotics. When the cell confluence was >80%, the cells were subcultured and expanded. 50 ml of the supernatant was collected and the antibody was purified. The obtained antibody was subjected to SDS-PAGE gel electrophoresis and showed a good purity.

4. Sequencing of Monoclonal Antibodies

The subcloned positive hybridomas were expanded, and an appropriate amount of cells was used for total RNA extraction according to the instructions of RNeasy Plus Mini Kit (Qiagen, 74134). The first strand of cDNA was synthesized using Prime Script 1st strand cDNA Synthesis Kit (Takara, 6110A).

Specific primers were designed according to the variable region of the mouse antibody subtype, and 5' end of the primers contained the homologous arm sequence for homologous recombination with the eukaryotic expression vector. PCR amplification for the variable region of antibodies was performed using cDNA as a template to obtain the gene fragments of the light chain variable region and heavy chain variable region of the mouse antibody respectively. The design of primers refers to references: 1. Anke Krebber, Susanne Bornhauser, Jorg Burmester et al. Reliable cloning of functional antibody variable domains from hybridomas and spleen cell repertoires employing a reengineered phage display system. Journal of Immunological Methods, 1997, 201: 35-55; 2. Simon KorenMiha KosmačAnja Colja Venturini et al. Antibody variable-region sequencing as a method for hybridoma cell-line authentication, 2008, 78: 1071-1078. DNA sequencing was performed and the results are shown in Table 4.

TABLE 4

Sequence table of anti-CD47 murine-derived monoclonal antibody

| Antibody | Amino acid sequence of the heavy chain variable region | Amino acid sequence of the light chain variable region |
|---|---|---|
| SHC025-26 | SEQ ID NO: 21 | SEQ ID NO: 24 |
| SHC025-34 | SEQ ID NO: 22 | SEQ ID NO: 25 |
| SHC025-58 | SEQ ID NO: 23 | SEQ ID NO: 26 |

For the antibody SHC025-34, the CDR sequences of VH: the sequences of CDR1, CDR2 and CDR3 are set forth in SEQ ID NOs: 4, 5 and 6, respectively; the CDR sequences of VL: the sequences of CDR1, CDR2 and CDR3 are set forth in SEQ ID NOs: 15, 16 and 17, respectively.

Example 3 Construction of Anti-CD47 Chimeric Antibodies

The purified gene fragments of the light chain and the heavy chain variable regions of the mouse antibody (see Example 1 for the purification steps) were respectively co-transformed into *Escherichia coli* DH5a competent cells with the linearized eukaryotic expression plasmid containing the light chain constant region or the heavy chain constant region of the human antibody. The mixture was spread evenly on the surface of the agar plates containing the corresponding antibiotics. The agar plates were incubated in a 37° C. constant temperature incubator overnight, and then several single colonies were picked out for DNA sequencing. The chimeric antibodies with correct sequences were named SHC025-26CHI, SHC025-34CHI, and SHC025-58CHI.

The positive clones with correct sequences were inoculated in 2×YT liquid medium containing the corresponding antibiotics and cultured at 37° C. for more than 12 hours with shaking. The bacterial cells were collected for plasmid extraction to obtain the plasmids expressing the light chain and the heavy chain of the chimeric antibody. The concentration and purity of the plasmids were detected by a nucleic acid quantitative analyzer.

The plasmids for chimeric antibodies were transfected into HEK293E cells, and the antibodies were expressed and purified. The purity, activity and affinity were tested and analyzed.

By sequencing, it was found that there was one cysteine in the heavy chain CDR position 118 of SHC025-26 and one cysteine in the light chain CDR position 56 of SHC025-58. During the antibody expression, the cysteine in CDR region would randomly pair with the other cysteine on the antibody molecule to form a disulfide bridge, which thereby would greatly affect the purity of the antibody. To solve this problem, the amino acid sequences of SHC025-26CHI and SHC025-58CHI were modified as follows: C118 of SHC025-26CHI heavy chain was mutated to T and the obtained antibody was named SHC025-26CHI-T; C56 of SHC025-58CHI light chain was mutated to A and the obtained antibody was named SHC025-58CHI-A. The mutant sequences were constructed by site-directed mutagenesis. The results of the chimeric antibody sequencing are shown in Table 5.

TABLE 5

Sequences of anti-CD47 chimeric antibodies

| Chimeric antibody | Amino acid sequence of VH | Amino acid sequence of VL |
|---|---|---|
| SHC025-26CHI | SEQ ID NO: 21 | SEQ ID NO: 24 |
| SHC025-26CHI-T | SEQ ID NO: 27 | SEQ ID NO: 24 |
| SHC025-34CHI | SEQ ID NO: 22 | SEQ ID NO: 25 |
| SHC025-58CHI | SEQ ID NO: 23 | SEQ ID NO: 26 |
| SHC025-58CHI-A | SEQ ID NO: 23 | SEQ ID NO: 28 |

For the antibody SHC025-34CHI: the sequences of CDR1, CDR2 and CDR3 of VH are set forth in SEQ ID NOs: 4, 5 and 6, respectively; the sequences of CDR1, CDR2 and CDR3 of VL are set forth in SEQ ID NOs: 15, 16 and 17, respectively.

Example 4 Construction and Production of Humanized Anti-CD47 Antibodies

Based on the results of activity analysis and affinity KD value of chimeric antibodies, SHC025-34CHI, SHC025-58CHI-A, and SHC025-26CHI-T were modified to humanized antibodies.

To construct the humanized antibodies, the variable regions of SHC025-34CHI, SHC025-58CHI-A, and SHC025-26CHI-T antibody were compared with the mouse antibody sequences in the ImMunoGeneTics (IMGT) to determine their murine-derived germlines. After homology comparison, it was found that the FR region sequences of the heavy chain variable region of SHC025-34CHI, SHC025-58CHI-A, and SHC025-26CHI-T antibody were the most similar to the human antibody germline genes IGHV1-8*01, IGHV3-21*04, and IGHV1-2*02 respectively; the FR sequences of the light chain variable region of the antibodies were the most similar to the human antibody germline genes IGKV3-11*01, IGKV1-5*01 and IGKV4-1*01 respectively. With the framework region sequence FR1-FR3 of SHC025-34CHI/SHC025-58CHI-A antibody as templates, full human framework regions with similar 3D structure but low immunogenicity were screened in the human framework region library to replace FR1-FR3 sequence of SHC025-34CHI/SHC025-58CHI-A. The full-length sequences of the heavy/light chain were 3D modeled and compared structurally with the heavy/light chain sequences of the original antibodies. Considering the antigenicity and 3D structural similarity, 6 humanized heavy chain variable regions (see SEQ ID NOs: 48, 49, 50, 51, 52, and 53) and 4 humanized light chain variable regions (see SEQ ID NOs: 54, 55, 56, and 57) of SHC025-34CHI, and 6 humanized heavy chain variable regions (see SEQ ID NOs: 58, 59, 60, 61, 62, and 63) and 5 humanized light chain variable regions (see SEQ ID NOs: 64, 65, 66, 67, and 68) of SHC025-58CHI-A were ultimately selected for further optimization. More than 95% of non-CDR regions of SHC025-34CHI or SHC025-58CHI-A antibody were humanized. The variable region sequences of the heavy and light chain of SHC025-26CHI-T were used to perform structural alignment analysis in Protein Data Bank. The FR1-FR3 sequences with the highest similarity were selected to replace the murine-derived sequences, and the amino acid sites that displayed key role in structure stabilization of the antibody in the structural simulation were mutated back to murine-derived amino acid residues. Finally, 4 humanized heavy chain variable regions (see SEQ ID NOs: 69, 70, 71, and 72) and 2 humanized light chain variable regions (see SEQ ID NOs: 73 and 74) of SHC025-26CHI-T were obtained.

The amino acid sequences of the light chain and heavy chain variable region of humanized antibody obtained above were reversely transcribed into their corresponding nucleotide sequences, and oligonucleotide fragments containing complementary sequences between adjacent fragments were generated. The oligonucleotide fragments were annealed and assembled by Overlap PCR. Then nucleotide fragments of the entire light chain and heavy chain variable regions were amplified using specific primers (5' end contained the homologous arm sequence for homologous recombination with the eukaryotic expression vector). The purified nucleotide fragments of the light chain variable region were co-transformed into *Escherichia coli* DH5a competent cells with the linearized eukaryotic expression plasmid containing light chain constant region of IgG4. The purified nucleotide fragments of the heavy chain variable region were co-transformed into *Escherichia coli* DH5a competent cells with the eukaryotic expression plasmid containing heavy chain constant region of IgG4 containing S228P/L235E mutation. The competent cells with the transformed plasmid were spread evenly on the surface of the agar plates containing the corresponding antibiotics. The agar plates were incubated in a 37° C. constant temperature incubator overnight, and then several single colonies were picked out for DNA sequencing.

The positive clones with correct sequences were inoculated in 2×YT liquid medium containing the corresponding antibiotics and cultured at 37° C. with shaking for more than 12 hours. The bacterial cells were collected for plasmid extraction to obtain the expression plasmids for the light chain and the heavy chain of humanized antibodies. The concentration and purity of the plasmids were detected by a nucleic acid quantitative analyzer.

The plasmids were transfected into HEK293E cells, and a large number of antibodies were expressed and purified. The purity, activity and affinity were tested and analyzed.

The humanized antibodies with good purity, activity and affinity were selected, and named as Hu26T-31-PE, Hu34-39-PE, and Hu58A-14-PE. The sequences are shown in Table 6. The sources of humanized antibodies are shown in Table 7.

TABLE 6

Sequence table of humanized anti-CD47 antibodies

| Humanized | Amino acid sequence | | Nucleotide sequence | |
|---|---|---|---|---|
| antibody | VH | VL | VH | VL |
| Hu26T-31-PE | SEQ ID NO: 29 | SEQ ID NO: 32 | SEQ ID NO: 35 | SEQ ID NO: 38 |
| Hu34-39-PE | SEQ ID NO: 30 | SEQ ID NO: 33 | SEQ ID NO: 36 | SEQ ID NO: 39 |
| Hu58A-14-PE | SEQ ID NO: 31 | SEQ ID NO: 34 | SEQ ID NO: 37 | SEQ ID NO: 40 |

For the antibody Hu34-39-PE, the sequences of CDR1, CDR2 and CDR3 of VH are set forth in SEQ ID NOs: 4, 5 and 6, respectively; the sequences of CDR1, CDR2 and CDR3 of VL are set forth in SEQ ID NOs: 15, 16 and 17, respectively.

TABLE 7

Information of humanized sequences

| Source of humanized sequence | Recombinant humanized sequence |
|---|---|
| Heavy chain | |
| X62106 Homsap IGHV1-2*02 F | SEQ ID NO: 29 |
| X92343 Homsap IGHV1-46*01 F | SEQ ID NO: 30 |
| HM855688 Homsap IGHV3-21*04 F | SEQ ID NO: 31 |
| Light chain | |
| X97473 Homsap IGLV3-9*01 F | SEQ ID NO: 32 |
| X71966 Homsap IGLV3-21*01 F | SEQ ID NO: 33 |
| Z73648 Homsap IGLV4-69*01 F | SEQ ID NO: 34 |

Example 5 Binding Activity Assay of Anti-CD47 Antibodies to Monkey CD47 (by ELISA)

The binding activity of antibodies was analyzed by protein based ELISA. Cynomolgus CD47-His (0.1 μg/well, ACRO Biosystems, Cat. No. CD7-C52H1-50 μg) was coated on 96-well ELISA plates. The anti-CD47 antibodies of the present disclosure was used as the primary antibody and added to the ELISA plates in 5-fold gradient dilution with a total of 8 concentrations: 2000 ng/mL, 400 ng/mL, 80 ng/mL, 16 ng/mL, 3.2 ng/mL, 0.64 ng/mL, 0.128 ng/mL, and 0 ng/mL respectively. The plates were incubated at 37° C. for 1.5h. AB06.12-4P was used as the positive control antibody and Anti-Human IgG HRP (Jackson, 109-035-003, 1:10000) was used as the secondary antibody. Color developing solution TMB (3,3',5,5'-tetramethylbenzidine) was added to the plate, and microplate reader (Thermo, Multiskan FC) was used to read OD450 value after termination of the reaction. $EC_{50}$ was generated by GraphPad. The result is shown in FIG. 1.

The experimental results show that humanized anti-CD47 antibodies Hu26T-31-PE, Hu34-39-PE and Hu58A-14-PE of the present disclosure can bind to cynomolgus CD47, and the binding ability is equivalent to that of the positive control antibody AB06.12-4P.

Example 6 Binding Activity Assay of Anti-CD47 Antibodies to Human CD47 (by ELISA)

Figure 2:
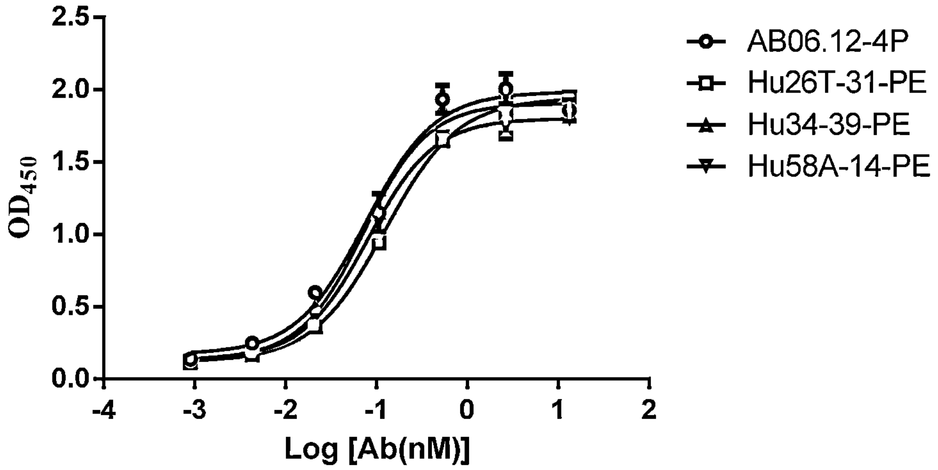
FIG. 2 shows the results of the binding activity assay (ELISA) of the humanized anti-CD47 antibodies to human CD47.

The binding activity of antibodies was analyzed by ELISA. Human CD47-His protein (0.1 μg/well, prepared in Examples 1 and 2) was coated on 96-well ELISA plates, and the ELISA plates were incubated at 37° C. for 2 h. After washing 3 times with 1×PBST, the ELISA plates were blocked with 5% non-fat milk at 4° C. overnight. The plates were washed 3 times with 1×PBST. The anti-CD47 antibodies of the present disclosure were used as the primary antibody and added to the ELISA plates at 5-fold gradient dilution with a total of 8 concentrations: 2000 ng/mL, 400 ng/mL, 80 ng/mL, 16 ng/mL, 3.2 ng/mL, 0.64 ng/mL, 0.128 ng/mL, and 0 ng/mL respectively. The plates were incubated at 37° C. for 1.5h. The plates were washed 3 times with 1×PBST. AB06.12-4P was used as the positive control antibody and Anti-Human IgG HRP (Jackson, 109-035-003, 1:10000) was used as the secondary antibody. Then the plates were incubated at 37° C. for 40 min. Color developing solution TMB was added after the plates were washed 5 times with 1×PBST, and microplate reader (Thermo, Multiskan FC) was used to read OD450 value after termination of the reaction. $EC_{50}$ was generated by GraphPad. The result is shown in FIG. 2.

The experimental results show that humanized anti-CD47 antibodies Hu26T-31-PE, Hu34-39-PE and Hu58A-14-PE of the present disclosure can bind to human CD47, and the binding ability is equivalent to that of the positive control antibody AB06.12-4P.

Example 7 Binding Activity Assay of Anti-CD47 Antibodies to CD47 on Cell Surface (by ELISA)

Figure 3:
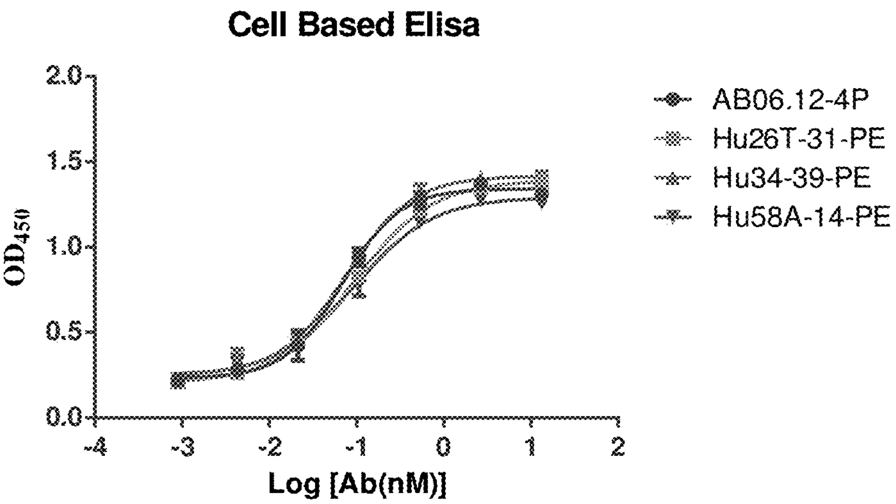
FIG. 3 shows the results of the binding activity assay (ELISA) of the humanized anti-CD47 antibodies to CD47 on cell surface.

The binding activity of antibodies was analyzed by cell based ELISA. CHO-K1-E5 cells were plated at $1\times10^5$ cells per well and cultured overnight at 37° C. and 5% $CO_2$. On the second day, the cells were fixed with 4% paraformaldehyde, then blocked with non-fat milk for 1 h, and later washed gently with 1×PBS. The anti-CD47 antibody of the present disclosure was used as the primary antibody and added to the plates in 5-fold gradient dilution with a total of 8 concentrations: 2000 ng/mL, 400 ng/mL, 80 ng/mL, 16 ng/mL, 3.2 ng/mL, 0.64 ng/mL, 0.128 ng/mL, and 0 ng/mL respectively. The plates were incubated at 37° C. for 1.5h. AB06.12-4P was used as the positive control antibody and Anti-Human IgG HRP (Jackson, 109-035-003, 1:10,000) was used as the secondary antibody. Color developing solution TMB was added, and microplate reader (Thermo, Multiskan FC) was used to read OD450 value after termination. $EC_{50}$ was generated by GraphPad. The result is shown in FIG. 3.

The experimental results show that humanized anti-CD47 antibodies Hu26T-31-PE, Hu34-39-PE and Hu58A-14-PE of the present disclosure can bind to CD47 on cell surface, and the binding ability is equivalent to that of the positive control antibody AB06.12-4P.

Example 8 Affinity Assay of Anti-CD47 Antibodies to Human CD47 Protein

The affinity of the humanized anti-CD47 antibodies prepared in Examples 1 and 2 to the antigen CD47(19-136)- hFC was determined by Fortebio Octet. First, the antigen CD47(19-136)-hFc was labeled with biotin, and then put into 10 kD cut-off ultrafiltration tube with PBS for desalting by centrifugation. This step was repeated 3-4 times. The actual concentration of the biotin-labeled antigen (CD47-hFc-Biotin) was determined by Nanodrop machine. CD47-hFc-Biotin was diluted with SD buffer (0.02% Tween20+0.1% BSA solution) to a concentration of 5 μg/ml. The humanized anti-CD47 antibody was diluted with SD buffer in 4-fold gradient dilution to make the concentrations of 10 μg/ml, 2.5 μg/ml, 0.625 μg/ml and 0 μg/ml. SA sensor was used to solidify the antigen, and affinity assay was performed according to the manual of fortebio Octet RED96. The specific parameters and experimental results are shown in Table 8.

TABLE 8

Affinity assay of antibodies to human CD47 protein

| Antibody | KD (M) | kon (l/Ms) | kdis (1/s) |
|---|---|---|---|
| Hu26T-31-PE | 5.87E−11** | 1.04E+06 | 6.13E−05 |
| Hu34-39-PE | 1.13E−10 | 6.69E+06 | 7.58E−04 |
| Hu58A-14-PE | 9.46E−11 | 1.78E+06 | 1.68E−04 |
| AB06.12-4P | 1.01E−10 | 4.80E+06 | 4.85E−04 |

The experimental results show that the humanized anti-CD47 antibody Hu26T-31-PE has significantly higher affinity for binding to human CD47 protein than the positive control antibody.

Figure 4:
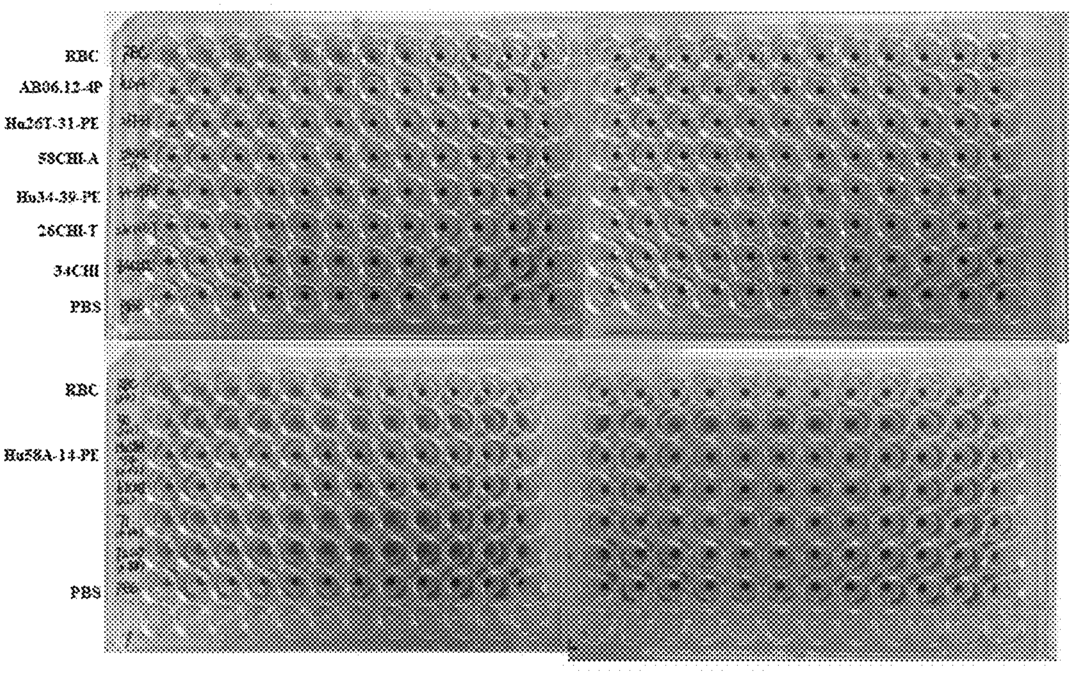
FIG. 4 shows the results of the hemagglutination test, wherein RBC represents the positive control and PBS represents the blank control.

Example 9 Hemagglutination Test of Anti-CD47 Antibodies 5 mL blood sample was added to 40 mL PBS. The mixture was centrifuged at 2000 rpm for 5 min and the supernatant was discarded. The cell pellet was washed three times with PBS and then resuspended in PBS. According to the hematocrit, a 2% red blood cell suspension was prepared. The initial concentration of the antibody to be analyzed was 1-20 μM at a 2-fold dilution, a total of 24 concentration gradients. In round-bottom 96-well plates, 50 μL of the above-mentioned antibodies of different concentrations was added, and then 50 ul of the 2% red blood cell suspension was added. The mixture was mixed well, placed at room temperature and monitored for agglutination after 2h. Rabbit polyclonal RBC antibody (Rockland, 109-4139) was used as a positive control for hemagglutination and the results are shown in FIG. 4. As shown in FIG. 4, the concentration of the antibodies (rabbit polyclonal RBC antibody, AB06.12-4P antibody and the test antibodies of the present disclosure) from left to right in the 96-well plates were diluted in a 2-fold gradient starting from 20 uM. RBC indicated the positive control group, in which rabbit polyclonal RBC antibody caused significant hemagglutination), and PBS indicated the blank control group. If there is no cell agglutination, the red blood cells will fall to the bottom of the well as a small dot with smooth edge. Dot with slightly vague edge indicates agglutination of a small amount of red blood cells. If the red blood cells form flaky shape and cover the whole bottom of the well, this indicates agglutination of most of the red blood cells.

It has been reported that the anti-CD47 antibody Hu5F9-G4 disclosed in the patent application WO2011/143624 can cause significant agglutination of red blood cells within the same concentration range, which is a common undesirable property of anti-CD47 antibodies. However, under the same conditions, Hu26T-31-PE, Hu34-39-PE, and Hu58A-14-PE of the present disclosure did not cause hemagglutination as shown in the experimental results, indicating that the antibodies of the present disclosure are significantly superior to the Hu5F9-G4 antibody in this respect.

Example 10 Blocking Activity Assay of Anti-CD47 Antibodies Against CD47

The ability of the anti-CD47 antibody provided by the present disclosure to block SIRPα from binding to CD47 on cell surface was detected by FACS.

Figure 5:
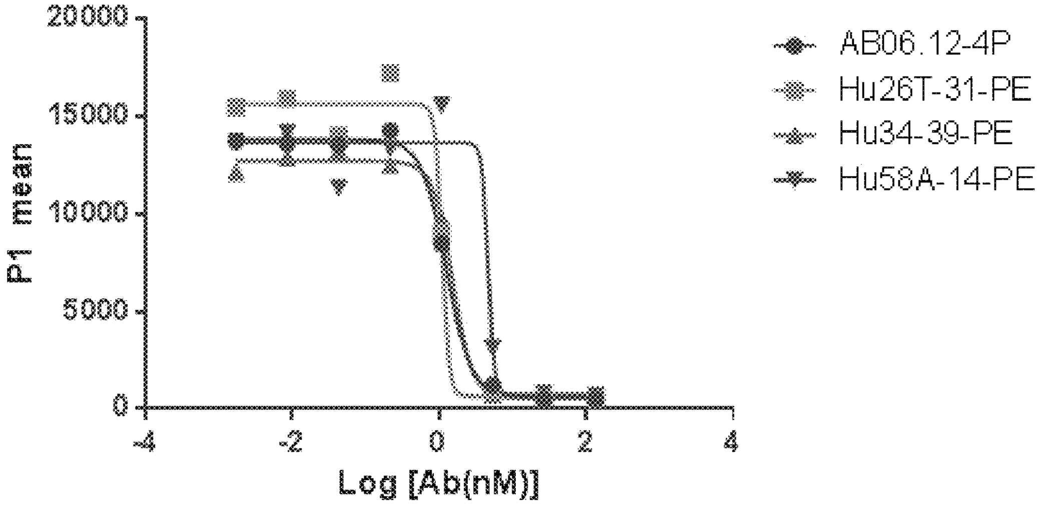
FIG. 5 shows the results of the blocking activity of the humanized anti-CD47 antibodies detected by FACS.

CHO-K1-E5 cells positive for CD47 were used as a CD47 provider. In the presence of a serially diluted anti-CD47 antibody, the binding of CD47 to SIRPα was monitored. PE Streptavidin (Biolegend, 405203, 1:200) was used as the secondary antibody to monitor the changes of SIRPα-Biotin, and AB06.12-4P was used as a positive control which blocked SIRPα from binding to CD47 on cell surface. Flow cytometer (BD, FACSJazz) was used to read the mean value at a wavelength of 585 nm and $IC_{50}$ was generated by GraphPad. The result is shown in FIG. 5.

The experimental results show that the blocking activity ranking from high to low is: Hu26T-31-PE≥Hu34-39-PE≥AB06.12-P≥Hu58A-14-PE.

Example 11 Anti-Tumor Test of Anti-CD47 Antibodies in Human Gastric Cancer NUGC-4 Xenograft Model 1. Experimental Materials (1) Experimental Cells and Animals NUGC-4 human gastric cancer cells were purchased from American Type Culture Collection (ATCC).

NOD-Scid mice, female, 5-8 weeks old, weighing 18-20 grams, were purchased from Shanghai Lingchang Biotechnology Co., Ltd.

(2) Test Samples and Controls

The reference antibody isotype IgG4 (Cat. No. AB170091) was purchased from Crown Bioscience Co., Ltd. and used as a negative control.

Before the test, the humanized anti-CD47 antibody of the present disclosure was prepared at two concentrations of 0.6 mg/mL and 0.3 mg/mL in PBS, and Isotype IgG4 and AB 06.12-4P were prepared at 0.6 mg/mL.

(3) Experimental Methods

NUGC-4 human gastric cancer cells were cultured with RMPI1640 medium containing 10% fetal bovine serum, 100 U/mL penicillin and 100 μg/mL streptomycin in a 37° C., 5% $CO_2$ incubator. The cells were digested, treated with 2 mL 1×EDTA solution and passaged once a week. When the cell confluence reached 80%-90%, the cells were collected, counted, and seeded. PBS containing $5\times10^6$ cells was mixed with 100 uL Matrigel (final volume of 200 μL). The mouse was injected with the mixture on the right back side, $5\times10^6$ cells/mouse. The mice were grouped when the tumor grew to a volume of 150-200 $mm^3$ and administered intraperitoneally with the test sample three times per week. The tumor diameter was measured with a vernier caliper three times per week and the tumor volume was calculated by a calculation equation of $V=0.5a\times b^2$, where a and b represent the long and short diameters of the tumor, respectively. The anti-tumor efficacy of antibodies was evaluated by the relative tumor growth rate T/C (%). The calculation equation of the relative tumor growth rate T/C (%) is as follows: T/C %=TRTV/

CRTV×100% (TRTV: treatment group RTV; CRTV: negative control group RTV). RTV=V21/VO, where VO is the tumor volume measured at the time of being grouped and administered (Day 0), and V21 is the tumor volume measured at the 21th day of administration (Day 21). The tumor volumes on the last day (Day 21) of the administration group and the vehicle group were analyzed by t-test using GraphPad Prism. The results are shown in Table 9.

TABLE 9

Anti-tumor test results in human gastric cancer NUGC-4 xenograft model

| Antibody | Dose (mg/kg) | T/C (%) | p (vs. Isotype IgG4) |
|---|---|---|---|
| Isotype IgG4 | 6 | 86.61 | — |
| AB06.12-4P | 6 | 18.82 | ** |
| Hu26T-31-PE | 3 | 12.24 | *** |
| Hu26T-31-PE | 6 | 2.96 | *** |
| Hu34-39-PE | 3 | 15.29 | *** |
| Hu34-39-PE | 6 | 3.45 | *** |

Comparing with Isotype IgG4, *indicates $p < 0.001$; indicates $p < 0.005$.

Figure 6:
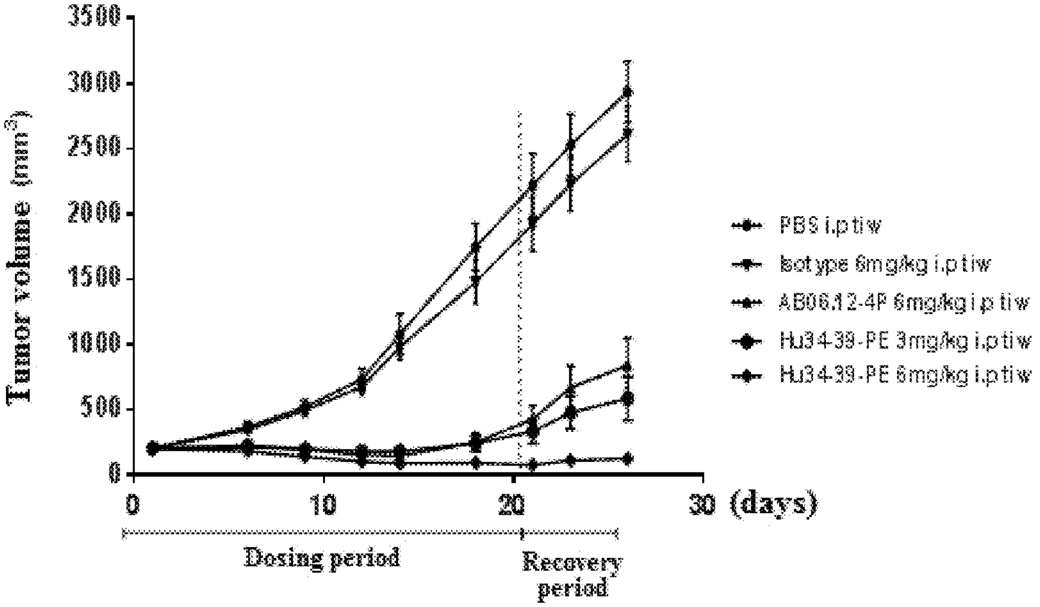
FIG. 6 shows the results of the anti-tumor test of the humanized anti-CD47 antibody Hu34-39-PE in human gastric cancer NUGC-4 xenograft model.
Figure 7:
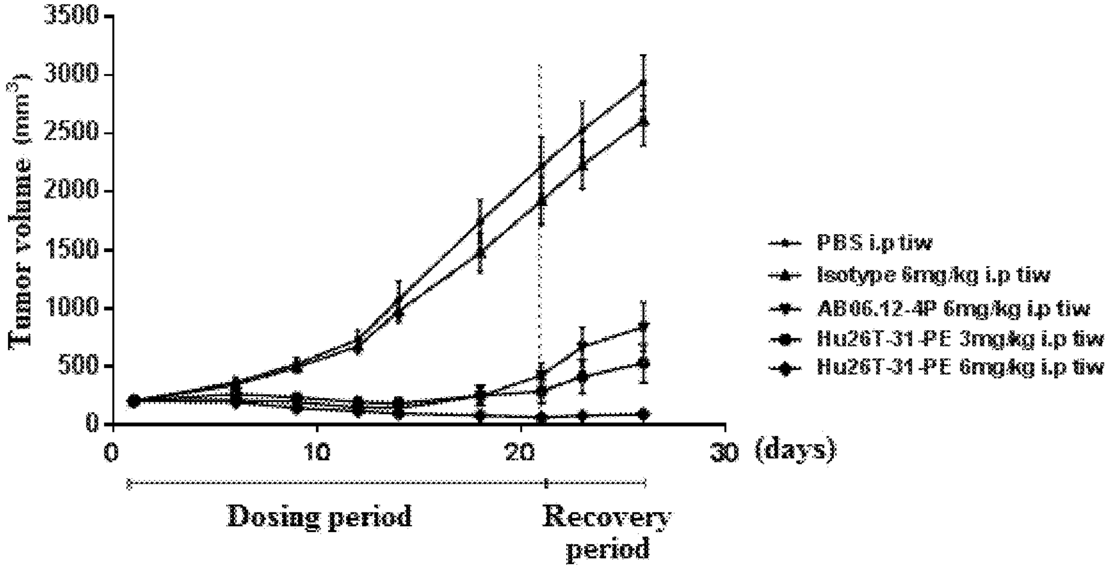
FIG. 7 shows the results of the anti-tumor test of the humanized anti-CD47 antibody Hu26T-31-PE in human gastric cancer NUGC-4 xenograft model.

The experimental results show that the antibodies of the present disclosure have a significant anti-tumor effect in NOD-SCID mice xenograft model inoculated with human gastric cancer NUGC-4 cells. Hu26T-31-PE and Hu34-39-PE at a dose of 3 mg/kg show equivalent tumor-suppressive effect as the reference antibody AB06.12-4P at a dose of 6 mg/kg, while Hu26T-31-PE and Hu34-39-PE at a dose of 6 mg/kg show a better tumor-suppressive effect than the reference antibody AB06.12-4P at a dose of 6 mg/kg. One week after drug withdrawal, tumor recurrence occurred in the group of reference antibody at a dose of 6 mg/kg, while no recurrence occurred in the group of Hu26T-31-PE or Hu34-39-PE (FIG. 6 and FIG. 7). It indicates that the anti-CD47 antibodies of the present disclosure have unexpectedly better effect on inhibiting tumor growth.

Example 12 Production of Anti-Human PD-L1 Antibodies

1. Animal Immunization

Experimental BALB/c and SJL mice and SD rats were immunized with mFc-tagged PD-L1 antigen protein (purchased from ACROBiosystems, Beijing) together with adjuvants.

The immune adjuvant was Freund's Adjuvant, Complete (SIGMA, F5881-10ML) for the first time, and Freund's Adjuvant, Incomplete (SIGMA, F5506-10ML) for the later stages. Different tagged PD-L1 protein samples were added dropwise to the adjuvant solution with vortex to mix thoroughly. The dosages of the adjuvant were referred to the instructions. After the mixture was mixed well to form a water-in-oil emulsion, mice or rats were immunized. The immunization protocol is shown in Table 10.

TABLE 10

Immunization protocol

| Group | Strain | Antigen | Adjuvant | Dose | Route* |
|---|---|---|---|---|---|
| 1 | BALB/c | PBS | None | | |
| 2 | BALB/c | PD-L1-mFc | Freund's Adjuvant, Complete (First time) | 50 μg | i.m. |
| | | | Freund's Adjuvant, Inomplete | 25 μg | |
| 3 | SJL | PBS | None | | |
| 4 | SJL | PD-L1-mFc | Freund's Adjuvant, Complete (First time) | 50 μg | i.m. |
| | | | Freund's Adjuvant, Inomplete | 25 μg | |
| 5 | SD | PBS | None | | |
| 6 | SD | PD-L1-mFc | Freund's Adjuvant, Complete (First time) | 100 μg | i.m. |
| | | | Freund's Adjuvant, Inomplete | 50 μg | |

*i.m.: intramuscular injection

2. Cell Fusion

The mouse spleen was aseptically removed and prepared into a cell suspension, and the cells were fused at the ratio of spleen cells: Sp2/0 cells=1:1. The fused cell suspension was transferred to 15 mL RPMI 1640 complete medium containing 20% FBS and then left at room temperature for 20 min. The fused cells were resuspended with RPMI 1640 medium containing 1×HAT, 1×BIOMYC3, and 20% FBS. The cell suspension was added to several 96-well cell culture plates at 100 μl/well to ensure that the cell volume per well was about $4\times10^4$ cells/well, and the plates was placed in a 37° C. cell incubator. After 5 days, additional 100 μL of RPMI 1640 complete medium containing 20% FBS, 1×HAT, and 1×BIOMYC-3 was added to each well.

3. Screening of Positive Clones

After one week of fusion, the cell supernatant was collected. The hybridoma parent clones with binding and blocking abilities were screened by ELISA, expanded, tested for binding and blocking activities, and screened again for hybridoma positive cell lines with binding and blocking abilities. The positive cell lines were subcloned by the limiting dilution method, and after one week of culture, the activities of binding to PD-L1 molecules and blocking the interaction of PD-L1/PD-1 of the supernatant were detected by ELISA. Four preferable cell strains that showed positive results in the above two tests, PL-7, The PL-15, PL-16 and PL-18, were selected.

4. Acquisition of Variable Region Sequences of Anti-PD-L1 Antibodies

The subcloned positive hybridoma cells were expanded, and an appropriate amount of cells was used for total RNA extraction according to the instructions of RNeasy Plus Mini Kit (Qiagen, 74134). The first strand of cDNA was synthesized using Prime Script 1st strand cDNA Synthesis Kit (Takara, 6110A).

Specific primers were designed according to the variable region of the mouse antibody subtype, and 5' end of the primers contained the homologous arm sequence for homologous recombination with the eukaryotic expression vector. PCR amplification for the variable region of antibodies was performed using cDNA as a template to obtain the gene fragments of the light chain variable region and heavy chain variable region of the mouse antibody, named SHS009PL-7, SHS009PL-15, SHS009PL-16 and SHS009PL-18, respectively. The design of primers refers to references: Anke Krebber, Susanne Bornhauser, Jorg Burmester et al. Reliable cloning of functional antibody variable domains from hybridomas and spleen cell repertoires employing a reengineered phage display system. Journal of Immunological Methods, 1997, 201: 35-55; 2. Simon KorenMihaKosmačAnjaColjaVenturinietal. Antibody variable-region sequencing as a method for hybridoma cell-line authentication, 2008, 78: 1071-1078. DNA sequencing was performed and the results are shown in Table 11.

TABLE 11

Sequence table of anti-PD-L1 murine-derived monoclonal antibody

| Antibody | Amino acid sequence of VH | Amino acid sequence of VL | H2CDR1/ H2CDR2/ H2CDR3 | L2CDR1/ L2CDR2/ L2CDR3 |
|---|---|---|---|---|
| SHS009PL-7 | SEQ ID NO: 99 | SEQ ID NO: 103 | SEQ ID NOs: 75, 76 and 77 | SEQ ID NOs: 78, 79 and 80 |
| SHS009PL-15 | SEQ ID NO: 100 | SEQ ID NO: 104 | SEQ ID NOs: 81, 82 and 83 | SEQ ID NOs: 84, 85 and 86 |
| SHS009PL-16 | SEQ ID NO: 101 | SEQ ID NO: 105 | SEQ ID NOs: 87, 88 and 89 | SEQ ID NOs: 90, 91 and 92 |
| SHS009PL-18 | SEQ ID NO: 102 | SEQ ID NO: 106 | SEQ ID NOs: 93, 94 and 95 | SEQ ID NOs: 96, 97 and 98 |

5. Construction of Chimeric Antibodies

The purified gene fragments of the light chain and the heavy chain variable regions of the mouse antibodies were respectively co-transformed into *Escherichia coli* DH5a competent cells with the linearized eukaryotic expression plasmid containing the light chain constant region or the heavy chain constant region of human antibodies. The chimeric antibodies with correct sequences were selected and named PL-7CHI, PL-15CHI, PL-16CHI and PL-18CHI. The sequencing results of the chimeric antibodies are shown in Table 12.

The amino acid sequences of VL and VH of PL-7CHI, PL-15CHI, PL-16CHI and PL-18CHI are identical to those of the murine-derived antibodies SHS009PL-7, SHS009PL-15, SHS009PL-16 and SHS009PL-18, respectively.

The plasmids for light and heavy chains of chimeric antibodies were transfected into HEK 293F cells, and the antibodies were expressed and purified. The purity, activity and affinity were tested and analyzed.

TABLE 12

Sequence table of anti-PD-L1 chimeric antibodies

| Chimeric antibody | Amino acid sequence of VH | Amino acid sequence of VL |
|---|---|---|
| PL-7CHI | SEQ ID NO: 99 | SEQ ID NO: 103 |
| PL-15CHI | SEQ ID NO: 100 | SEQ ID NO: 104 |
| PL-16CHI | SEQ ID NO: 101 | SEQ ID NO: 105 |
| PL-18CHI | SEQ ID NO: 102 | SEQ ID NO: 106 |

6. Humanization of Anti-PD-L1 Antibodies

Based on the results of activity analysis and affinity KD value of chimeric antibodies, PL-7CHI and PL-16CHI were modified to humanized antibodies.

The humanization of murine-derived monoclonal chimeric antibodies PL-7CHI and PL-16CHI was carried out with reference to the classical CDR transplantation strategy. With the framework region sequence FR1-FR3 of antibodies PL-7CHI and PL-16CHI as templates, full human framework regions with similar 3D structure but low immunogenicity were screened in the human framework region library to replace FR1-FR3 sequence of PL-7CHI and PL-16CHI. After homology comparison, it was found that the FR region sequences of the heavy chain variable region of the antibodies PL-7CHI and PL-16CHI were the most similar to the human antibody germline genes M99683|IGHV4-31*02 (SEQ ID NO: 107) and X62109|IGHV1-3*01 (SEQ ID NO: 108), respectively; the FR region sequences of the light chain variable region of the antibodies PL-7CHI and PL-16CHI were the most similar to the human antibody germline gene Z00023|IGKV4-1*01 (SEQ ID NO: 109). The full-length sequences of the humanized heavy/light chain were 3D modeled and compared structurally with the heavy/light chain sequences of the original antibodies. The antigenicity and 3D structural similarity were considered comprehensively, and the amino acids that were shown to play a key role in the structural stability of the antibody in the structural simulation were back mutated to murine amino acid residues. Finally, 5 humanized heavy chains (the humanized heavy chain variable region sequences of PL-7CHI: VH1-0 (SEQ ID NO: 110), VH1-1 (SEQ ID NO: 111), VH1-2 (SEQ ID NO: 112), VH1-3 (SEQ ID NO: 113) or VH1-4 (SEQ ID NO: 114)) and 4 humanized light chains (the humanized light chain variable region sequences of PL-7CHI: VL1-0 (SEQ ID NO:115), VL1-1 (SEQ ID NO:116), VL1-2 (SEQ ID NO:117) or VL1-3 (SEQ ID NO:118)) of PL-7CHI were obtained; and 5 humanized heavy chains (the humanized heavy chain variable region sequences of PL-16CHI: VH1-0 (SEQ ID NO: 119), VH1-1 (SEQ ID NO: 120), VH1-2 (SEQ ID NO: 121), VH1-3 (SEQ ID NO: 122) or VH1-4 (SEQ ID NO: 123)) and 3 humanized light chains (the humanized light chain variable region sequences of PL-16CHI: VL1-0 (SEQ ID NO: 124), VL1-1 (SEQ ID NO: 125) or VL1-2 (SEQ ID NO: 126)) of PL-16CHI were obtained.

On this basis, multiple humanized antibodies were obtained through different combinations of light and heavy chains. After activity detection, it was determined that the anti-PD-L1 humanized antibodies with the highest scores were HuPL7-21 and HuPL16-42.

Example 13 Production of Humanized Anti-PD-L1 Antibodies

Corresponding polynucleotides were synthesized based on the amino acid sequences of the light chain and heavy chain variable region of humanized antibody obtained above, and oligonucleotide fragments containing complementary sequences between adjacent fragments were synthesized. The oligonucleotide fragments were annealed and assembled by Overlap PCR. Then nucleotide fragments encoding the entire light chain and heavy chain variable regions were amplified by specific primers (5' end contained the homologous arm sequence for homologous recombination with the eukaryotic expression vector). The purified nucleotide fragments of the light chain variable region were co-transformed into *Escherichia coli* DH5a competent cells with the linearized eukaryotic expression plasmid containing light chain constant region of IgG4. The purified nucleotide fragments of the heavy chain variable region were co-transformed into *Escherichia coli* DH5a competent cells with the eukaryotic expression plasmid containing heavy chain constant region of IgG4 containing S228P/L235E mutation. The competent cells with the transformed plasmids were spread evenly on the surface of the agar plates containing the corresponding antibiotics. The agar plates were incubated in a 37° C. constant temperature incubator overnight, and then several single colonies were picked out for DNA sequencing.

The positive clones with correct sequences were subjected to plasmid extraction to obtain the expression plasmids for the light chain and the heavy chain of humanized antibodies. The concentration and purity of the plasmids were detected by a nucleic acid quantitative analyzer.

The plasmids were transfected into HEK293 F cells, and a large number of antibodies were expressed and purified. The purity, activity and affinity were tested and analyzed. The sequences are shown in Table 13.

TABLE 13

Sequence table of anti-PD-L1 humanized antibodies

| Humanized | Amino acid sequence | | Nucleotide sequence | |
|---|---|---|---|---|
| antibody | VH | VL | VH | VL |
| HuPL7-21 | SEQ ID NO: 112 | SEQ ID NO: 116 | SEQ ID NO: 127 | SEQ ID NO: 129 |
| HuPL16-42 | SEQ ID NO: 123 | SEQ ID NO: 126 | SEQ ID NO: 128 | SEQ ID NO: 130 |

For the antibody HuPL7-21, the sequences of CDR1, CDR2 and CDR3 of VH are set forth in SEQ ID NOs: 75, 76 and 77, respectively; the sequences of CDR1, CDR2 and CDR3 of VL are set forth in SEQ ID NOs: 78 and 79 and 80, respectively. For the antibody HuPL16-42, the sequences of CDR1, CDR2 and CDR3 of VH are set forth in SEQ ID NOs: 87, 88 and 89, respectively; the sequences of CDR1, CDR2 and CDR3 of VL are set forth in SEQ ID NOs: 90, 91 and 92, respectively.

Figure 8:
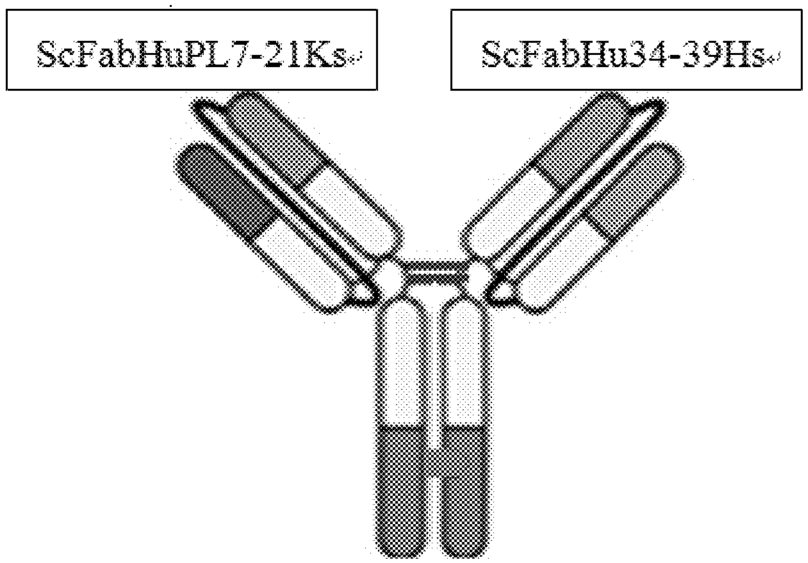
FIG. 8 shows a schematic diagram of the structure of bispecific antibody ScFab (HuPL7-21Ks/Hu34-39Hs).

Example 14 Construction, Expression and Purification of Anti-CD47/PD-L1 Bispecific Antibodies 1. Construction of Expression Vector for Bispecific Anti-CD47/Anti-PD-L1 Antibodies The anti-CD47/anti-PD-L1 bispecific antibodies were constructed by genetic engineering, and the structure of antibodies is shown in FIG. 8. The bispecific antibody is formed by heterodimerization of two single chains from anti-PD-L1 antibody and anti-CD47 antibody, respectively. Unlike the natural IgG antibody, the light chains of both anti-PD-L1 and anti-CD47 antibodies in this bispecific antibody are linked to the N-terminal of the heavy chain by an additional flexible linking peptide, which is a GGGGS repeat sequence containing glycine (G) and serine (S) residues, preferably a sequence containing eight GGGGS repeats. In addition, in order to promote the formation of heterodimers, the S354C/T366W mutation is further added to the CH3 domain of the anti-PD-L1 antibody single chain and the Y349C/T366S/L368A/Y407V mutation to the CH3 domain of the anti-CD47 antibody single chain on the basis of the above S228P/L235E mutation. According to this structural form, the sequences of the above-mentioned anti-PD-L1 antibody HuPL7-21 (light chain variable region set forth in SEQ ID NO: 116 and constant region CL set forth in SEQ ID NO: 131) or HuPL16-42 (light chain variable region set forth in SEQ ID NO: 126 and constant region CL set forth in SEQ ID NO: 131) were used to obtain the nucleotide fragment of the anti-PD-L1 antibody single chain by gene synthesis, namely ScFabHuPL7-21Ks or ScFabHuPL16-42Ks. The sequences of the above-mentioned anti-CD47 antibody Hu34-39 (light chain variable region set forth in SEQ ID NO: 33 and constant region CL set forth in SEQ ID NO: 131) were used to obtain the nucleotide fragment of the anti-CD47 antibody single chain by gene synthesis, namely ScFabHu34-39Hs. The nucleotide fragments ScFabHuPL7-21Ks (or ScFabHuPL16-42Ks) and ScFabHu34-39Hs (upstream and downstream containing homology arms of appropriate length) were respectively co-transformed into *Escherichia coli* DH5a competent cells with the linearized eukaryotic expression plasmid pHR. The competent cells transformed with the plasmids were spread evenly on the surface of the agar plates containing the corresponding antibiotics. The agar plates were incubated in a 37° C. constant temperature incubator overnight, and then several single colonies were picked out for DNA sequencing. The positive clones with correct sequence were subjected to plasmid extraction to obtain ScFabHuPL7-21Ks (or ScFabHuPL16-42Ks) and ScFabHu34-39Hs expression vectors.

Figure 9:
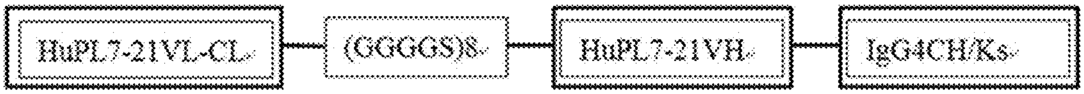
FIG. 9 shows a schematic diagram of the sequence of ScFabHuPL7-21Ks.

FIG. 9 shows a schematic diagram of the sequence structure of ScFabHuPL7-21Ks, wherein HuPL7-21VL-CL represents humanized PD-L1 monoclonal antibody HuPL7-21 light chain; $(GGGGS)_8$ represents a flexible linking peptide of 8 GGGGS repeats; HuPL7-21VH represents humanized PD-L1 monoclonal antibody HuPL7-21 heavy chain variable region; IgG4CH/Ks represents IgG4 heavy chain constant region (specific sequence set forth in, for example, SEQ ID NO: 132) containing S228P/L235E/S354C/T366W mutation to form a "Knob" structure.

Figure 10:
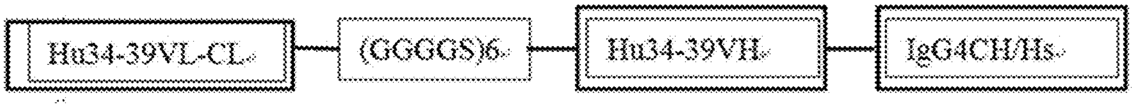
FIG. 10 shows a schematic diagram of the sequence of ScFabHu34-39Hs.

FIG. 10 shows a schematic diagram of the sequence structure of ScFabHu34-39Hs, wherein Hu34-39VL-CL represents humanized CD47 monoclonal antibody Hu34-39 light chain; $(GGGGS)_6$ represents a flexible linking peptide of 6 GGGGS repeats; Hu34-39VH represents humanized CD47 monoclonal antibody Hu34-39 heavy chain variable region; IgG4CH/Hs represents IgG4 heavy chain constant region (specific sequence set forth in, for example, SEQ ID NO: 133) containing S228P/L235E/Y349C/T366S/L368A/Y407V mutation to form a "Hole" structure.

The CL sequence in the above structure is set forth in SEQ ID NO: 131.

2. Transient Expression of Anti-CD47/Anti-PD-L1 Bispecific Antibody in Expi-CHO Cells Expi-CHO cells were transfected with the recombinant plasmids of the above two expression vectors ScFabHuPL7-21Ks (or ScFabHuPL16-42Ks) and ScFabHu34-39Hs using the Expi-Fectamine CHO Transfection Kit. After culturing in serum-free medium for 14 days, the supernatant of Expi-CHO cells was collected and detected the expression of the bispecific antibody by Western blotting. The bispecific antibody formed by dimerization of two single chains of ScFabHuPL7-21Ks and ScFabHu34-39Hs was named ScFab (HuPL7-21Ks/Hu34-39Hs), and the bispecific antibody formed by dimerization of two single chains of ScFabHuPL16-42Ks and ScFabHu34-39Hs was named ScFab (HuPL16-42Ks/Hu34-39Hs).

3. Purification of Bispecific Anti-CD47/Anti-PD-L1 Antibodies

After expressed and secreted in Expi-CHO cells, the bispecific antibodies of the present disclosure were purified by the method of Protein A affinity chromatography with the following specific steps. After the Protein A affinity chromatography column was equilibrated with buffer, the supernatant of Expi-CHO cell culture concentrated by ultrafilter was injected, monitored at A280 (nm), washed with washing solution until the unbound protein was all washed away, and then the antibodies were eluted with elution buffer to obtain the corresponding bispecific antibodies. The purified bispecific antibodies were tested for purity by SEC-HPLC and for molecular weight by LC-MS, and subjected to quality identification for subsequent pharmaceutical research. The identification results of SEC-HPLC and LC-MS showed that the purities of the bispecific antibodies ScFab (HuPL7-21Ks/Hu34-39Hs) and ScFab (HuPL16-42Ks/Hu34-39Hs) both reached more than 95%, and the determination value of molecular weight matched the theoretical value.

Example 15 Construction of Stable Cell Line with High Expression of hPD-L1

Construction of Stable Cell Lines CHO-K1-hPD-L1 and Raji-hPD-L1 with High Expression of hPD-L1

CHO-K1 cells (from Shanghai Institute of Biochemistry and Cell Biology, Chinese Academy of Sciences) and Raji cells (from ImmuneOnco Biopharmaceuticals Inc.) were transfected with the eukaryotic expression plasmid pTargeT-hPD-L1 containing hPD-L1 (human PD-L1) extracellular region sequence (UniProtKB-Q9NZQ7(PD-L1 Human) >sp|Q9NZQ7119-238, SEQ ID NO: 134) by electroporation, and cultured in an incubator at 37° C. and 5% $CO_2$. After 24 h, cells were selected with a medium containing 500 μg/ml G418. After 12 days, the positive rate of the cell pool was detected by FACS. The cells after electroporation were plated (at a cell density of $1\times10^6$ cells/ml, 100 μl/well) and incubated with FITC anti-human PD-L1 antibody (SINO BIOLOGICAL, 10084-MMB6-F) at 4° C. for 60 min. The mean value under the FITC channel was read by a flow cytometer. After data analysis, the positive cell lines were selected for subcloning, and the CHO-K1/Raji cells from a single clone were selected. The cell lines with high expression of PD-L1 were named CHO-K1-hPD-L1 and Raji-hPD-L1.

Example 16 In Vitro Binding and Blocking Tests of Anti-CD47/Anti-PD-L1 Bispecific Antibody (by ELISA)

1. Anti-CD47/Anti-PD-L1 Bispecific Antibody Binding to PD-L1 (by ELISA)

Figure 11:
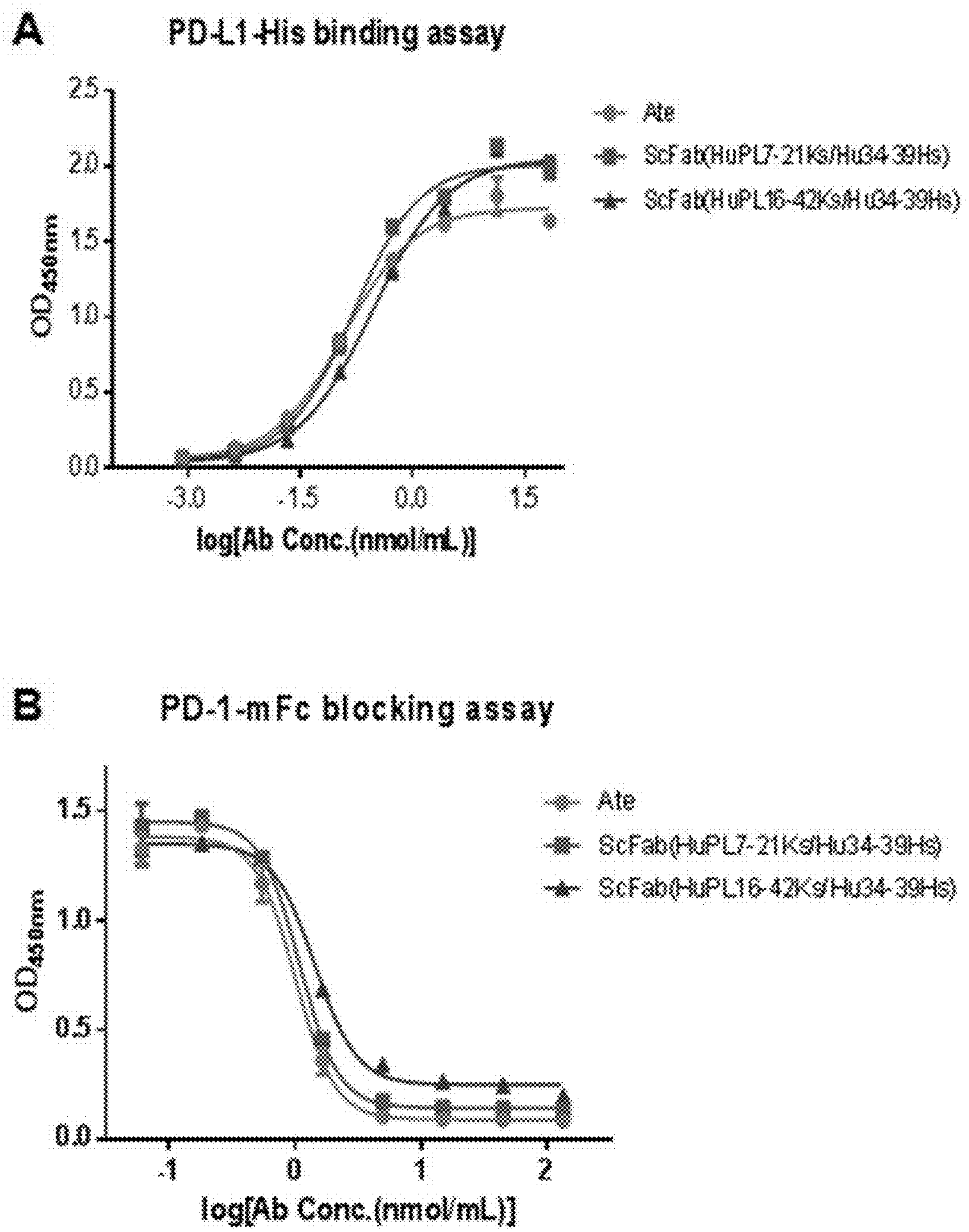
FIG. 11 shows the results of the bispecific antibodies ScFab (HuPL7-21Ks/Hu34-39Hs) and ScFab (HuPL16-42Ks/Hu34-39Hs) binding to PD-L1 (A), competing with PD-1 (B), binding to CD47 (C), competing with SIRPα (D) and competing with CD80 (E).

Human PD-L1-His protein (0.5 μg/ml, 100 μl/well) was coated on a 96-well ELISA plate and incubated at 37° C. for 2 h. After washing 3 times with 1×PBST, the plate was blocked with 5% nonfat milk at 4° C. overnight and then washed 3 times with 1×PBST. The bispecific antibody was added to the ELISA plate with concentrations starting from 10 μg/mL at 5-fold serial dilution, and incubated at 37° C. for 1.5 h, with Atezolizumab (Sino Biological, Cat: 68049-H001, abbreviated Ate) as a control antibody. After washing 5 times with 1×PBST, HRP-Anti-Human IgG secondary antibody (Jackson, 109-035-003, 1:10000) was added and incubated at 37° C. for 40 min. After washing 5 times with 1×PBST, color developing solution TMB was added to the plate, and a microplate reader (Thermo, Multiskan FC) was used to read OD450 value after termination of the reaction. The $EC_{50}$ results are shown in FIG. 11.

The experimental results show that both the bispecific antibodies ScFab (HuPL7-21Ks/Hu34-39Hs) and ScFab (HuPL16-42Ks/Hu34-39Hs) are able to bind to human PD-L1, and the binding to human PD-L1 was comparable to that of Atezolizumab.

2. Anti-CD47/Anti-PD-L1 Bispecific Antibody Competing with PD-1 (by ELISA)

The activity of antibodies to block the binding of PD1 to PD-L1 was analyzed by ELISA. Human PD-L1-hFC protein (2 μg/ml, 100 μl/well) was coated on a 96-well ELISA plate and incubated at 37° C. for 2 h. After washing 3 times with 1×PBST, the plate was blocked with 5% nonfat milk at 4° C. overnight and then washed 3 times with 1×PBST. The bispecific antibody ScFab (HuPL7-21Ks/Hu34-39Hs) or ScFab (HuPL16-42Ks/Hu34-39Hs) as the primary antibody was added to the ELISA plate with a total of 8 concentrations starting from 10 μg/mL at 3-fold serial dilution, and incubated together with 1 μg/mL PD-1-mFc at 37° C. for 1.5 h in the presence of serially diluted anti-PD-L1 antibody, with Atezolizumab (Sino Biological, Cat: 68049-H001, abbreviated Ate) as a control antibody. After washing 5 times with 1×PBST, Anti-Mouse IgG HRP (Jackson, 109-035-003, 1:10000) was used as the secondary antibody and incubated at 37° C. for 1 h. After washing 5 times with 1×PBST, color developing solution TMB was added to the plate, and the microplate reader was used to read OD450 value after termination of the reaction. The results are shown in FIG. 11.

The experimental results show that both the bispecific antibodies ScFab (HuPL7-21Ks/Hu34-39Hs) and ScFab (HuPL16-42Ks/Hu34-39Hs) had the ability to block the binding of PD-L1 to PD-1, and the blocking ability was comparable to that of Atezolizumab.

3. Anti-CD47/Anti-PD-L1 Bispecific Antibody Binding to CD47 (by ELISA)

The binding activity of antibodies to CD47 was analyzed by ELISA. Human CD47-His protein (0.5 μg/ml, 100 μl/well) was coated on a 96-well ELISA plate and incubated at 37° C. for 2 h. After washing 3 times with 1×PBST, the plate was blocked with 5% nonfat milk at 4° C. overnight and then washed 3 times with 1×PBST. The bispecific anti-CD47/anti-PD-L1 antibody provided by the present disclosure was added to the ELISA plate with a total of 8 concentrations starting from 50 μg/mL at 5-fold serial dilution, and incubated at 37° C. for 1.5 h, with Hu34-39-PE as a control antibody. After washing 5 times with 1×PBST, HRP-Anti-Human IgG (1:10000) was used as the secondary antibody and incubated at 37° C. for 40 min. After washing 5 times with 1×PBST, color developing solution TMB was added to the plate, and a microplate reader (Thermo, Multiskan FC) was used to read OD450 value after termination of the reaction. The $EC_{50}$ results are shown in FIG. 11.

The experimental results show that both the bispecific antibodies ScFab (HuPL7-21Ks/Hu34-39Hs) and ScFab (HuPL16-42Ks/Hu34-39Hs) are able to bind to human CD47, and their binding activities were reduced to varying degrees. The binding $EC_{50}$ value of ScFab (HuPL7-21Ks/Hu34-39Hs) was 40-fold higher than that of Hu34-39-PE.

4. Anti-CD47/Anti-PD-L1 Bispecific Antibody Competing with SIRPα (by ELISA)

The blocking activity of antibodies was analyzed by ELISA. Human CD47-His protein (0.4 μg/ml, 100 μl/well)

was coated on a 96-well ELISA plate and incubated at 37° C. for 2 h. After washing 3 times with 1×PBST, the plate was blocked with 5% nonfat milk at 4° C. overnight and then washed 3 times with 1×PBST. The bispecific antibody ScFab (HuPL7-21Ks/Hu34-39Hs) or ScFab (HuPL16-42Ks/Hu34-39Hs) as the primary antibody was added to the ELISA plate with a total of 8 concentrations starting from 10 μg/mL at 3-fold serial dilution, and incubated together with 2 μg/mL SIRPα-biotin at 37° C. for 1.5 h in the presence of serially diluted anti-CD47 antibody, with Hu34-39-PE as a control antibody. After washing 5 times with 1×PBST, SA-HRP (Jackson, 109-035-003, 1:10000) was used as the secondary antibody and incubated at 37° C. for 1 h. After washing 5 times with 1×PBST, color developing solution TMB was added to the plate, and the microplate reader was used to read OD450 value after termination of the reaction. The results are shown in FIG. 11.

The experimental results show that both the bispecific antibodies ScFab (HuPL7-21Ks/Hu34-39Hs) and ScFab (HuPL16-42Ks/Hu34-39Hs) are able to block the binding of CD47 to SIRPα, and the blocking ability was lower than that of Hu34-39-PE, with an $IC_{50}$ value increased by about 40 times.

5. Anti-CD47/Anti-PD-L1 Bispecific Antibody Competing with CD80 (by ELISA)

The activity of antibodies to block the binding of PD-L1 to CD80 was analyzed by ELISA. CD80-hFc protein (8 μg/ml, 100 μl/well) was coated on a 96-well ELISA plate and incubated overnight. After washing 3 times with 1×PBST, the plate was blocked with 5% nonfat milk at 37° C. for 2 h and then washed 3 times with 1×PBST. The bispecific antibody ScFab (HuPL7-21Ks/Hu34-39Hs) or ScFab (HuPL16-42Ks/Hu34-39Hs) as the primary antibody was added to the ELISA plate with a total of 8 concentrations starting from 30 μg/mL at 3-fold serial dilution, and incubated together with PD-L1-mFc at 37° C. for 1.5 h in the presence of serially diluted anti-PD-L1 antibody, with Atezolizumab as a control antibody. After washing 5 times with 1×PBST, Anti-Mouse IgG HRP was used as the secondary antibody and incubated at 37° C. for 1 h. After washing 5 times with 1×PBST, color developing solution TMB was added to the plate, and the microplate reader was used to read OD450 value after termination of the reaction. The results are shown in FIG. 11

The experimental results show that both the bispecific antibodies ScFab (HuPL7-21Ks/Hu34-39Hs) and ScFab (HuPL16-42Ks/Hu34-39Hs) are able to block the binding of PD-L1 to CD80, and the blocking ability was comparable to that of Atezolizumab.

The above experimental results show that the bispecific antibodies of the present disclosure bind to PD-L1/CD47 with different activities, so as to reduce the toxic response of the antibodies such as blood toxicity while ensuring the anti-tumor activity.

Figure 12:
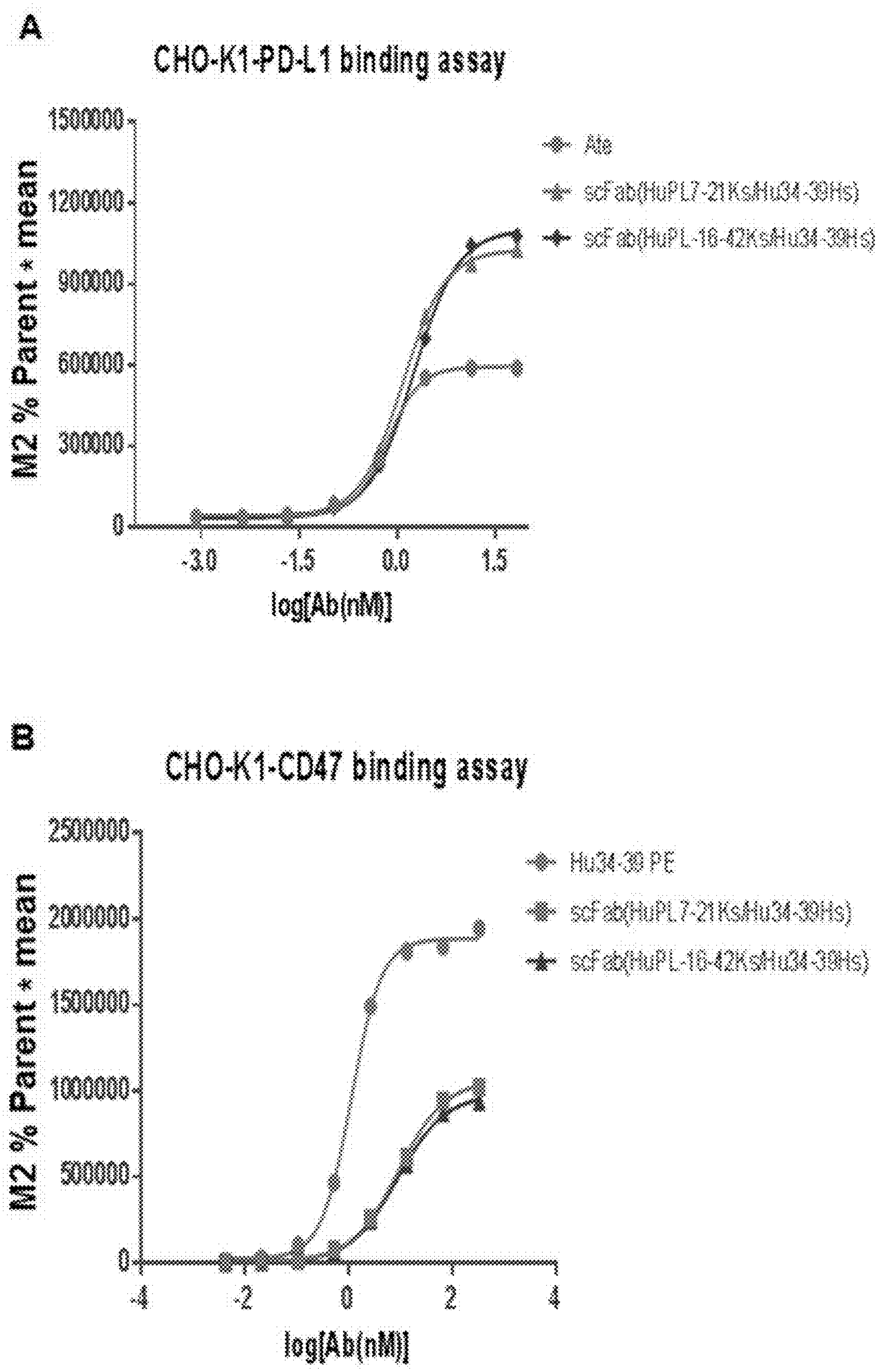
FIG. 12 shows the results of the bispecific antibodies ScFab (HuPL7-21Ks/Hu34-39Hs) and ScFab (HuPL16-42Ks/Hu34-39Hs) binding to PD-L1 on cell surface (A), binding to CD47 on cell surface (B), blocking the binding of PD-1 to PD-L1 (C) and blocking the binding of SIRPα to CD47 (D) at the cellular level.

Example 17 Binding/Blocking Test of Anti-CD47/Anti-PD-L1 Bispecific Antibody at Cellular Level 1. Binding Activity of Bispecific Antibodies ScFab (HuPL7-21Ks/Hu34-39Hs) and ScFab (HuPL16-42Ks/Hu34-39Hs) to PD-L1/CD47 on Cell Surface Detected by FACS The CHO-K1-hPD-L1/CHO-K1-hCD47 stable cell line was used as a PD-L1/CD47 provider, and the serially diluted bispecific anti-PD-L1/anti-CD47 antibody was added to the cells as the primary antibody and incubated at 4° C. for 1.5 h. PE Anti-Human IgG was used as the secondary antibody and incubated at 4° C. for 1 h. Atezolizumab and Hu34-39-PE were used as positive controls. The product of the mean value and the Parent value at a wavelength of 585 nm was read using a flow cytometer, and the results are shown in FIG. 12.

The experimental results show that both the bispecific antibodies ScFab (HuPL7-21Ks/Hu34-39Hs) and ScFab (HuPL16-42Ks/Hu34-39Hs) are able to bind to human PD-L1 on cell surface, and the binding ability was comparable to that of Atezolizumab. The binding activity of bispecific antibodies ScFab (HuPL7-21Ks/Hu34-39Hs) and ScFab (HuPL16-42Ks/Hu34-39Hs) to CD47 on cell surface was lower than that of Hu34-39-PE monoclonal antibody, with $EC_{50}$ increased by about 4 times and Emax decreased by about 2 times.

2. Ability of Bispecific Antibodies ScFab (HuPL7-21Ks/Hu34-39Hs) and ScFab (HuPL16-42Ks/Hu34-39Hs) to Block the Binding of PD-1/SIRPα to Cell Surface Detected by FACS The CHO-K1-hPD-L1/CHO-K1-hCD47 stable cell line was used as a PD-L1/CD47 provider to observe the binding of PD-L1 to PD-1 and the binding of CD47 to SIRPα in the presence of serially diluted anti-PD-L1 antibody/anti-CD47 antibody. The bispecific antibody ScFab (HuPL7-21Ks/Hu34-39Hs) or ScFab (HuPL16-42Ks/Hu34-39Hs) was used as the primary antibody, added to the cells after serial dilution together with 1 μg/mL PD-1-mFc and SIRPα-biotin respectively, and incubated at 37° C. for 1.5 h. PE-Anti-Mouse IgG/PE-SA was used as the secondary antibody. Atezolizumab was used as a positive control for blocking the binding of PD-1-mFc to PD-L1 on cell surface, and Hu34-39-PE was used as a positive control for blocking the binding of SIRPα to CD47 on cell surface. The results are shown in FIG. 12.

The experimental results show that both the bispecific antibodies ScFab (HuPL7-21Ks/Hu34-39Hs) and ScFab (HuPL16-42Ks/Hu34-39Hs) are able to block the binding of human PD-1 to CHO-K1-PD-L1 and SIRPα to CHO-K1-CD47, and the ability to block the binding of PD-1 to CHO-K1-PD-L1 was comparable to that of Atezolizumab. The ability of the bispecific antibodies to block the binding of SIRPα to CHO-K1-CD47 was lower than that of Hu34-39-PE, with an $IC_{50}$ value increased by 3 times.

According to the results of ELISA and FACS, the bispecific antibodies ScFab (HuPL7-21Ks/Hu34-39Hs) and ScFab (HuPL16-42Ks/Hu34-39Hs) had the similar ability of binding to and blocking of PD-L1 as Atezolizumab. While the ability of binding to CD47 decreased, the $EC_{50}$ increased by about 40 times detected by ELISA and the $EC_{50}$ increased by about 4 times and Emax decreased by 2 times detected by FACS. That is, the bispecific antibodies ScFab (HuPL7-21Ks/Hu34-39Hs) and ScFab (HuPL16-42Ks/Hu34-39Hs) bind to PD-L1/CD47 with different activities, which help to enhance the tumor targeting and reduce the adverse reactions, especially those against red blood cells, of the bispecific antibodies.

Example 18 Double Binding and Double Blocking Tests of Anti-CD47/Anti-PD-L1 Bispecific Antibody on Raji-hPD-L1 Cells Detected by FACS Raji-hPD-L1 tumor cells were purchased from ImmuneOnco Biopharmaceuticals Inc. Both of hPD-L1 and hCD47 were highly expressed on the surface of Raji-hPD-L1 cells. The bispecific antibodies ScFab (HuPL7-21Ks/Hu34-39Hs) and ScFab (HuPL16-42Ks/Hu34-39Hs) bound to both hPD-L1 and hCD47 on the surface of Raji-hPD-L1 cells, and also blocked the binding of CD47/SIRPα and the binding of PD-1/PD-L1 at the same time, showing dual-arm binding and dual-arm blocking activities. Dual-blocking: $2.4\times10^5$ per well Raji-hPD-L1 cells were plated in a plate with U-bottom. For the addition of the primary antibody, the antibody was diluted in 2-fold serial dilution to a total of 9 working concentrations starting from 2.5 μg/mL; SIRPα-mFc with a final antigen concentration of 1 μg/mL was evenly mixed with PD-1-mFc with a final concentration of 1 μg/mL; and 50 μl of the antibody and 50 μl of the antigen were premixed in each well, added to cell wells with a total of 100 μl, and then incubated at 4° C. for 1.5 h. For the addition of the secondary antibody, 200 μl of cell stain buffer was added first to wash three times, and 0.8 μl of PE-anti-mouse-IgG-Fc was added to each well and incubated at 4° C. for 1 h. Finally, 200 μl of cell stain buffer was added to wash three times, and 100 μl of cell stain buffer was added to resuspend the cells. A flow cytometry was used for detection. Dual-binding: $1.5\times10^6$ per well Raji-hPD-L1 cells were plated in a plate with U-bottom. For the addition of the primary antibody, the antibody was diluted in 5-fold serial dilution to a total of 8 working concentrations starting from 10 μg/mL, and then incubated at 4° C. for 1.5 h. For the addition of the secondary antibody, 200 μl of cell stain buffer was added first to wash three times, and 0.8 μl of PE-anti-human-IgG-Fc was added to each well and incubated at 4° C. for 1 h. Finally, 200 μl of cell stain buffer was added to wash three times, and 100 μl of cell stain buffer was added to resuspend the cells. A flow cytometry was used for detection.

Figure 13:
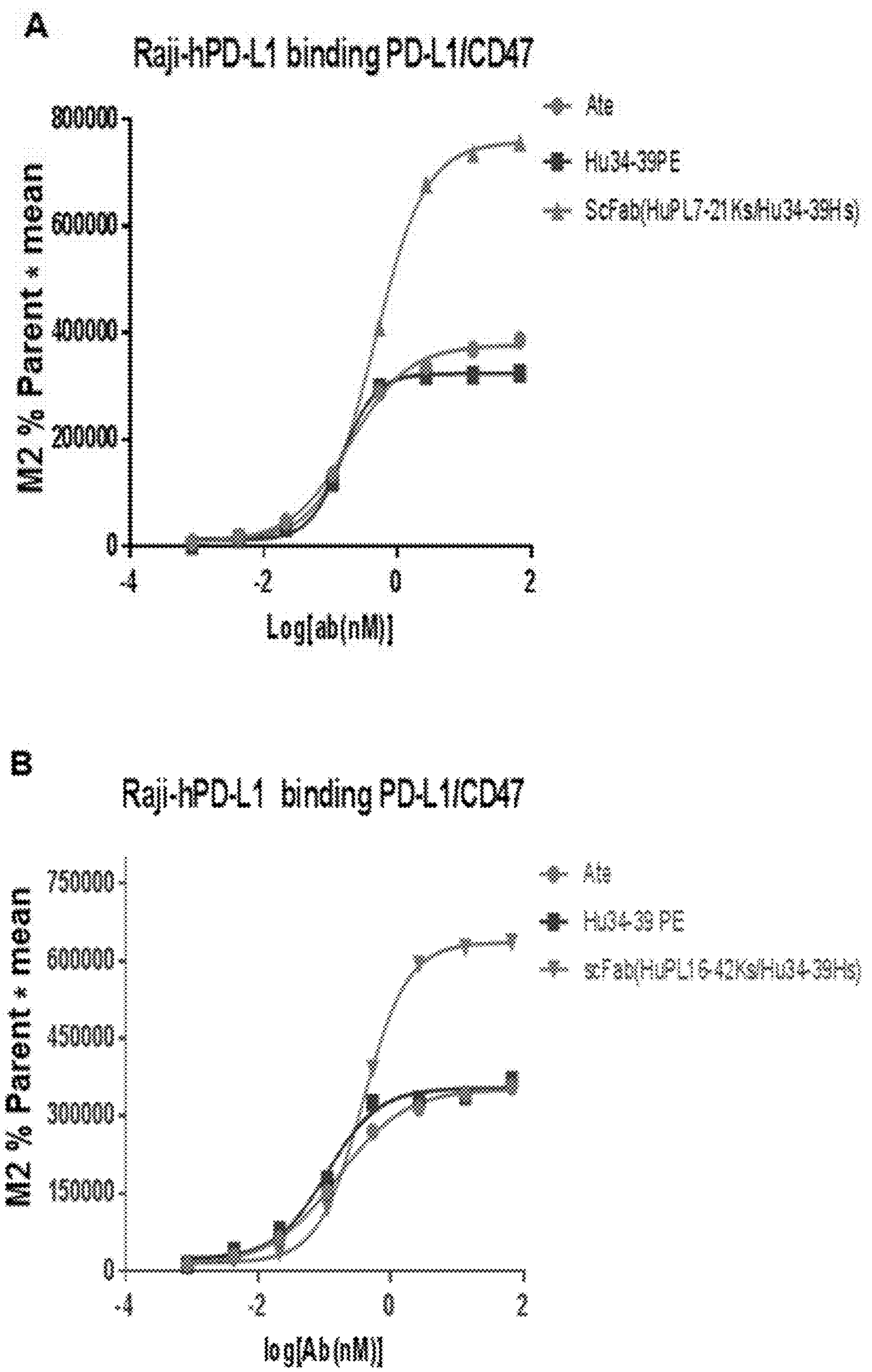
FIG. 13 shows the results of the bispecific antibodies ScFab (HuPL7-21Ks/Hu34-39Hs) and ScFab (HuPL16-42Ks/Hu34-39Hs) binding to both CD47 and PD-L1 on Raji-hPD-L1 cells (A, B) and blocking both CD47 and PD-L1 (B).

The experimental results are shown in FIG. 13. The results show that the bispecific antibody of the present disclosure bound to cells with dual-target, and simultaneously blocked the binding of CD47/SIRPα and the binding of PD-1/PD-L1 on the surface of the cells.

Example 19 Detection of the Inhibition of Anti-CD47/Anti-PD-L1 Bispecific Antibody on the Growth of Transplanted Tumor in Mice With the characteristics of NOD, Prkdcscid, IL2rgnull deletion/mutation, NSG mice are the tool mice with the highest degree of immunodeficiency and are most suitable for human cell transplantation, showing little rejection of human cells and tissues. In the present disclosure, NSG mice (purchased from Biocytogen Pharmaceuticals (Beijing) Co., Ltd.) and Raji-hPD-L1 tumor cells were used to establish a tumor xenograft model, Raji-PBMC-NSG model, to study the antitumor effect of the anti-CD47/anti-PD-L1 bispecific antibody ScFab (HuPL7-21Ks/Hu34-39Hs) in a subcutaneous transplant model of Raji-hPD-L1 lymphoma. The anti-CD47 monoclonal antibody 5F9 was purchased from Sino Biological Inc. (Cat: 68063-H001). Table 14 shows the experimental design of the antitumor effect of the test drugs in Raji-PBMC-NSG tumor model.

TABLE 14

Experimental design for drug test in Raji-PBMC-NSG model

| Group | N | Antibody | Mouse strain | Dosage (mg/kg) | Dosing volume (μl/g) | Route of administration | Dosing frequency |
|---|---|---|---|---|---|---|---|
| 1 | 6 | PBS | NSG | — | 10 | i.v. | q.w × 3 |
| 2 | 6 | Atezolizumab | NSG | 10 | 10 | i.v. | q.w × 3 |
| 3 | 6 | Atezolizumab + 5F9 | NSG | 10 + 10 | 10 | i.v. | q.w × 3 |
| 4 | 6 | BiAb | NSG | 10 | 10 | i.v. | q.w × 3 |
| 5 | 6 | BiAb | NSG | 20 | 10 | i.v. | q.w × 3 |

a: N refers to the number of mice per group;
b: BiAb refers to bispecific antibody ScFab (HuPL7-21Ks/Hu34-39Hs).

Figure 14:
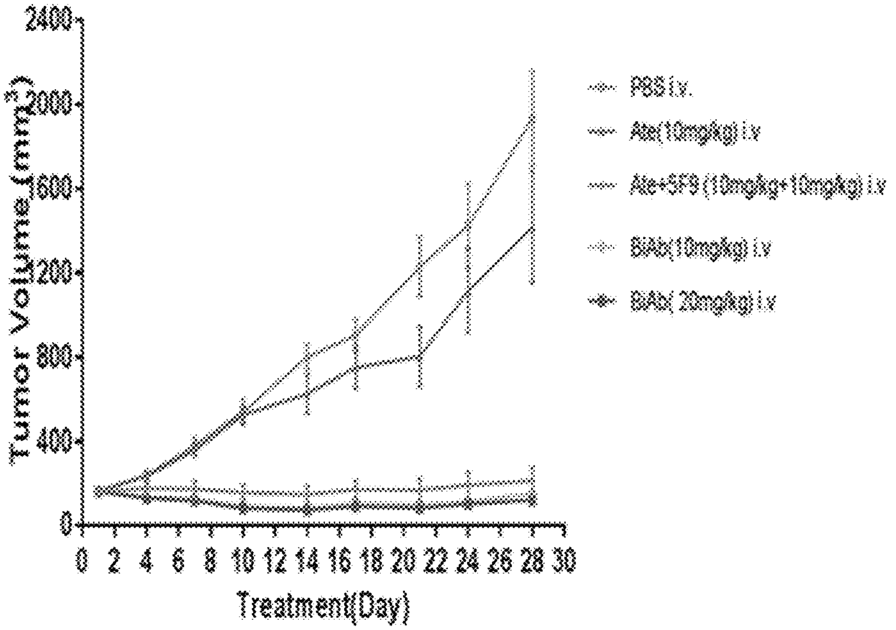
FIG. 14 shows the results of the bispecific antibody ScFab (HuPL7-21Ks/Hu34-39Hs) inhibiting the growth of transplanted tumors in mice.

The changes of tumor volume in each group over time are shown in FIG. 14. The anti-tumor effect of the bispecific antibody of the present disclosure was significantly superior to that of Atezolizumab, and was better than the combination of monoclonal antibodies (Atezolizumab+5F9).

Example 20 Acute Toxicity Test of Anti-CD47/Anti-PD-L1 Bispecific Antibody in Cynomolgus Monkey In this example, a toxicity test of the anti-CD47/anti-PD-L1 bispecific antibody ScFab (HuPL7-21Ks/Hu34-39Hs) of the present disclosure (abbreviated as BiAb) was performed by administering to cynomolgus monkeys by single intravenous infusion. The administration doses of the bispecific antibody were 10, 30 and 100 mg/kg, one male and one female cynomolgus monkeys in each group. The anti-CD47 monoclonal antibody Hu34-39-PE was administered at a dose of 30 mg/kg, and Hu5F9 was administered at a dose of 20 mg/kg, with two cynomolgus monkeys in each group.

Monkeys were administered by single intravenous infusion, with an observation period of 21 days. Blood samples were collected from the femoral vein at different time points for the detection of blood cell count, coagulation function indexes, and blood biochemical indexes.

The results of drug safety evaluation show that as of the 21st day, no monkeys died in all groups, and there were no abnormalities in general state observation, food intake, body weight, etc. in each group.

Animals given the bispecific antibody ScFab (HuPL7-21Ks/Hu34-39Hs) showed no change in RBC count, HGB content and RET %. The bispecific antibody ScFab (HuPL7-21Ks/Hu34-39Hs) did not show toxicity on red blood cells and other hematological toxicity at doses of 10, 30 and 100 mg/kg.

Animals given the monoclonal antibody Hu5F9 (20 mg/kg) showed a significant decrease in RBC count and HGB content, and a significant increase in RET %. Animals given the monoclonal antibody Hu34-39-PE (30 mg/kg) showed a certain extent of decrease in RBC count and HGB content, and an increase in RET % less than the monoclonal antibody Hu5F9. Hu5F9 showed obvious toxicity on red blood cells, and Hu34-39-PE showed a weaker toxicity on red blood cells than Hu5F9. The safety of the bispecific antibody ScFab (HuPL7-21Ks/Hu34-39Hs) for red blood cells was significantly better than that of monoclonal antibodies Hu34-39-PE and Hu5F9.

The above examples show that the anti-CD47/anti-PD-L1 bispecific antibody ScFab (HuPL7-21Ks/Hu34-39Hs) of the present disclosure differentially binds to CD47 and PD-L1, and fairly retains the activities of binding to and blocking of PD-L1, without toxicity on red blood cells and other hematological toxicity, exhibiting an excellent safety.

Example 21 Detection of the Inhibition of Anti-PD-L1 Antibody on the Growth of Transplanted Tumor in Mice In the present disclosure, NSG mice (purchased from Biocytogen Pharmaceuticals (Beijing) Co., Ltd., China) and Raji-hPD-L1 tumor cells (purchased from ImmuneOnco Biopharmaceuticals Inc., China) were used to establish a tumor xenograft model, Raji-PBMC-NSG model, to study the antitumor effect of the antibody of the present disclosure in a subcutaneous transplant model of Raji-hPD-L1 lymphoma. The anti-PD-L1 positive control antibody was Atezolizumab (Sino Biological, Cat: 68049-H001). There were 6 mice in each group. The negative control group was given normal saline (PBS). The anti-PD-L1 antibody HuPL7-21 of the present disclosure and Atezolizumab were administered at a dose of 10 mg/kg, respectively. The route of administration was intraperitoneal injection, and the dosing frequency was two times a week for three consecutive weeks.

At the end of the experiment, the tumor inhibition rate ($TGI_{TV}$) % of each group was calculated, as shown in Table 15.

TABLE 15

Effect of each antibody on the tumor volume of Raji-PBMC-NSG model mice

| Group | Dosage (mg/kg) | $TGI_{TV}$ (%) |
|---|---|---|
| PBS | — | 0.00 |
| Atezolizumab | 10 | 37.40 |
| HuPL7-21 | 10 | 48.75 |

The anti-PD-L1 antibody HuPL7-21 of the present disclosure has a significantly better anti-tumor effect in vivo than Atezolizumab.

Although the present disclosure has been described above in detail, those skilled in the art should understand that various modifications and changes can be made to the present disclosure without departing from the spirit and scope of the present disclosure. The scope of the present invention should not be limited to the detailed description above, but should be attributable to the appended claims.

What is claimed is:

1. An anti-CD47/anti-PD-L1 antibody comprising an anti-CD47 antibody or antigen-binding fragment thereof and an anti-PD-L1 antibody or antigen-binding fragment thereof, wherein:

the anti-CD47 antibody or antigen-binding fragment thereof comprises a first heavy chain variable region and a first light chain variable region, wherein:

(1) the first heavy chain variable region comprises H1CDR1, H1CDR2 and H1CDR3 comprising amino acid sequences set forth in SEQ ID NOs: 4, 5 and 6, respectively; and (2) the first light chain variable region comprises L1CDR1, L1CDR2 and L1CDR3 comprising amino acid sequences set forth in SEQ ID NOs: 15, 16 and 17, respectively; and the anti-PD-L1 antibody or antigen-binding fragment thereof comprises a second heavy chain variable region and a second light chain variable region, wherein:

the second heavy chain variable region comprises H2CDR1, H2CDR2 and H2CDR3 comprising amino acid sequences set forth in SEQ ID NOs: 75, 76 and 77, respectively, and the second light chain variable region comprises L2CDR1, L2CDR2 and L2CDR3 comprising amino acid sequences set forth in SEQ ID NOs: 78, 79 and 80, respectively;

the second heavy chain variable region comprises H2CDR1, H2CDR2 and H2CDR3 comprising amino acid sequences set forth in SEQ ID NOs: 87, 88 and 89, respectively, and the second light chain variable region comprises L2CDR1, L2CDR2 and L2CDR3 comprising amino acid sequences set forth in SEQ ID NOs: 90, 91 and 92, respectively;

the second heavy chain variable region comprises H2CDR1, H2CDR2 and H2CDR3 comprising amino acid sequences set forth in SEQ ID NOs: 81, 82 and 83, respectively, and the second light chain variable region comprises L2CDR1, L2CDR2 and L2CDR3 comprising amino acid sequences set forth in SEQ ID NOs: 84, 85 and 86, respectively; or the second heavy chain variable region comprises H2CDR1, H2CDR2 and H2CDR3 comprising amino acid sequences set forth in SEQ ID NOs: 93, 94 and 95, respectively, and the second light chain variable region comprises L2CDR1, L2CDR2 and L2CDR3 comprising amino acid sequences set forth in SEQ ID NOs: 96, 97 and 98, respectively.

2. The anti-CD47/anti-PD-L1 antibody according to claim 1, wherein: (1) the first heavy chain variable region comprises an amino acid sequence selected from the group consisting of: (b1) amino acid sequences set forth in SEQ ID NO: 22 and SEQ ID NO: 30; and (2) the first light chain variable region comprises an amino acid sequence selected from the group consisting of: (b2) amino acid sequences set forth in SEQ ID NO: 25 and SEQ ID NO: 33.

3. The anti-CD47/anti-PD-L1 antibody according to claim 1, comprising an anti-PD-L1 antibody or antigen-binding fragment thereof, wherein: the anti-PD-L1 antibody or antigen-binding fragment thereof comprises a second heavy chain variable region and a second light chain variable region, wherein: (1) the second heavy chain variable region comprises an amino acid sequence selected from the group consisting of: (B1) amino acid sequences set forth in SEQ ID NOs: 99, 100, 101, 102, 110, 111, 112, 113, 114, 119, 120, 121, 122 and 123; and (2) the second light chain variable region comprises an amino acid sequence selected from the group consisting of: (B2) amino acid sequences set forth in SEQ ID NOs: 103, 104, 105, 106, 115, 116, 117, 118, 124, 125 and 126.

4. The anti-CD47/anti-PD-L1 antibody according to claim 1, wherein:

(1) the first heavy chain variable region comprises an amino acid sequence (2) the first light chain variable region comprises an amino acid sequence set forth in SEQ ID NO: 33.

5. The anti-CD47/anti-PD-L1 antibody according to claim 1, comprising an anti-PD-L1 antibody or antigen-binding fragment thereof, wherein:

the anti-PD-L1 antibody or antigen-binding fragment thereof comprises a second heavy chain variable region and a second light chain variable region, wherein:

the second heavy chain variable region comprises an amino acid sequence selected from the group consisting of:

amino acid sequences set forth in SEQ ID NOs: 110, 111, 112, 113 and 114; and the second light chain variable region comprises an amino acid sequence selected from the group consisting of:

amino acid sequences set forth in SEQ ID NOs: 115, 116, 117 and 118 or the second heavy chain variable region comprises an amino acid sequence selected from the group consisting of:

amino acid sequences set forth in SEQ ID NOs: 119, 120, 121, 122 and 123; and the second light chain variable region comprises an amino acid sequence selected from the group consisting of:

amino acid sequences set forth in SEQ ID NOs: 124, 125 and 126.

6. The anti-CD4'7/anti-PD-L1 antibody according to claim 1, comprising an anti-PD-L1 antibody or antigen-binding fragment thereof, wherein:

the anti-PD-L1 antibody or antigen-binding fragment thereof comprises a second heavy chain variable region and a second light chain variable region, wherein:

the second heavy chain variable region comprises an amino acid sequence set forth in SEQ ID NO: 112; and the second light chain variable region comprises an amino acid sequence set forth in SEQ ID NO: 116;

the second heavy chain variable region comprises an amino acid sequence set forth in SEQ ID NO: 123; and the second light chain variable region comprises an amino acid sequence set forth in SEQ ID NO: 126; or the second heavy chain variable region comprises an amino acid sequence set forth in SEQ ID NO: 102; and the second light chain variable region comprises an amino acid sequence set forth in SEQ ID NO: 106.

7. The anti-CD47/anti-PD-L1 antibody according to claim 1, wherein the antibody is a humanized antibody.

8. The anti-CD47/anti-PD-L1 antibody according to claim 1, wherein the antibody is a bispecific antibody.

9. An isolated nucleic acid encoding the anti-CD47/anti-PD-L1 antibody according to claim 1.

10. The nucleic acid according to claim 9, wherein (1) the nucleotide sequence encoding the amino acid sequence of the first heavy chain variable region is set forth in SEQ ID NO: 36;

(2) the nucleotide sequence encoding the amino acid sequence of the first light chain variable region is set forth in SEQ ID NO: 39;

(3) the nucleotide sequence encoding the amino acid sequence of the second heavy chain variable region is set forth in SEQ ID NO: 127 or SEQ ID NO: 128; and (4) the nucleotide sequence encoding the amino acid sequence of the second light chain variable region is set forth in SEQ ID NO: 129 or SEQ ID NO: 130.

11. An expression vector comprising the nucleic acid according to claim 9.

12. A host cell transformed with the expression vector according to claim 11, wherein the host cell is selected from the group consisting of prokaryotic cells and eukaryotic cells.

13. A method for producing the anti-CD47/anti-PD-L1 antibody according to claim 1, comprising expressing the antibody in the host cell according to claim 12, and isolating the antibody from the host cell.

14. A pharmaceutical composition comprising the anti-CD47/anti-PD-L1 antibody according to claim 1 and a pharmaceutically acceptable carrier.

15. A method for treating a cancer comprising administering the anti-CD47/anti-PD-L1 antibody according to claim 1 to the subject in need thereof.

16. The method according to claim 15, wherein the cancer is selected from the group consisting of hematological tumor, lymphoma, breast cancer, lung cancer, gastric cancer, intestinal cancer, esophageal cancer, ovarian cancer, cervical cancer, kidney cancer, bladder cancer, pancreatic cancer, glioma and melanoma.

17. The host cell according to claim 12, wherein the cell is a mammalian cell.

* * * * *

SEQUENCE LISTING

```
<160> NUMBER OF SEQ ID NOS: 134

<210> SEQ ID NO 1
<211> LENGTH: 8
<212> TYPE: PRT
<213> ORGANISM: Artificial sequence
<220> FEATURE:
<223> OTHER INFORMATION: H1CDR1

<400> SEQUENCE: 1

Gly Tyr Ile Phe Thr Asp Tyr Tyr
1               5


<210> SEQ ID NO 2
<211> LENGTH: 8
<212> TYPE: PRT
<213> ORGANISM: Artificial sequence
<220> FEATURE:
<223> OTHER INFORMATION: H1CDR2

<400> SEQUENCE: 2

Ile Thr Pro Gly Ser Gly Leu Thr
1               5


<210> SEQ ID NO 3
<211> LENGTH: 12
<212> TYPE: PRT
<213> ORGANISM: Artificial sequence
<220> FEATURE:
<223> OTHER INFORMATION: H1CDR3

<400> SEQUENCE: 3

Ala Arg Cys Ser Tyr Gly Ser Ser Phe Pro His Val
1               5                   10


<210> SEQ ID NO 4
<211> LENGTH: 8
<212> TYPE: PRT
<213> ORGANISM: Artificial sequence
```

<220> FEATURE:
<223> OTHER INFORMATION: VH CDR1 of SHC025-34

<400> SEQUENCE: 4

Gly Tyr Thr Phe Thr Asn Tyr Trp
1 5

<210> SEQ ID NO 5
<211> LENGTH: 8
<212> TYPE: PRT
<213> ORGANISM: Artificial sequence
<220> FEATURE:
<223> OTHER INFORMATION: VH CDR2 of SHC025-34

<400> SEQUENCE: 5

Ile Thr Pro Gly Arg Gly Glu Thr
1 5

<210> SEQ ID NO 6
<211> LENGTH: 10
<212> TYPE: PRT
<213> ORGANISM: Artificial sequence
<220> FEATURE:
<223> OTHER INFORMATION: VH CDR3 of SHC025-34

<400> SEQUENCE: 6

Ser Arg Trp Gly Leu Arg Arg Gly Asp Tyr
1 5 10

<210> SEQ ID NO 7
<211> LENGTH: 8
<212> TYPE: PRT
<213> ORGANISM: Artificial sequence
<220> FEATURE:
<223> OTHER INFORMATION: H1CDR1

<400> SEQUENCE: 7

Gly Phe Ile Phe Ser Arg Phe Gly
1 5

<210> SEQ ID NO 8
<211> LENGTH: 8
<212> TYPE: PRT
<213> ORGANISM: Artificial sequence
<220> FEATURE:
<223> OTHER INFORMATION: H1CDR2

<400> SEQUENCE: 8

Ile Ser Ser Gly Gly Ser Tyr Thr
1 5

<210> SEQ ID NO 9
<211> LENGTH: 14
<212> TYPE: PRT
<213> ORGANISM: Artificial sequence
<220> FEATURE:
<223> OTHER INFORMATION: H1CDR3

<400> SEQUENCE: 9

Ala Arg Gln Gly Leu Leu Asp Tyr Leu Tyr Ala Leu Asp Tyr
1 5 10

<210> SEQ ID NO 10
<211> LENGTH: 8
<212> TYPE: PRT
<213> ORGANISM: Artificial sequence
<220> FEATURE:

<223> OTHER INFORMATION: H1CDR1

<400> SEQUENCE: 10

Gly Tyr Thr Phe Thr Asp Tyr Tyr
1               5

<210> SEQ ID NO 11
<211> LENGTH: 12
<212> TYPE: PRT
<213> ORGANISM: Artificial sequence
<220> FEATURE:
<223> OTHER INFORMATION: H1CDR3

<400> SEQUENCE: 11

Ala Arg Thr Ser Tyr Gly Ser Ser Phe Pro His Val
1               5                   10

<210> SEQ ID NO 12
<211> LENGTH: 12
<212> TYPE: PRT
<213> ORGANISM: Artificial sequence
<220> FEATURE:
<223> OTHER INFORMATION: L1CDR1

<400> SEQUENCE: 12

Gln Ser Leu Leu Asn Val Asn Asp Gln Lys Asn Tyr
1               5                   10

<210> SEQ ID NO 13
<211> LENGTH: 3
<212> TYPE: PRT
<213> ORGANISM: Artificial sequence
<220> FEATURE:
<223> OTHER INFORMATION: L1CDR2

<400> SEQUENCE: 13

Phe Ala Ser
1

<210> SEQ ID NO 14
<211> LENGTH: 9
<212> TYPE: PRT
<213> ORGANISM: Artificial sequence
<220> FEATURE:
<223> OTHER INFORMATION: L1CDR3

<400> SEQUENCE: 14

Gln Gln His Tyr Ser Thr Pro Leu Thr
1               5

<210> SEQ ID NO 15
<211> LENGTH: 7
<212> TYPE: PRT
<213> ORGANISM: Artificial sequence
<220> FEATURE:
<223> OTHER INFORMATION: VL CDR1 of SHC025-34

<400> SEQUENCE: 15

Ser Ser Val Ser Ser Ser Tyr
1               5

<210> SEQ ID NO 16
<211> LENGTH: 3
<212> TYPE: PRT
<213> ORGANISM: Artificial sequence
<220> FEATURE:
<223> OTHER INFORMATION: VL CDR2 of SHC025-34

<400> SEQUENCE: 16

Ser Thr Ser
1

<210> SEQ ID NO 17
<211> LENGTH: 9
<212> TYPE: PRT
<213> ORGANISM: Artificial sequence
<220> FEATURE:
<223> OTHER INFORMATION: VL CDR3 of SHC025-34

<400> SEQUENCE: 17

Gln Gln Tyr Ser Gly Tyr Pro Leu Thr
1 5

<210> SEQ ID NO 18
<211> LENGTH: 6
<212> TYPE: PRT
<213> ORGANISM: Artificial sequence
<220> FEATURE:
<223> OTHER INFORMATION: L1CDR1

<400> SEQUENCE: 18

Gln Asp Ile Asn Ser Phe
1 5

<210> SEQ ID NO 19
<211> LENGTH: 3
<212> TYPE: PRT
<213> ORGANISM: Artificial sequence
<220> FEATURE:
<223> OTHER INFORMATION: L1CDR2

<400> SEQUENCE: 19

Arg Ala Tyr
1

<210> SEQ ID NO 20
<211> LENGTH: 9
<212> TYPE: PRT
<213> ORGANISM: Artificial sequence
<220> FEATURE:
<223> OTHER INFORMATION: L1CDR3

<400> SEQUENCE: 20

Gln Gln Tyr Val Glu Phe Pro Pro Thr
1 5

<210> SEQ ID NO 21
<211> LENGTH: 119
<212> TYPE: PRT
<213> ORGANISM: Artificial sequence
<220> FEATURE:
<223> OTHER INFORMATION: VH of SHC025-26

<400> SEQUENCE: 21

Gln Val Gln Leu Lys Gln Ser Gly Ala Glu Leu Val Arg Pro Gly Ala
1 5 10 15

Ser Val Lys Leu Ser Cys Lys Ala Ser Gly Tyr Ile Phe Thr Asp Tyr
20 25 30

Tyr Met Asn Trp Val Lys Gln Arg Pro Gly Gln Gly Leu Glu Trp Ile
35 40 45

Ala Arg Ile Tyr Pro Gly Ser Gly Leu Thr Tyr Tyr Asn Ala Lys Phe
50 55 60

```
Lys Gly Lys Ala Thr Val Thr Ala Glu Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Cys Ser Tyr Gly Ser Ser Phe Pro His Val Trp Gly Thr Gly
            100                 105                 110

Thr Thr Val Thr Val Ser Ser
        115


<210> SEQ ID NO 22
<211> LENGTH: 117
<212> TYPE: PRT
<213> ORGANISM: Artificial sequence
<220> FEATURE:
<223> OTHER INFORMATION: VH of SHC025-34

<400> SEQUENCE: 22

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Trp Ile Thr Trp Val Lys Gln Arg Pro Gly Gln Gly Leu Glu Trp Ile
        35                  40                  45

Gly Asp Ile Thr Pro Gly Arg Gly Glu Thr Asn Tyr Asn Glu Lys Phe
    50                  55                  60

Lys Ser Lys Ala Thr Leu Thr Val Asp Thr Ser Ser Ser Thr Ala Tyr
65                  70                  75                  80

Met Gln Leu Thr Ser Leu Thr Ser Glu Asp Ser Ala Val Tyr Tyr Cys
                85                  90                  95

Ser Arg Trp Gly Leu Arg Arg Gly Asp Tyr Trp Gly Gln Gly Thr Ser
            100                 105                 110

Val Thr Val Ser Ser
        115


<210> SEQ ID NO 23
<211> LENGTH: 121
<212> TYPE: PRT
<213> ORGANISM: Artificial sequence
<220> FEATURE:
<223> OTHER INFORMATION: VH of SHC025-58

<400> SEQUENCE: 23

Glu Val Gln Leu Val Glu Ser Gly Gly Asp Leu Val Glu Pro Gly Gly
1               5                   10                  15

Ser Leu Lys Leu Ser Cys Ala Ala Ser Gly Phe Ile Phe Ser Arg Phe
            20                  25                  30

Gly Met Ala Trp Val Arg Gln Thr Pro Asp Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Leu Thr Ile Ser Arg Asp Asn Ala Lys Thr Thr Leu Tyr
65                  70                  75                  80

Leu Gln Met Arg Ser Leu Lys Ser Glu Asp Thr Ala Met Tyr Tyr Cys
                85                  90                  95

Ala Arg Gln Gly Leu Leu Asp Tyr Leu Tyr Ala Leu Asp Tyr Trp Gly
            100                 105                 110

Gln Gly Thr Ala Val Thr Val Ser Ser
```

115 120

<210> SEQ ID NO 24
<211> LENGTH: 113
<212> TYPE: PRT
<213> ORGANISM: Artificial sequence
<220> FEATURE:
<223> OTHER INFORMATION: VL of SHC025-26

<400> SEQUENCE: 24

Asp Ile Val Met Thr Gln Ser Pro Phe Ser Leu Ala Met Ser Val Gly
1 5 10 15

Gln Lys Val Thr Met Ser Cys Lys Ser Ser Gln Ser Leu Leu Asn Val
20 25 30

Asn Asp Gln Lys Asn Tyr Leu Ala Trp Tyr Gln Gln Lys Pro Gly Gln
35 40 45

Ser Pro Lys Leu Leu Val Tyr Phe Ala Ser Thr Arg Glu Ser Gly Val
50 55 60

Pro Asp Arg Phe Ile Gly Ser Gly Ser Gly Thr Asp Phe Thr Leu Thr
65 70 75 80

Ile Ser Ser Val Gln Ala Glu Asp Leu Ala Asp Tyr Phe Cys Gln Gln
85 90 95

His Tyr Ser Thr Pro Leu Thr Phe Gly Ala Gly Thr Lys Leu Glu Leu
100 105 110

Lys

<210> SEQ ID NO 25
<211> LENGTH: 108
<212> TYPE: PRT
<213> ORGANISM: Artificial sequence
<220> FEATURE:
<223> OTHER INFORMATION: VL of SHC025-34

<400> SEQUENCE: 25

Glu Asn Val Leu Thr Gln Ser Pro Ala Ile Met Ser Ala Ser Pro Gly
1 5 10 15

Glu Lys Val Thr Met Thr Cys Arg Ala Ser Ser Ser Val Ser Ser Ser
20 25 30

Tyr Leu Asn Trp Tyr Gln Gln Lys Ser Gly Ala Ser Pro Lys Leu Trp
35 40 45

Ile Tyr Ser Thr Ser Asn Leu Ala Ser Gly Val Pro Gly Arg Phe Ser
50 55 60

Gly Ser Gly Ser Gly Thr Ser Tyr Ser Leu Thr Ile Ser Ser Val Glu
65 70 75 80

Ala Glu Asp Ala Ala Thr Tyr Tyr Cys Gln Gln Tyr Ser Gly Tyr Pro
85 90 95

Leu Thr Phe Gly Ala Gly Thr Lys Leu Glu Val Lys
100 105

<210> SEQ ID NO 26
<211> LENGTH: 107
<212> TYPE: PRT
<213> ORGANISM: Artificial sequence
<220> FEATURE:
<223> OTHER INFORMATION: VL of SHC025-58

<400> SEQUENCE: 26

Asp Ile Lys Met Ile Gln Ser Pro Ser Ser Met Tyr Ala Gly Leu Gly
1 5 10 15

Glu Arg Val Thr Phe Asn Cys Lys Ala Ser Gln Asp Ile Asn Ser Phe
20 25 30

Leu Cys Trp Phe Gln Gln Lys Pro Gly Lys Ser Pro Arg Pro Leu Ile
35 40 45

Tyr Arg Ala Tyr Arg Leu Val Asp Gly Val Pro Ser Arg Phe Ser Gly
50 55 60

Val Gly Ser Gly Gln Asp Tyr Ser Leu Thr Ile Ser Ser Leu Asp Tyr
65 70 75 80

Glu Asp Leu Gly Ile Tyr Tyr Cys Gln Gln Tyr Val Glu Phe Pro Pro
85 90 95

Thr Phe Gly Ala Gly Thr Met Leu Glu Leu Lys
100 105

<210> SEQ ID NO 27
<211> LENGTH: 119
<212> TYPE: PRT
<213> ORGANISM: Artificial sequence
<220> FEATURE:
<223> OTHER INFORMATION: VH of SHC025-26CHI-T

<400> SEQUENCE: 27

Gln Val Gln Leu Lys Gln Ser Gly Ala Glu Leu Val Arg Pro Gly Ala
1 5 10 15

Ser Val Lys Leu Ser Cys Lys Ala Ser Gly Tyr Ile Phe Thr Asp Tyr
20 25 30

Tyr Met Asn Trp Val Lys Gln Arg Pro Gly Gln Gly Leu Glu Trp Ile
35 40 45

Ala Arg Ile Tyr Pro Gly Ser Gly Leu Thr Tyr Tyr Asn Ala Lys Phe
50 55 60

Lys Gly Lys Ala Thr Val Thr Ala Glu Lys Ser Ser Ser Thr Ala Tyr
65 70 75 80

Met Gln Leu Ser Ser Leu Thr Ser Glu Asp Ser Ala Val Tyr Phe Cys
85 90 95

Ala Arg Thr Ser Tyr Gly Ser Ser Phe Pro His Val Trp Gly Thr Gly
100 105 110

Thr Thr Val Thr Val Ser Ser
115

<210> SEQ ID NO 28
<211> LENGTH: 107
<212> TYPE: PRT
<213> ORGANISM: Artificial sequence
<220> FEATURE:
<223> OTHER INFORMATION: VL of SHC025-58CHI-A

<400> SEQUENCE: 28

Asp Ile Lys Met Ile Gln Ser Pro Ser Ser Met Tyr Ala Gly Leu Gly
1 5 10 15

Glu Arg Val Thr Phe Asn Cys Lys Ala Ser Gln Asp Ile Asn Ser Phe
20 25 30

Leu Ala Trp Phe Gln Gln Lys Pro Gly Lys Ser Pro Arg Pro Leu Ile
35 40 45

Tyr Arg Ala Tyr Arg Leu Val Asp Gly Val Pro Ser Arg Phe Ser Gly
50 55 60

Val Gly Ser Gly Gln Asp Tyr Ser Leu Thr Ile Ser Ser Leu Asp Tyr
65 70 75 80

Glu Asp Leu Gly Ile Tyr Tyr Cys Gln Gln Tyr Val Glu Phe Pro Pro
85 90 95

```
Thr Phe Gly Ala Gly Thr Met Leu Glu Leu Lys
            100                 105


<210> SEQ ID NO 29
<211> LENGTH: 119
<212> TYPE: PRT
<213> ORGANISM: Artificial sequence
<220> FEATURE:
<223> OTHER INFORMATION: VH of Hu26T-31-PE

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

Gly Arg Ile Tyr Pro Gly Ser Gly Leu Thr Tyr Tyr Asn Ala Lys Phe
    50                  55                  60

Lys Gly Arg Ala Thr Val Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Ser Tyr Gly Ser Ser Phe Pro His Val Trp Gly Gln Gly
            100                 105                 110

Thr Thr Val Thr Val Ser Ser
        115


<210> SEQ ID NO 30
<211> LENGTH: 117
<212> TYPE: PRT
<213> ORGANISM: Artificial sequence
<220> FEATURE:
<223> OTHER INFORMATION: VH of Hu34-39-PE

<400> SEQUENCE: 30

Gln Val Gln Leu Gln Glu Ser Gly Pro Gly Leu Val Lys Pro Ser Gln
1               5                   10                  15

Thr Leu Ser Leu Thr Cys Lys Ala Ser Gly Tyr Thr Phe Thr Asn Tyr
            20                  25                  30

Trp Ile Thr Trp Val Lys Gln Arg Pro Gly Gln Gly Leu Glu Trp Ile
        35                  40                  45

Gly Asp Ile Thr Pro Gly Arg Gly Glu Thr Asn Tyr Asn Gln Lys Phe
    50                  55                  60

Lys Gly Arg Val Thr Leu Thr Val Asp Ile Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Trp Gly Leu Arg Arg Gly Asp Tyr Trp Gly Gln Gly Thr Ser
            100                 105                 110

Val Thr Val Ser Ser
        115


<210> SEQ ID NO 31
<211> LENGTH: 121
<212> TYPE: PRT
<213> ORGANISM: Artificial sequence
<220> FEATURE:
<223> OTHER INFORMATION: VH of Hu58A-14-PE
```

<400> SEQUENCE: 31

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser Arg Phe
            20                  25                  30

Gly Met Ala Trp Val Arg Gln Thr Pro Asp Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Leu Thr Ile Ser Arg Asp Asn Ala Lys Thr Thr Leu Tyr
65                  70                  75                  80

Leu Gln Met Arg Ser Leu Lys Ser Glu Asp Thr Ala Met Tyr Tyr Cys
                85                  90                  95

Ala Arg Gln Gly Leu Leu Asp Tyr Leu Tyr Ala Leu Asp Tyr Trp Gly
            100                 105                 110

Gln Gly Thr Ala Val Thr Val Ser Ser
        115                 120
```

<210> SEQ ID NO 32
<211> LENGTH: 113
<212> TYPE: PRT
<213> ORGANISM: Artificial sequence
<220> FEATURE:
<223> OTHER INFORMATION: VL of Hu26T-31-PE

<400> SEQUENCE: 32

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Val
            20                  25                  30

Asn Asp Gln Lys Asn Tyr Leu Ala Trp Tyr Gln Gln Lys Pro Gly Lys
        35                  40                  45

Ala Pro Lys Leu Leu Ile Tyr Phe Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Ser Thr Pro Leu Thr Phe Gly Gln Gly Thr Lys Leu Glu Ile
            100                 105                 110

Lys
```

<210> SEQ ID NO 33
<211> LENGTH: 108
<212> TYPE: PRT
<213> ORGANISM: Artificial sequence
<220> FEATURE:
<223> OTHER INFORMATION: VL of Hu34-39-PE

<400> SEQUENCE: 33

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Ser Ser
            20                  25                  30

Tyr Leu Asn Trp Tyr Gln Gln Lys Ser Gly Ala Ser Pro Lys Leu Trp
        35                  40                  45
```

```
Ile Tyr Ser Thr Ser Asn Leu Ala Ser Gly Val Pro Gly Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Ala Gly Thr Lys Leu Glu Val Lys
            100                 105
```

<210> SEQ ID NO 34
<211> LENGTH: 107
<212> TYPE: PRT
<213> ORGANISM: Artificial sequence
<220> FEATURE:
<223> OTHER INFORMATION: VL of Hu58A-14-PE

<400> SEQUENCE: 34

```
Asp Ile Gln Met Thr Gln Ser Pro Ser Ser Val Ser Ala Ser Ile Gly
1               5                   10                  15

Asp Arg Val Thr Ile Thr Cys Lys Ala Ser Gln Asp Ile Asn Ser Phe
            20                  25                  30

Leu Ala Trp Phe Gln Gln Lys Pro Gly Lys Ser Pro Arg Pro Leu Ile
        35                  40                  45

Tyr Arg Ala Tyr Arg Leu Val Asp Gly Val Pro Ser Arg Phe Ser Gly
    50                  55                  60

Val Gly Ser Gly Gln Asp Tyr Ser Leu Thr Ile Ser Ser Leu Asp Tyr
65                  70                  75                  80

Glu Asp Leu Gly Ile Tyr Tyr Cys Gln Gln Tyr Val Glu Phe Pro Pro
                85                  90                  95

Thr Phe Gly Ala Gly Thr Met Leu Glu Leu Lys
            100                 105
```

<210> SEQ ID NO 35
<211> LENGTH: 357
<212> TYPE: DNA
<213> ORGANISM: Artificial sequence
<220> FEATURE:
<223> OTHER INFORMATION: Nucleotide sequence of VH of Hu26T-31-PE

<400> SEQUENCE: 35

```
caggtgcagc tggtgcagag cggagccgaa gtgaagaagc ccggtgccag cgtgaaagta     60

agctgcaagg ccagcggcta caccttcacc gactactaca tgaactgggt gaggcaggcc    120

cctggacaag gcctggagtg gatcggcagg atctaccccg gcagcggcct gacctactat    180

aacgccaagt tcaagggcag ggccaccgtg accgccgaca agtccaccag caccgtgtac    240

atggagctga gcagcctgag gagcgaggac accgccgtgt attactgcgc caggaccagc    300

tacggcagca gcttccccca cgtgtggggc cagggcacca ccgtgaccgt gagctct       357
```

<210> SEQ ID NO 36
<211> LENGTH: 351
<212> TYPE: DNA
<213> ORGANISM: Artificial sequence
<220> FEATURE:
<223> OTHER INFORMATION: Nucleotide sequence of VH of Hu34-39-PE

<400> SEQUENCE: 36

```
caggttcagc tgcaagagag cggtcccggc ctggtgaaac ccagccagac cctgagcctg     60

acctgcaagg ccagcggcta cactttcact aactactgga tcacctgggt gaagcagcga    120
```

cccggccagg gcctggagtg gatcggcgac atcacccctg ggaggggaga gaccaactac 180
aaccagaagt tcaagggcag ggtgaccctg accgtggaca tcagcgcctc cactgcctat 240
atggagctga gcagcctgag gagcgaggac accgccgtgt actactgcag caggtggggc 300
ctgaggaggg gcgattactg gggccaaggg accagcgtga ccgtgagctc t 351

<210> SEQ ID NO 37
<211> LENGTH: 363
<212> TYPE: DNA
<213> ORGANISM: Artificial sequence
<220> FEATURE:
<223> OTHER INFORMATION: Nucleotide sequence of VH of Hu58A-14-PE

<400> SEQUENCE: 37
gaggtccagc tgctggagag cggcggtggc ctcgtgcagc ccggaggcag cctgaggctg 60
agctgcgcgg caagcggctt catcttcagc aggttcggca tggcctgggt gaggcagacc 120
ccagacaaga ggctggagtg ggtggcaact atcagcagcg gaggaagtta cacctactac 180
cccgacagcg tgaagggcag gctgaccatc agtagggaca acgccaagac caccctgtac 240
ctgcagatga ggagcctgaa gagcgaggac accgccatgt actactgcgc caggcagggc 300
ctgctcgact atctgtacgc cctggactat tggggccagg gcactgccgt gaccgtgagc 360
agc 363

<210> SEQ ID NO 38
<211> LENGTH: 339
<212> TYPE: DNA
<213> ORGANISM: Artificial sequence
<220> FEATURE:
<223> OTHER INFORMATION: Nucleotide sequence of VL of Hu26T-31-PE

<400> SEQUENCE: 38
gacatccaga tgacccagag cccaagcagc ctgagcgcca gcgtgggcga cagggtgacc 60
atcacctgca agagcagcca aagcctgctg aacgtgaacg accagaagaa ctacctggcc 120
tggtatcagc agaagccggg caaggccccc aagctgctca tctactttgc cagcaccagg 180
gagagcggcg tgcccagcag gttcagcggc agcggaagtg gcaccgactt caccctcacc 240
atcagctccc tgcaacccga ggacttcgcc acctactact gtcaacagca ctacagcaca 300
cccctgacct tcggccaggg caccaagttg gagatcaag 339

<210> SEQ ID NO 39
<211> LENGTH: 324
<212> TYPE: DNA
<213> ORGANISM: Artificial sequence
<220> FEATURE:
<223> OTHER INFORMATION: Nucleotide sequence of VL of Hu34-39-PE

<400> SEQUENCE: 39
gagatcgtgc tgacccagag ccctggcacc ttgagcctga gtcccggaga gagggccacc 60
ctgagctgca gggcctcaag ctccgtgagc agcagctatc tgaattggta tcagcagaag 120
agcggagcca gccccaagct gtggatctac agcaccagca acctggcaag cggcgtgccc 180
ggcaggttca gcggcagtgg cagcgggacc agctacagcc tgaccatcag tagcgtggag 240
gccgaggacg ccgccaccta ctactgccag cagtacagcg gataccctct gaccttcgga 300
gccggaacca agttggaggt gaag 324

<210> SEQ ID NO 40
<211> LENGTH: 321

<212> TYPE: DNA
<213> ORGANISM: Artificial sequence
<220> FEATURE:
<223> OTHER INFORMATION: Nucleotide sequence of VL of Hu58A-14-PE

<400> SEQUENCE: 40
gacatccaga tgacccagag cccaagcagc gtgagcgcca gcatcggcga cagggtgacc 60
ataacctgca aggccagcca agacatcaac agcttcctgg catggttcca gcagaagccc 120
ggcaagagcc ccaggcccct gatctacagg gcctacaggc tggtagacgg ggtgcccagc 180
aggttcagcg gcgtgggcag cggccaggac tacagcctga ccatcagcag cctggactac 240
gaggacctgg gcatctacta ctgccagcag tacgtggagt tcccccccgac cttcggtgca 300 gggaccatgc tggagctgaa g 321

<210> SEQ ID NO 41
<211> LENGTH: 323
<212> TYPE: PRT
<213> ORGANISM: Artificial sequence
<220> FEATURE:
<223> OTHER INFORMATION: Amino acid sequence of CD47

<400> SEQUENCE: 41

Met Trp Pro Leu Val Ala Ala Leu Leu Leu Gly Ser Ala Cys Cys Gly
1 5 10 15

Ser Ala Gln Leu Leu Phe Asn Lys Thr Lys Ser Val Glu Phe Thr Phe
20 25 30

Cys Asn Asp Thr Val Val Ile Pro Cys Phe Val Thr Asn Met Glu Ala
35 40 45

Gln Asn Thr Thr Glu Val Tyr Val Lys Trp Lys Phe Lys Gly Arg Asp
50 55 60

Ile Tyr Thr Phe Asp Gly Ala Leu Asn Lys Ser Thr Val Pro Thr Asp
65 70 75 80

Phe Ser Ser Ala Lys Ile Glu Val Ser Gln Leu Leu Lys Gly Asp Ala
85 90 95

Ser Leu Lys Met Asp Lys Ser Asp Ala Val Ser His Thr Gly Asn Tyr
100 105 110

Thr Cys Glu Val Thr Glu Leu Thr Arg Glu Gly Glu Thr Ile Ile Glu
115 120 125

Leu Lys Tyr Arg Val Val Ser Trp Phe Ser Pro Asn Glu Asn Ile Leu
130 135 140

Ile Val Ile Phe Pro Ile Phe Ala Ile Leu Leu Phe Trp Gly Gln Phe
145 150 155 160

Gly Ile Lys Thr Leu Lys Tyr Arg Ser Gly Gly Met Asp Glu Lys Thr
165 170 175

Ile Ala Leu Leu Val Ala Gly Leu Val Ile Thr Val Ile Val Ile Val
180 185 190

Gly Ala Ile Leu Phe Val Pro Gly Glu Tyr Ser Leu Lys Asn Ala Thr
195 200 205

Gly Leu Gly Leu Ile Val Thr Ser Thr Gly Ile Leu Ile Leu Leu His
210 215 220

Tyr Tyr Val Phe Ser Thr Ala Ile Gly Leu Thr Ser Phe Val Ile Ala
225 230 235 240

Ile Leu Val Ile Gln Val Ile Ala Tyr Ile Leu Ala Val Val Gly Leu
245 250 255

Ser Leu Cys Ile Ala Ala Cys Ile Pro Met His Gly Pro Leu Leu Ile
260 265 270

```
Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
    290                 295                 300

Ala Val Glu Glu Pro Leu Asn Ala Phe Lys Glu Ser Lys Gly Met Met
305                 310                 315                 320

Asn Asp Glu


<210> SEQ ID NO 42
<211> LENGTH: 350
<212> TYPE: PRT
<213> ORGANISM: Artificial sequence
<220> FEATURE:
<223> OTHER INFORMATION: CD47-Fc fusion protein

<400> SEQUENCE: 42

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Glu Pro Lys Ser Cys Asp Lys Thr His Thr
        115                 120                 125

Cys Pro Pro Cys Pro Ala Pro Glu Leu Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300
```

```
Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
            340                 345                 350


<210> SEQ ID NO 43
<211> LENGTH: 124
<212> TYPE: PRT
<213> ORGANISM: Artificial sequence
<220> FEATURE:
<223> OTHER INFORMATION: CD47-his fusion protein

<400> SEQUENCE: 43

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp His His His His His His
        115                 120


<210> SEQ ID NO 44
<211> LENGTH: 354
<212> TYPE: PRT
<213> ORGANISM: Artificial sequence
<220> FEATURE:
<223> OTHER INFORMATION: CD47 extracellular region fusion protein

<400> SEQUENCE: 44

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Glu Pro Arg Gly Pro Thr Ile
        115                 120                 125

Lys Pro Cys Pro Pro Cys Lys Cys Pro Ala Pro Asn Leu Leu Gly Gly
    130                 135                 140
```

```
Pro Ser Val Phe Ile Phe Pro Pro Lys Ile Lys Asp Val Leu Met Ile
145                 150                 155                 160

Ser Leu Ser Pro Ile Val Thr Cys Val Val Val Asp Val Ser Glu Asp
                165                 170                 175

Asp Pro Asp Val Gln Ile Ser Trp Phe Val Asn Asn Val Glu Val His
            180                 185                 190

Thr Ala Gln Thr Gln Thr His Arg Glu Asp Tyr Asn Ser Thr Leu Arg
        195                 200                 205

Val Val Ser Ala Leu Pro Ile Gln His Gln Asp Trp Met Ser Gly Lys
    210                 215                 220

Glu Phe Lys Cys Lys Val Asn Asn Lys Asp Leu Pro Ala Pro Ile Glu
225                 230                 235                 240

Arg Thr Ile Ser Lys Pro Lys Gly Ser Val Arg Ala Pro Gln Val Tyr
                245                 250                 255

Val Leu Pro Pro Pro Glu Glu Glu Met Thr Lys Lys Gln Val Thr Leu
            260                 265                 270

Thr Cys Met Val Thr Asp Phe Met Pro Glu Asp Ile Tyr Val Glu Trp
        275                 280                 285

Thr Asn Asn Gly Lys Thr Glu Leu Asn Tyr Lys Asn Thr Glu Pro Val
    290                 295                 300

Leu Asp Ser Asp Gly Ser Tyr Phe Met Tyr Ser Lys Leu Arg Val Glu
305                 310                 315                 320

Lys Lys Asn Trp Val Glu Arg Asn Ser Tyr Ser Cys Ser Val Val His
                325                 330                 335

Glu Gly Leu His Asn His His Thr Thr Lys Ser Phe Ser Arg Thr Pro
            340                 345                 350

Gly Lys


<210> SEQ ID NO 45
<211> LENGTH: 338
<212> TYPE: PRT
<213> ORGANISM: Artificial sequence
<220> FEATURE:
<223> OTHER INFORMATION: Amino acid sequence of SIRP

<400> SEQUENCE: 45

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Ile Pro Val Gly
            20                  25                  30

Pro Ile Gln Trp Phe Arg Gly Ala Gly Pro Gly Arg Glu Leu Ile Tyr
        35                  40                  45

Asn Gln Lys Glu Gly His Phe Pro Arg Val Thr Thr Val Ser Asp Leu
    50                  55                  60

Thr Lys Arg Asn Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser Ala Pro Val Val Ser Gly Pro Ala Ala Arg Ala
        115                 120                 125

Thr Pro Gln His Thr Val Ser Phe Thr Cys Glu Ser His Gly Phe Ser
    130                 135                 140
```

Pro Arg Asp Ile Thr Leu Lys Trp Phe Lys Asn Gly Asn Glu Leu Ser
145 150 155 160

Asp Phe Gln Thr Asn Val Asp Pro Val Gly Glu Ser Val Ser Tyr Ser
165 170 175

Ile His Ser Thr Ala Lys Val Val Leu Thr Arg Glu Asp Val His Ser
180 185 190

Gln Val Ile Cys Glu Val Ala His Val Thr Leu Gln Gly Asp Pro Leu
195 200 205

Arg Gly Thr Ala Asn Leu Ser Glu Thr Ile Arg Val Pro Pro Thr Leu
210 215 220

Glu Val Thr Gln Gln Pro Val Arg Ala Glu Asn Gln Val Asn Val Thr
225 230 235 240

Cys Gln Val Arg Lys Phe Tyr Pro Gln Arg Leu Gln Leu Thr Trp Leu
245 250 255

Glu Asn Gly Asn Val Ser Arg Thr Glu Thr Ala Ser Thr Val Thr Glu
260 265 270

Asn Lys Asp Gly Thr Tyr Asn Trp Met Ser Trp Leu Leu Val Asn Val
275 280 285

Ser Ala His Arg Asp Asp Val Lys Leu Thr Cys Gln Val Glu His Asp
290 295 300

Gly Gln Pro Ala Val Ser Lys Ser His Asp Leu Lys Val Ser Ala His
305 310 315 320

Pro Lys Glu Gln Gly Ser Asn Thr Ala Ala Glu Asn Thr Gly Ser Asn
325 330 335

Glu Arg

<210> SEQ ID NO 46
<211> LENGTH: 466
<212> TYPE: PRT
<213> ORGANISM: Artificial sequence
<220> FEATURE:
<223> OTHER INFORMATION: Heavy chain amino acid sequence of AB06.12-4P

<400> SEQUENCE: 46

Met Glu Phe Gly Leu Ser Trp Leu Phe Leu Val Ala Ile Leu Lys Gly
1 5 10 15

Val Gln Cys Gln Met Gln Leu Val Gln Ser Gly Ala Glu Val Lys Lys
20 25 30

Thr Gly Ser Ser Val Lys Val Ser Cys Lys Ala Ser Gly Phe Asn Ile
35 40 45

Lys Asp Tyr Tyr Leu His Trp Val Arg Gln Ala Pro Gly Gln Ala Leu
50 55 60

Glu Trp Met Gly Trp Ile Asp Pro Asp Gln Gly Asp Thr Glu Tyr Ala
65 70 75 80

Gln Lys Phe Gln Asp Arg Val Thr Ile Thr Arg Asp Arg Ser Met Ser
85 90 95

Thr Ala Tyr Met Glu Leu Ser Ser Leu Arg Ser Glu Asp Thr Ala Met
100 105 110

Tyr Tyr Cys Asn Ala Ala Tyr Gly Ser Ser Ser Tyr Pro Met Asp Tyr
115 120 125

Trp Gly Gln Gly Thr Thr Val Thr Val Ser Ser Ala Ser Thr Lys Gly
130 135 140

Pro Ser Val Phe Pro Leu Ala Pro Cys Ser Arg Ser Thr Ser Glu Ser
145 150 155 160

Thr Ala Ala Leu Gly Cys Leu Val Lys Asp Tyr Phe Pro Glu Pro Val

```
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Pro Cys Pro Ala Pro Glu Phe Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Gln Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
            420                 425                 430

Lys Ser Arg Trp Gln Glu Gly Asn Val Phe Ser Cys Ser Val Met His
        435                 440                 445

Glu Ala Leu His Asn His Tyr Thr Gln Lys Ser Leu Ser Leu Ser Leu
    450                 455                 460

Gly Lys
465


<210> SEQ ID NO 47
<211> LENGTH: 236
<212> TYPE: PRT
<213> ORGANISM: Artificial sequence
<220> FEATURE:
<223> OTHER INFORMATION: Light chain amino acid sequence of AB06.12-4P

<400> SEQUENCE: 47

Met Asp Met Arg Val Pro Ala Gln Leu Leu Gly Leu Leu Leu Leu Trp
1               5                   10                  15

Phe Pro Gly Ser Arg Cys Asn Ile Gln Met Thr Gln Ser Pro Ser Ala
            20                  25                  30

Met Ser Ala Ser Val Gly Asp Arg Val Thr Ile Thr Cys Lys Ala Ser
        35                  40                  45

Gln Asp Ile His Arg Tyr Leu Ser Trp Phe Gln Gln Lys Pro Gly Lys
```

```
    50                  55                  60

Val Pro Lys His Leu Ile Tyr Arg Ala Asn Arg Leu Val Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
            100                 105                 110

Tyr Asp Glu Phe Pro Tyr Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235


<210> SEQ ID NO 48
<211> LENGTH: 117
<212> TYPE: PRT
<213> ORGANISM: Artificial sequence
<220> FEATURE:
<223> OTHER INFORMATION: Humanized VH of SHC025-34CHI

<400> SEQUENCE: 48

Gln Val Gln Leu Gln Glu Ser Gly Gly Gly Val Val Gln Pro Gly Arg
1               5                   10                  15

Ser Leu Arg Leu Ser Cys Lys Ala Ser Gly Tyr Thr Phe Thr Asn Tyr
            20                  25                  30

Trp Ile Thr Trp Val Lys Gln Arg Pro Gly Gln Gly Leu Glu Trp Ile
        35                  40                  45

Gly Asp Ile Thr Pro Gly Arg Gly Glu Thr Asn Tyr Asn Pro Ser Leu
    50                  55                  60

Lys Ser Arg Leu Thr Ile Ser Ile Asp Thr Ser Lys Thr Gln Phe Ser
65                  70                  75                  80

Leu Lys Leu Ser Ser Val Thr Ala Ala Asp Thr Ala Ile Tyr Tyr Cys
                85                  90                  95

Ser Arg Trp Gly Leu Arg Arg Gly Asp Tyr Trp Gly Gln Gly Thr Ser
            100                 105                 110

Val Thr Val Ser Ser
        115


<210> SEQ ID NO 49
<211> LENGTH: 117
<212> TYPE: PRT
<213> ORGANISM: Artificial sequence
<220> FEATURE:
<223> OTHER INFORMATION: Humanized VH of SHC025-34CHI

<400> SEQUENCE: 49
```

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Trp Ile Thr Trp Val Lys Gln Arg Pro Gly Gln Gly Leu Glu Trp Ile
        35                  40                  45

Gly Asp Ile Thr Pro Gly Arg Gly Glu Thr Asn Tyr Asn Pro Ser Leu
    50                  55                  60

Lys Ser Arg Leu Thr Ile Ser Ile Asp Thr Ser Lys Thr Gln Phe Ser
65                  70                  75                  80

Leu Lys Leu Ser Ser Val Thr Ala Ala Asp Thr Ala Ile Tyr Tyr Cys
                85                  90                  95

Ser Arg Trp Gly Leu Arg Arg Gly Asp Tyr Trp Gly Gln Gly Thr Ser
            100                 105                 110

Val Thr Val Ser Ser
        115
```

<210> SEQ ID NO 50
<211> LENGTH: 117
<212> TYPE: PRT
<213> ORGANISM: Artificial sequence
<220> FEATURE:
<223> OTHER INFORMATION: Humanized VH of SHC025-34CHI

<400> SEQUENCE: 50

```
Gln Val Gln Leu Gln Glu Ser Gly Gly Gly Val Val Gln Pro Gly Arg
1               5                   10                  15

Ser Leu Arg Leu Ser Cys Lys Ala Ser Gly Tyr Thr Phe Thr Asn Tyr
            20                  25                  30

Trp Ile Thr Trp Val Lys Gln Arg Pro Gly Gln Gly Leu Glu Trp Ile
        35                  40                  45

Gly Asp Ile Thr Pro Gly Arg Gly Glu Thr Asn Tyr Asn Glu Lys Phe
    50                  55                  60

Lys Ser Lys Ala Thr Leu Thr Val Asp Thr Ser Ser Ser Thr Ala Tyr
65                  70                  75                  80

Met Gln Leu Thr Ser Leu Thr Ser Glu Asp Ser Ala Val Tyr Tyr Cys
                85                  90                  95

Ser Arg Trp Gly Leu Arg Arg Gly Asp Tyr Trp Gly Gln Gly Thr Ser
            100                 105                 110

Val Thr Val Ser Ser
        115
```

<210> SEQ ID NO 51
<211> LENGTH: 118
<212> TYPE: PRT
<213> ORGANISM: Artificial sequence
<220> FEATURE:
<223> OTHER INFORMATION: Humanized VH of SHC025-34CHI

<400> SEQUENCE: 51

```
Gln Val Gln Leu Gln Glu Ser Gly Pro Gly Leu Val Arg Pro Ser Gln
1               5                   10                  15

Thr Leu Ser Leu Thr Cys Lys Ala Ser Gly Tyr Thr Phe Thr Asn Tyr
            20                  25                  30

Trp Ile Thr Trp Val Lys Gln Arg Pro Gly Gln Gly Leu Glu Trp Ile
        35                  40                  45

Gly Asp Ile Thr Pro Gly Arg Gly Glu Thr Asn Tyr Asn Pro Ser Leu
    50                  55                  60
```

```
Lys Ser Arg Leu Thr Ile Ser Ile Asp Thr Ser Lys Thr Gln Phe Ser
65                  70                  75                  80

Leu Lys Leu Ser Ser Val Thr Ala Ala Asp Thr Ala Ile Tyr Tyr Cys
                85                  90                  95

Ser Arg Trp Gly Leu Arg Arg Gly Asp Tyr Trp Gly Gln Gly Thr Ser
            100                 105                 110

Val Thr Val Ser Ser His
        115


<210> SEQ ID NO 52
<211> LENGTH: 117
<212> TYPE: PRT
<213> ORGANISM: Artificial sequence
<220> FEATURE:
<223> OTHER INFORMATION: Humanized VH of SHC025-34CHI

<400> SEQUENCE: 52

Gln Val Gln Leu Gln Glu Ser Gly Pro Gly Leu Val Lys Pro Ser Gln
1               5                   10                  15

Thr Leu Ser Leu Thr Cys Lys Ala Ser Gly Tyr Thr Phe Thr Asn Tyr
            20                  25                  30

Trp Ile Thr Trp Val Lys Gln Arg Pro Gly Gln Gly Leu Glu Trp Ile
        35                  40                  45

Gly Asp Ile Thr Pro Gly Arg Gly Glu Thr Asn Tyr Asn Gln Lys Phe
    50                  55                  60

Lys Gly Arg Val Thr Leu Thr Val Asp Ile Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Trp Gly Leu Arg Arg Gly Asp Tyr Trp Gly Gln Gly Thr Ser
            100                 105                 110

Val Thr Val Ser Ser
        115


<210> SEQ ID NO 53
<211> LENGTH: 117
<212> TYPE: PRT
<213> ORGANISM: Artificial sequence
<220> FEATURE:
<223> OTHER INFORMATION: Humanized VH of SHC025-34CHI

<400> SEQUENCE: 53

Gln Val Gln Leu Gln Glu Ser Gly Gly Gly Val Val Gln Pro Gly Arg
1               5                   10                  15

Ser Leu Arg Leu Ser Cys Lys Ala Ser Gly Tyr Thr Phe Thr Asn Tyr
            20                  25                  30

Trp Ile Thr Trp Val Lys Gln Arg Pro Gly Gln Gly Leu Glu Trp Ile
        35                  40                  45

Gly Asp Ile Thr Pro Gly Arg Gly Glu Thr Asn Tyr Asn Gln Lys Phe
    50                  55                  60

Lys Gly Arg Val Thr Leu Thr Val Asp Ile Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Trp Gly Leu Arg Arg Gly Asp Tyr Trp Gly Gln Gly Thr Ser
            100                 105                 110

Val Thr Val Ser Ser
```

115

<210> SEQ ID NO 54
<211> LENGTH: 108
<212> TYPE: PRT
<213> ORGANISM: Artificial sequence
<220> FEATURE:
<223> OTHER INFORMATION: Humanized VL of SHC025-34CHI

<400> SEQUENCE: 54

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Ser Ser
            20                  25                  30

Tyr Leu Asn Trp Tyr Gln Gln Lys Ser Gly Ala Ser Pro Lys Leu Trp
        35                  40                  45

Ile Tyr Ser Thr Ser Asn Leu Ala Ser Gly Val Pro Gly Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Ala Gly Thr Lys Leu Glu Val Lys
            100                 105
```

<210> SEQ ID NO 55
<211> LENGTH: 108
<212> TYPE: PRT
<213> ORGANISM: Artificial sequence
<220> FEATURE:
<223> OTHER INFORMATION: Humanized VL of SHC025-34CHI

<400> SEQUENCE: 55

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Ser Ser
            20                  25                  30

Tyr Leu Asn Trp Tyr Gln Gln Lys Ser Gly Ala Ser Pro Lys Leu Trp
        35                  40                  45

Ile Tyr Ser Thr Ser Asn Leu Ala Ser Gly Val Pro Ser Arg Phe Ser
    50                  55                  60

Gly Ser Gly Ser Gly Thr Ser Phe Thr Leu Thr Ile Ser Ser Leu Gln
65                  70                  75                  80

Pro Glu Asp Ala Ala Thr Tyr Tyr Cys Gln Gln Tyr Ser Gly Tyr Pro
                85                  90                  95

Leu Thr Phe Gly Ala Gly Thr Lys Leu Glu Val Lys
            100                 105
```

<210> SEQ ID NO 56
<211> LENGTH: 108
<212> TYPE: PRT
<213> ORGANISM: Artificial sequence
<220> FEATURE:
<223> OTHER INFORMATION: Humanized VL of SHC025-34CHI

<400> SEQUENCE: 56

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Ser Ser
            20                  25                  30
```

```
Tyr Leu Asn Trp Tyr Gln Gln Lys Ser Gly Ala Ser Pro Lys Leu Trp
        35                  40                  45

Ile Tyr Ser Thr Ser Asn Leu Ala Ser Gly Val Pro Gly Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Ala Gly Thr Lys Leu Glu Val Lys
            100                 105


<210> SEQ ID NO 57
<211> LENGTH: 108
<212> TYPE: PRT
<213> ORGANISM: Artificial sequence
<220> FEATURE:
<223> OTHER INFORMATION: Humanized VL of SHC025-34CHI

<400> SEQUENCE: 57

Glu Ile Val Met Thr Gln Ser Pro Ala Thr Leu Ser Leu Ser Pro Gly
1               5                   10                  15

Glu Arg Ala Thr Leu Ser Cys Arg Ala Ser Ser Ser Val Ser Ser Ser
            20                  25                  30

Tyr Leu Asn Trp Tyr Gln Gln Lys Ser Gly Ala Ser Pro Lys Leu Trp
        35                  40                  45

Ile Tyr Ser Thr Ser Asn Leu Ala Ser Gly Val Pro Gly Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Ala Gly Thr Lys Leu Glu Val Lys
            100                 105


<210> SEQ ID NO 58
<211> LENGTH: 121
<212> TYPE: PRT
<213> ORGANISM: Artificial sequence
<220> FEATURE:
<223> OTHER INFORMATION: Humanized VH of SHC025-58CHI-A

<400> SEQUENCE: 58

Glu Val Gln Leu Val Glu Ser Gly Gly Asp Leu Val Glu Pro Gly Gly
1               5                   10                  15

Ser Leu Lys Leu Ser Cys Ala Ala Ser Gly Phe Ile Phe Ser Arg Phe
            20                  25                  30

Gly Met Ala Trp Val Arg Gln Thr Pro Asp Lys Arg Leu Glu Trp Val
        35                  40                  45

Ala Thr Ile Ser Ser Gly Gly Ser Tyr Thr Arg Tyr Ser Pro Ser Phe
    50                  55                  60

Gln Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
                85                  90                  95

Ala Arg Gln Gly Leu Leu Asp Tyr Leu Tyr Ala Leu Asp Tyr Trp Gly
            100                 105                 110

Gln Gly Thr Ala Val Thr Val Ser Ser
```

115 120

<210> SEQ ID NO 59
<211> LENGTH: 121
<212> TYPE: PRT
<213> ORGANISM: Artificial sequence
<220> FEATURE:
<223> OTHER INFORMATION: Humanized VH of SHC025-58CHI-A

<400> SEQUENCE: 59

Gln Val Gln Leu Val Glu Ser Gly Gly Gly Val Val Gln Pro Gly Arg
1 5 10 15

Ser Leu Arg Leu Ser Cys Ala Ala Ser Gly Phe Ile Phe Ser Arg Phe
20 25 30

Gly Met Ala Trp Val Arg Gln Thr Pro Asp Lys Arg Leu Glu Trp Val
35 40 45

Ala Thr Ile Ser Ser Gly Gly Ser Tyr Thr Tyr Tyr Pro Asp Ser Val
50 55 60

Lys Gly Arg Leu Thr Ile Ser Arg Asp Asn Ala Lys Thr Thr Leu Tyr
65 70 75 80

Leu Gln Met Arg Ser Leu Lys Ser Glu Asp Thr Ala Met Tyr Tyr Cys
85 90 95

Ala Arg Gln Gly Leu Leu Asp Tyr Leu Tyr Ala Leu Asp Tyr Trp Gly
100 105 110

Gln Gly Thr Ala Val Thr Val Ser Ser
115 120

<210> SEQ ID NO 60
<211> LENGTH: 121
<212> TYPE: PRT
<213> ORGANISM: Artificial sequence
<220> FEATURE:
<223> OTHER INFORMATION: Humanized VH of SHC025-58CHI-A

<400> SEQUENCE: 60

Leu Val Gln Leu Val Glu Ser Gly Gly Gly Leu Ile Gln Pro Gly Gly
1 5 10 15

Ser Leu Arg Leu Ser Cys Ala Ala Ser Gly Phe Ile Phe Ser Arg Phe
20 25 30

Gly Met Ala Trp Val Arg Gln Thr Pro Asp Lys Arg Leu Glu Trp Val
35 40 45

Ala Thr Ile Ser Ser Gly Gly Ser Tyr Thr Asn Tyr Asn Gln Lys Phe
50 55 60

Lys Gly Arg Val Thr Leu Thr Val Asp Ile Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Gln Gly Leu Leu Asp Tyr Leu Tyr Ala Leu Asp Tyr Trp Gly
100 105 110

Gln Gly Thr Ala Val Thr Val Ser Ser
115 120

<210> SEQ ID NO 61
<211> LENGTH: 121
<212> TYPE: PRT
<213> ORGANISM: Artificial sequence
<220> FEATURE:
<223> OTHER INFORMATION: Humanized VH of SHC025-58CHI-A

<400> SEQUENCE: 61

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser Arg Phe
            20                  25                  30

Gly Met Ala Trp Val Arg Gln Thr Pro Asp Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Leu Thr Ile Ser Arg Asp Asn Ala Lys Thr Thr Leu Tyr
65                  70                  75                  80

Leu Gln Met Arg Ser Leu Lys Ser Glu Asp Thr Ala Met Tyr Tyr Cys
                85                  90                  95

Ala Arg Gln Gly Leu Leu Asp Tyr Leu Tyr Ala Leu Asp Tyr Trp Gly
            100                 105                 110

Gln Gly Thr Ala Val Thr Val Ser Ser
        115                 120
```

<210> SEQ ID NO 62
<211> LENGTH: 121
<212> TYPE: PRT
<213> ORGANISM: Artificial sequence
<220> FEATURE:
<223> OTHER INFORMATION: Humanized VH of SHC025-58CHI-A

<400> SEQUENCE: 62

```
Leu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Phe Ser Arg Phe
            20                  25                  30

Gly Met Ala Trp Val Arg Gln Thr Pro Asp Lys Arg Leu Glu Trp Val
        35                  40                  45

Ala Thr Ile Ser Ser Gly Gly Ser Tyr Thr Arg Tyr Ser Pro Ser Phe
    50                  55                  60

Gln Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
                85                  90                  95

Ala Arg Gln Gly Leu Leu Asp Tyr Leu Tyr Ala Leu Asp Tyr Trp Gly
            100                 105                 110

Gln Gly Thr Ala Val Thr Val Ser Ser
        115                 120
```

<210> SEQ ID NO 63
<211> LENGTH: 121
<212> TYPE: PRT
<213> ORGANISM: Artificial sequence
<220> FEATURE:
<223> OTHER INFORMATION: Humanized VH of SHC025-58CHI-A

<400> SEQUENCE: 63

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser Arg Phe
            20                  25                  30

Gly Met Ala Trp Val Arg Gln Thr Pro Asp Lys Arg Leu Glu Trp Val
        35                  40                  45

Ala Thr Ile Ser Ser Gly Gly Ser Tyr Thr Arg Tyr Ser Pro Ser Phe
```

```
    50                  55                  60

Gln Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
                85                  90                  95

Ala Arg Gln Gly Leu Leu Asp Tyr Leu Tyr Ala Leu Asp Tyr Trp Gly
            100                 105                 110

Gln Gly Thr Ala Val Thr Val Ser Ser
        115                 120


<210> SEQ ID NO 64
<211> LENGTH: 107
<212> TYPE: PRT
<213> ORGANISM: Artificial sequence
<220> FEATURE:
<223> OTHER INFORMATION: Humanized VL of SHC025-58CHI-A

<400> SEQUENCE: 64

Asp Ile Gln Met Thr Gln Ser Pro Ser Ser Val Ser Ala Ser Ile Gly
1               5                   10                  15

Asp Arg Val Thr Ile Thr Cys Lys Ala Ser Gln Asp Ile Asn Ser Phe
            20                  25                  30

Leu Thr Trp Phe Gln Gln Lys Pro Gly Lys Ser Pro Arg Pro Leu Ile
        35                  40                  45

Tyr Arg Ala Tyr Arg Leu Val Asp Gly Val Pro Ser Arg Phe Ser Gly
    50                  55                  60

Val Gly Ser Gly Gln Asp Tyr Ser Leu Thr Ile Ser Ser Leu Asp Tyr
65                  70                  75                  80

Glu Asp Leu Gly Ile Tyr Tyr Cys Gln Gln Tyr Val Glu Phe Pro Pro
                85                  90                  95

Thr Phe Gly Ala Gly Thr Met Leu Glu Leu Lys
            100                 105


<210> SEQ ID NO 65
<211> LENGTH: 107
<212> TYPE: PRT
<213> ORGANISM: Artificial sequence
<220> FEATURE:
<223> OTHER INFORMATION: Humanized VL of SHC025-58CHI-A

<400> SEQUENCE: 65

Asp Ile Gln Met Thr Gln Ser Pro Ser Ser Val Ser Ala Ser Ile Gly
1               5                   10                  15

Asp Arg Val Thr Ile Thr Cys Lys Ala Ser Gln Asp Ile Asn Ser Phe
            20                  25                  30

Leu Thr Trp Phe Gln Gln Lys Pro Gly Lys Ser Pro Arg Pro Leu Ile
        35                  40                  45

Tyr Arg Ala Tyr Arg Leu Val Asp Gly Val Pro Ser Arg Phe Ser Gly
    50                  55                  60

Ser Gly Ser Gly Thr Tyr Phe Thr Leu Thr Ile Ser Ser Leu Gln Ala
65                  70                  75                  80

Glu Asp Phe Ala Val Tyr Tyr Cys Gln Gln Tyr Val Glu Phe Pro Pro
                85                  90                  95

Thr Phe Gly Ala Gly Thr Met Leu Glu Leu Lys
            100                 105


<210> SEQ ID NO 66
<211> LENGTH: 107
```

<212> TYPE: PRT
<213> ORGANISM: Artificial sequence
<220> FEATURE:
<223> OTHER INFORMATION: Humanized VL of SHC025-58CHI-A

<400> SEQUENCE: 66

Asp Ile Lys Met Ile Gln Ser Pro Ser Ser Met Tyr Ala Gly Leu Gly
1 5 10 15

Glu Arg Val Thr Phe Asn Cys Lys Ala Ser Gln Asp Ile Asn Ser Phe
20 25 30

Leu Thr Trp Phe Gln Gln Lys Pro Gly Lys Ser Pro Arg Pro Leu Ile
35 40 45

Tyr Arg Ala Tyr Arg Leu Val Asp Gly Val Pro Ser Arg Phe Ser Gly
50 55 60

Ser Gly Ser Gly Thr Tyr Phe Thr Leu Thr Ile Ser Ser Leu Gln Ala
65 70 75 80

Glu Asp Phe Ala Val Tyr Tyr Cys Gln Gln Tyr Val Glu Phe Pro Pro
85 90 95

Thr Phe Gly Ala Gly Thr Met Leu Glu Leu Lys
100 105

<210> SEQ ID NO 67
<211> LENGTH: 107
<212> TYPE: PRT
<213> ORGANISM: Artificial sequence
<220> FEATURE:
<223> OTHER INFORMATION: Humanized VL of SHC025-58CHI-A

<400> SEQUENCE: 67

Asp Ile Gln Met Thr Gln Ser Pro Ser Ser Val Ser Ala Ser Ile Gly
1 5 10 15

Asp Arg Val Thr Ile Thr Cys Lys Ala Ser Gln Asp Ile Asn Ser Phe
20 25 30

Leu Thr Trp Phe Gln Gln Lys Pro Gly Lys Ser Pro Arg Pro Leu Ile
35 40 45

Tyr Arg Ala Tyr Arg Leu Val Asp Gly Val Pro Asp Arg Phe Ser Gly
50 55 60

Ser Gly Ser Gly Thr Asp Phe Thr Leu Thr Ile Ser Ser Leu Gln Ala
65 70 75 80

Glu Asp Val Ala Val Tyr Tyr Cys Gln Gln Tyr Val Glu Phe Pro Pro
85 90 95

Thr Phe Gly Ala Gly Thr Met Leu Glu Leu Lys
100 105

<210> SEQ ID NO 68
<211> LENGTH: 107
<212> TYPE: PRT
<213> ORGANISM: Artificial sequence
<220> FEATURE:
<223> OTHER INFORMATION: Humanized VL of SHC025-58CHI-A

<400> SEQUENCE: 68

Asp Ile Lys Met Ile Gln Ser Pro Ser Ser Met Tyr Ala Gly Leu Gly
1 5 10 15

Glu Arg Val Thr Phe Asn Cys Lys Ala Ser Gln Asp Ile Asn Ser Phe
20 25 30

Leu Thr Trp Phe Gln Gln Lys Pro Gly Lys Ser Pro Arg Pro Leu Ile
35 40 45

Tyr Arg Ala Tyr Arg Leu Val Asp Gly Val Pro Ser Arg Phe Ser Gly

```
    50                  55                  60

Val Gly Ser Gly Gln Asp Tyr Ser Leu Thr Ile Ser Ser Leu Asp Tyr
65                  70                  75                  80

Glu Asp Leu Gly Ile Tyr Tyr Cys Gln Gln Tyr Val Glu Phe Pro Pro
                85                  90                  95

Thr Phe Gly Ala Gly Thr Met Leu Glu Leu Lys
            100                 105


<210> SEQ ID NO 69
<211> LENGTH: 119
<212> TYPE: PRT
<213> ORGANISM: Artificial sequence
<220> FEATURE:
<223> OTHER INFORMATION: Humanized VH of SHC025-26CHI-T

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Arg Ile Tyr Pro Gly Ser Gly Leu Thr Tyr Tyr Asn Ala Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Ser Tyr Gly Ser Ser Phe Pro His Val Trp Gly Gln Gly
            100                 105                 110

Thr Thr Val Thr Val Ser Ser
        115


<210> SEQ ID NO 70
<211> LENGTH: 119
<212> TYPE: PRT
<213> ORGANISM: Artificial sequence
<220> FEATURE:
<223> OTHER INFORMATION: Humanized VH of SHC025-26CHI-T

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Arg Ile Tyr Pro Gly Ser Gly Leu Thr Tyr Tyr Asn Ala Lys Phe
    50                  55                  60

Lys Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Ser Tyr Gly Ser Ser Phe Pro His Val Trp Gly Gln Gly
            100                 105                 110

Thr Thr Val Thr Val Ser Ser
        115
```

<210> SEQ ID NO 71
<211> LENGTH: 119
<212> TYPE: PRT
<213> ORGANISM: Artificial sequence
<220> FEATURE:
<223> OTHER INFORMATION: Humanized VH of SHC025-26CHI-T

<400> SEQUENCE: 71

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

Gly Arg Ile Tyr Pro Gly Ser Gly Leu Thr Tyr Tyr Asn Ala Lys Phe
    50                  55                  60

Lys Gly Arg Ala Thr Val Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Ser Tyr Gly Ser Ser Phe Pro His Val Trp Gly Gln Gly
            100                 105                 110

Thr Thr Val Thr Val Ser Ser
        115
```

<210> SEQ ID NO 72
<211> LENGTH: 119
<212> TYPE: PRT
<213> ORGANISM: Artificial sequence
<220> FEATURE:
<223> OTHER INFORMATION: Humanized VH of SHC025-26CHI-T

<400> SEQUENCE: 72

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

Gly Arg Ile Tyr Pro Gly Ser Gly Leu Thr Tyr Tyr Asn Ala Lys Phe
    50                  55                  60

Lys Gly Arg Ala Thr Val Thr Ala Asp Lys Ser Thr Ser Thr Val Tyr
65                  70                  75                  80

Met Glu Leu Ser Ser Leu Arg Ser Glu Asp Thr Ala Val Tyr Phe Cys
                85                  90                  95

Ala Arg Thr Ser Tyr Gly Ser Ser Phe Pro His Val Trp Gly Gln Gly
            100                 105                 110

Thr Thr Val Thr Val Ser Ser
        115
```

<210> SEQ ID NO 73
<211> LENGTH: 113
<212> TYPE: PRT
<213> ORGANISM: Artificial sequence
<220> FEATURE:
<223> OTHER INFORMATION: Humanized VL of SHC025-26CHI-T

<400> SEQUENCE: 73

```
Asp Ile Gln Met Thr Gln Ser Pro Ser Ser Leu Ser Ala Ser Val Gly
```

```
1               5                   10                  15

Asp Arg Val Thr Ile Thr Cys Lys Ser Ser Gln Ser Leu Leu Asn Val
            20                  25                  30

Asn Asp Gln Lys Asn Tyr Leu Ala Trp Tyr Gln Gln Lys Pro Gly Lys
        35                  40                  45

Ala Pro Lys Leu Leu Ile Tyr Phe Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Ser Thr Pro Leu Thr Phe Gly Gln Gly Thr Lys Leu Glu Ile
            100                 105                 110

Lys


<210> SEQ ID NO 74
<211> LENGTH: 113
<212> TYPE: PRT
<213> ORGANISM: Artificial sequence
<220> FEATURE:
<223> OTHER INFORMATION: Humanized VL of SHC025-26CHI-T

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Val
            20                  25                  30

Asn Asp Gln Lys Asn Tyr Leu Ala Trp Tyr Gln Gln Lys Pro Gly Lys
        35                  40                  45

Ala Pro Lys Leu Leu Val Tyr Phe Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Phe Cys Gln Gln
                85                  90                  95

His Tyr Ser Thr Pro Leu Thr Phe Gly Gln Gly Thr Lys Leu Glu Ile
            100                 105                 110

Lys


<210> SEQ ID NO 75
<211> LENGTH: 10
<212> TYPE: PRT
<213> ORGANISM: Artificial sequence
<220> FEATURE:
<223> OTHER INFORMATION: H2CDR1

<400> SEQUENCE: 75

Gly Asp Ser Ile Thr Ser Gly Tyr Trp Asn
1               5                   10


<210> SEQ ID NO 76
<211> LENGTH: 16
<212> TYPE: PRT
<213> ORGANISM: Artificial sequence
<220> FEATURE:
<223> OTHER INFORMATION: H2CDR2

<400> SEQUENCE: 76

Tyr Ile Ser Tyr Thr Gly Ser Thr Tyr Tyr Asn Leu Ser Leu Lys Ser
```

1 5 10 15

<210> SEQ ID NO 77
<211> LENGTH: 10
<212> TYPE: PRT
<213> ORGANISM: Artificial sequence
<220> FEATURE:
<223> OTHER INFORMATION: H2CDR3

<400> SEQUENCE: 77

Tyr Ile Leu Trp Leu Arg His Phe Asp Tyr
1 5 10

<210> SEQ ID NO 78
<211> LENGTH: 17
<212> TYPE: PRT
<213> ORGANISM: Artificial sequence
<220> FEATURE:
<223> OTHER INFORMATION: L2CDR1

<400> SEQUENCE: 78

Lys Ser Ser Gln Ser Leu Leu Tyr Ser Ser Asn Gln Lys Asn Ser Leu
1 5 10 15

Ala

<210> SEQ ID NO 79
<211> LENGTH: 7
<212> TYPE: PRT
<213> ORGANISM: Artificial sequence
<220> FEATURE:
<223> OTHER INFORMATION: L2CDR2

<400> SEQUENCE: 79

Trp Ala Ser Thr Arg Glu Ser
1 5

<210> SEQ ID NO 80
<211> LENGTH: 9
<212> TYPE: PRT
<213> ORGANISM: Artificial sequence
<220> FEATURE:
<223> OTHER INFORMATION: L2CDR3

<400> SEQUENCE: 80

Gln Gln Tyr Tyr Gly Tyr Pro Leu Thr
1 5

<210> SEQ ID NO 81
<211> LENGTH: 5
<212> TYPE: PRT
<213> ORGANISM: Artificial sequence
<220> FEATURE:
<223> OTHER INFORMATION: H2CDR1

<400> SEQUENCE: 81

Ser Asp Tyr Trp Asn
1 5

<210> SEQ ID NO 82
<211> LENGTH: 16
<212> TYPE: PRT
<213> ORGANISM: Artificial sequence
<220> FEATURE:
<223> OTHER INFORMATION: H2CDR2

<400> SEQUENCE: 82

Tyr Ile Ser Tyr Thr Gly Ser Thr Tyr Tyr Asn Pro Ser Leu Lys Arg
1 5 10 15

<210> SEQ ID NO 83
<211> LENGTH: 10
<212> TYPE: PRT
<213> ORGANISM: Artificial sequence
<220> FEATURE:
<223> OTHER INFORMATION: H2CDR3

<400> SEQUENCE: 83

Tyr Arg Asp Trp Pro Gly Tyr Phe Asp Val
1 5 10

<210> SEQ ID NO 84
<211> LENGTH: 11
<212> TYPE: PRT
<213> ORGANISM: Artificial sequence
<220> FEATURE:
<223> OTHER INFORMATION: L2CDR1

<400> SEQUENCE: 84

Arg Ala Ser Lys Ser Ile Arg Lys Phe Leu Ala
1 5 10

<210> SEQ ID NO 85
<211> LENGTH: 7
<212> TYPE: PRT
<213> ORGANISM: Artificial sequence
<220> FEATURE:
<223> OTHER INFORMATION: L2CDR2

<400> SEQUENCE: 85

Ser Gly Ser Thr Leu Gln Ser
1 5

<210> SEQ ID NO 86
<211> LENGTH: 9
<212> TYPE: PRT
<213> ORGANISM: Artificial sequence
<220> FEATURE:
<223> OTHER INFORMATION: L2CDR3

<400> SEQUENCE: 86

Gln His Tyr Asn Glu Tyr Pro Phe Thr
1 5

<210> SEQ ID NO 87
<211> LENGTH: 10
<212> TYPE: PRT
<213> ORGANISM: Artificial sequence
<220> FEATURE:
<223> OTHER INFORMATION: H2CDR1

<400> SEQUENCE: 87

Gly Tyr Thr Phe Thr Arg Asn Thr Met His
1 5 10

<210> SEQ ID NO 88
<211> LENGTH: 17
<212> TYPE: PRT
<213> ORGANISM: Artificial sequence
<220> FEATURE:
<223> OTHER INFORMATION: H2CDR2

<400> SEQUENCE: 88

Phe Ile Asp Pro His Asn Thr Tyr Thr Arg Tyr Asn Gln Lys Phe Lys 1 5 10 15

Asp

<210> SEQ ID NO 89
<211> LENGTH: 5
<212> TYPE: PRT
<213> ORGANISM: Artificial sequence
<220> FEATURE:
<223> OTHER INFORMATION: H2CDR3

<400> SEQUENCE: 89

Trp Pro Met Asp Tyr
1 5

<210> SEQ ID NO 90
<211> LENGTH: 17
<212> TYPE: PRT
<213> ORGANISM: Artificial sequence
<220> FEATURE:
<223> OTHER INFORMATION: L2CDR1

<400> SEQUENCE: 90

Lys Ser Ser Gln Ser Leu Ser Trp Ser Glu Asn Gln Asn Asn Tyr Leu
1 5 10 15

Ser

<210> SEQ ID NO 91
<211> LENGTH: 7
<212> TYPE: PRT
<213> ORGANISM: Artificial sequence
<220> FEATURE:
<223> OTHER INFORMATION: L2CDR2

<400> SEQUENCE: 91

Gly Ala Ser Ile Arg Glu Ser
1 5

<210> SEQ ID NO 92
<211> LENGTH: 11
<212> TYPE: PRT
<213> ORGANISM: Artificial sequence
<220> FEATURE:
<223> OTHER INFORMATION: L2CDR3

<400> SEQUENCE: 92

Gln His Asn His Gly Ser Phe Leu Pro Tyr Thr
1 5 10

<210> SEQ ID NO 93
<211> LENGTH: 5
<212> TYPE: PRT
<213> ORGANISM: Artificial sequence
<220> FEATURE:
<223> OTHER INFORMATION: H2CDR1

<400> SEQUENCE: 93

Ser Asn Trp Met Asn
1 5

<210> SEQ ID NO 94
<211> LENGTH: 17
<212> TYPE: PRT
<213> ORGANISM: Artificial sequence
<220> FEATURE:
<223> OTHER INFORMATION: H2CDR2

<400> SEQUENCE: 94

Met Ile His Leu Tyr Asp Ser Glu Thr Lys Leu Asn Pro Asn Phe Gln
1 5 10 15

Asp

<210> SEQ ID NO 95
<211> LENGTH: 9
<212> TYPE: PRT
<213> ORGANISM: Artificial sequence
<220> FEATURE:
<223> OTHER INFORMATION: H2CDR3

<400> SEQUENCE: 95

Ser Ala Gly Asn Tyr Arg Phe Ala Tyr
1 5

<210> SEQ ID NO 96
<211> LENGTH: 11
<212> TYPE: PRT
<213> ORGANISM: Artificial sequence
<220> FEATURE:
<223> OTHER INFORMATION: L2CDR1

<400> SEQUENCE: 96

Lys Ala Ser Gln Ser Val Ser Asn Glu Val Ala
1 5 10

<210> SEQ ID NO 97
<211> LENGTH: 7
<212> TYPE: PRT
<213> ORGANISM: Artificial sequence
<220> FEATURE:
<223> OTHER INFORMATION: L2CDR2

<400> SEQUENCE: 97

Ser Ala Ser Ser Arg Tyr Thr
1 5

<210> SEQ ID NO 98
<211> LENGTH: 9
<212> TYPE: PRT
<213> ORGANISM: Artificial sequence
<220> FEATURE:
<223> OTHER INFORMATION: L2CDR3

<400> SEQUENCE: 98

Gln Gln His Tyr Ser Ser Pro Leu Thr
1 5

<210> SEQ ID NO 99
<211> LENGTH: 118
<212> TYPE: PRT
<213> ORGANISM: Artificial sequence
<220> FEATURE:
<223> OTHER INFORMATION: VH of anti-PD-L1

<400> SEQUENCE: 99

Glu Val Gln Leu Gln Glu Ser Gly Pro Ser Leu Val Lys Pro Ser Gln
1 5 10 15

Thr Leu Ser Leu Thr Cys Ser Val Thr Gly Asp Ser Ile Thr Ser Gly
20 25 30

Tyr Trp Asn Trp Ile Arg Lys Phe Pro Gly Asn Lys Leu Glu Tyr Met
35 40 45

Gly Tyr Ile Ser Tyr Thr Gly Ser Thr Tyr Tyr Asn Leu Ser Leu Lys

```
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Ile Leu Trp Leu Arg His Phe Asp Tyr Trp Gly Gln Gly Thr
            100                 105                 110

Thr Leu Thr Val Ser Ser
        115


<210> SEQ ID NO 100
<211> LENGTH: 118
<212> TYPE: PRT
<213> ORGANISM: Artificial sequence
<220> FEATURE:
<223> OTHER INFORMATION: VH of anti-PD-L1

<400> SEQUENCE: 100

Glu Val Gln Leu Gln Glu Ser Gly Pro Gly Leu Ala Lys Pro Ser Gln
1               5                   10                  15

Thr Leu Ser Leu Thr Cys Ser Val Thr Gly Tyr Ser Ile Thr Ser Asp
            20                  25                  30

Tyr Trp Asn Trp Ile Arg Lys Phe Pro Gly Asn Lys Leu Glu Tyr Met
        35                  40                  45

Gly Tyr Ile Ser Tyr Thr Gly Ser Thr Tyr Tyr Asn Pro Ser Leu Lys
    50                  55                  60

Arg Arg Val Ser Ile Thr Arg Asp Thr Ser Lys Asn Asn Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Arg Asp Trp Pro Gly Tyr Phe Asp Val Trp Gly Ala Gly Thr
            100                 105                 110

Thr Val Thr Val Ser Ser
        115


<210> SEQ ID NO 101
<211> LENGTH: 114
<212> TYPE: PRT
<213> ORGANISM: Artificial sequence
<220> FEATURE:
<223> OTHER INFORMATION: VH of anti-PD-L1

<400> SEQUENCE: 101

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Asn
            20                  25                  30

Thr Met His Trp Ile Lys Gln Arg Pro Gly Gln Gly Leu Glu Trp Ile
        35                  40                  45

Gly Phe Ile Asp Pro His Asn Thr Tyr Thr Arg Tyr Asn Gln Lys Phe
    50                  55                  60

Lys Asp Arg Ala Thr Leu Thr Ala Asp Lys Ser Ser Ser Thr Ala Tyr
65                  70                  75                  80

Met Gln Leu Ser Ser Leu Ser Ser Glu Asp Ser Ala Val Tyr Tyr Cys
                85                  90                  95

Ala Arg Trp Pro Met Asp Tyr Trp Gly Gln Gly Thr Ser Val Thr Val
            100                 105                 110
```

Ser Ser

<210> SEQ ID NO 102
<211> LENGTH: 118
<212> TYPE: PRT
<213> ORGANISM: Artificial sequence
<220> FEATURE:
<223> OTHER INFORMATION: VH of anti-PD-L1

<400> SEQUENCE: 102

```
Gln Val Gln Leu Gln Gln Pro Gly Ala Glu Leu Val Arg Pro Gly Thr
1               5                   10                  15

Ser Val Asn Leu Ser Cys Lys Ala Ser Gly Tyr Ser Phe Thr Ser Asn
            20                  25                  30

Trp Met Asn Trp Val Lys Gln Arg Pro Gly Gln Gly Leu Glu Trp Ile
        35                  40                  45

Gly Met Ile His Leu Tyr Asp Ser Glu Thr Lys Leu Asn Pro Asn Phe
    50                  55                  60

Gln Asp Lys Ala Thr Leu Thr Val Asp Lys Ser Ser Ser Ile Ala Tyr
65                  70                  75                  80

Met Gln Leu Ser Ser Pro Thr Ser Glu Asp Ser Ala Val Tyr Tyr Cys
                85                  90                  95

Ala Arg Ser Ala Gly Asn Tyr Arg Phe Ala Tyr Trp Gly Gln Gly Thr
            100                 105                 110

Leu Val Thr Val Ser Ala
        115
```

<210> SEQ ID NO 103
<211> LENGTH: 113
<212> TYPE: PRT
<213> ORGANISM: Artificial sequence
<220> FEATURE:
<223> OTHER INFORMATION: VL of anti-PD-L1

<400> SEQUENCE: 103

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Ser Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Gly Tyr Pro Leu Thr Phe Gly Ala Gly Thr Lys Leu Glu Leu
            100                 105                 110

Lys
```

<210> SEQ ID NO 104
<211> LENGTH: 107
<212> TYPE: PRT
<213> ORGANISM: Artificial sequence
<220> FEATURE:
<223> OTHER INFORMATION: VL of anti-PD-L1

<400> SEQUENCE: 104

Asp Val Gln Ile Thr Gln Ser Pro Ser Tyr Leu Ala Ala Ser Pro Gly
1 5 10 15

Glu Thr Ile Thr Ile Asn Cys Arg Ala Ser Lys Ser Ile Arg Lys Phe
20 25 30

Leu Ala Trp Tyr Gln Glu Lys Pro Gly Lys Thr Asn Lys Leu Leu Ile
35 40 45

Tyr Ser Gly Ser Thr Leu Gln Ser Gly Ile Pro Ser Arg Phe Ser Gly
50 55 60

Ser Gly Ser Gly Thr Asp Phe Thr Leu Thr Ile Ser Thr Leu Glu Pro
65 70 75 80

Glu Asp Phe Ala Val Tyr Tyr Cys Gln His Tyr Asn Glu Tyr Pro Phe
85 90 95

Thr Phe Gly Gly Gly Thr Lys Leu Glu Ile Lys
100 105

<210> SEQ ID NO 105
<211> LENGTH: 115
<212> TYPE: PRT
<213> ORGANISM: Artificial sequence
<220> FEATURE:
<223> OTHER INFORMATION: VL of anti-PD-L1

<400> SEQUENCE: 105

Asp Ile Val Met Thr Gln Phe Pro Ser Ser Leu Ala Val Thr Ala Gly
1 5 10 15

Glu Lys Val Thr Met Arg Cys Lys Ser Ser Gln Ser Leu Ser Trp Ser
20 25 30

Glu Asn Gln Asn Asn Tyr Leu Ser Trp Tyr Gln Gln Lys Gln Gly Gln
35 40 45

Pro Pro Lys Leu Leu Ile Tyr Gly Ala Ser Ile Arg Glu Ser Trp Val
50 55 60

Pro Asp Arg Phe Thr Gly Ser Gly Ser Gly Thr Asp Phe Thr Leu Thr
65 70 75 80

Ile Ser Asn Val His Ala Glu Asp Leu Gly Val Tyr Phe Cys Gln His
85 90 95

Asn His Gly Ser Phe Leu Pro Tyr Thr Phe Gly Gly Gly Thr Lys Leu
100 105 110

Glu Ile Lys
115

<210> SEQ ID NO 106
<211> LENGTH: 107
<212> TYPE: PRT
<213> ORGANISM: Artificial sequence
<220> FEATURE:
<223> OTHER INFORMATION: VL of anti-PD-L1

<400> SEQUENCE: 106

Ser Ile Val Met Thr Gln Thr Pro Lys Phe Leu Pro Val Thr Ala Glu
1 5 10 15

Asp Arg Val Thr Ile Thr Cys Lys Ala Ser Gln Ser Val Ser Asn Glu
20 25 30

Val Ala Trp Tyr Gln Gln Lys Pro Gly Gln Ser Pro Lys Leu Leu Ile
35 40 45

Tyr Ser Ala Ser Ser Arg Tyr Thr Gly Val Pro Asp Arg Phe Ile Gly
50 55 60

Gly Gly Ser Ala Thr Asp Phe Thr Phe Thr Ile Ser Ser Val Gln Val
65 70 75 80

Glu Asp Leu Ala Val Tyr Phe Cys Gln Gln His Tyr Ser Ser Pro Leu
85 90 95

Thr Phe Gly Ala Gly Thr Lys Leu Glu Leu Lys
100 105

<210> SEQ ID NO 107
<211> LENGTH: 99
<212> TYPE: PRT
<213> ORGANISM: Artificial sequence
<220> FEATURE:
<223> OTHER INFORMATION: Human antibody germline gene M99683 IGHV4-31x02

<400> SEQUENCE: 107

Gln Val Gln Leu Gln Glu Ser Gly Pro Gly Leu Val Lys Pro Ser Gln
1 5 10 15

Thr Leu Ser Leu Thr Cys Thr Val Ser Gly Gly Ser Ile Ser Ser Gly
20 25 30

Gly Tyr Tyr Trp Ser Trp Ile Arg Gln His Pro Gly Lys Gly Leu Glu
35 40 45

Trp Ile Gly Tyr Ile Tyr Tyr Ser Gly Ser Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg

<210> SEQ ID NO 108
<211> LENGTH: 98
<212> TYPE: PRT
<213> ORGANISM: Artificial sequence
<220> FEATURE:
<223> OTHER INFORMATION: Human antibody germline gene X62109 IGHV1-3x01

<400> SEQUENCE: 108

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Ala Met His Trp Val Arg Gln Ala Pro Gly Gln Arg Leu Glu Trp Met
35 40 45

Gly Trp Ile Asn Ala Gly Asn Gly Asn Thr Lys Tyr Ser Gln Lys Phe
50 55 60

Gln Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg

<210> SEQ ID NO 109
<211> LENGTH: 101
<212> TYPE: PRT
<213> ORGANISM: Artificial sequence
<220> FEATURE:
<223> OTHER INFORMATION: Human antibody germline gene Z00023 IGKV4-1x01

<400> SEQUENCE: 109

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Val Leu Tyr Ser
20 25 30

Ser Asn Asn Lys Asn Tyr Leu Ala Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Tyr Ser Thr Pro
100

<210> SEQ ID NO 110
<211> LENGTH: 118
<212> TYPE: PRT
<213> ORGANISM: Artificial sequence
<220> FEATURE:
<223> OTHER INFORMATION: VH of anti-PD-L1

<400> SEQUENCE: 110

Gln Val Gln Leu Gln Glu Ser Gly Pro Gly Leu Val Lys Pro Ser Gln
1 5 10 15

Thr Leu Ser Leu Thr Cys Thr Val Ser Gly Asp Ser Ile Thr Ser Gly
20 25 30

Tyr Trp Asn Trp Ile Arg Gln His Pro Gly Lys Gly Leu Glu Trp Ile
35 40 45

Gly Tyr Ile Ser Tyr Thr Gly Ser Thr Tyr Tyr Asn Leu Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Tyr Ile Leu Trp Leu Arg His Phe Asp Tyr Trp Gly Gln Gly Thr
100 105 110

Leu Val Thr Val Ser Ser
115

<210> SEQ ID NO 111
<211> LENGTH: 118
<212> TYPE: PRT
<213> ORGANISM: Artificial sequence
<220> FEATURE:
<223> OTHER INFORMATION: VH of anti-PD-L1

<400> SEQUENCE: 111

Gln Val Gln Leu Gln Glu Ser Gly Pro Gly Leu Val Lys Pro Ser Gln
1 5 10 15

Thr Leu Ser Leu Thr Cys Thr Val Ser Gly Asp Ser Ile Thr Ser Gly
20 25 30

Tyr Trp Asn Trp Ile Arg Gln His Pro Gly Lys Gly Leu Glu Tyr Ile
35 40 45

Gly Tyr Ile Ser Tyr Thr Gly Ser Thr Tyr Tyr Asn Leu Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala

```
                85                  90                  95

Arg Tyr Ile Leu Trp Leu Arg His Phe Asp Tyr Trp Gly Gln Gly Thr
            100                 105                 110

Leu Val Thr Val Ser Ser
        115


<210> SEQ ID NO 112
<211> LENGTH: 118
<212> TYPE: PRT
<213> ORGANISM: Artificial sequence
<220> FEATURE:
<223> OTHER INFORMATION: VH of anti-PD-L1

<400> SEQUENCE: 112

Gln Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Ile Thr Ser Gly
            20                  25                  30

Tyr Trp Asn Trp Ile Arg Gln His Pro Gly Lys Gly Leu Glu Tyr Ile
        35                  40                  45

Gly Tyr Ile Ser Tyr Thr Gly Ser Thr Tyr Tyr Asn Leu Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Tyr Ile Leu Trp Leu Arg His Phe Asp Tyr Trp Gly Gln Gly Thr
            100                 105                 110

Leu Val Thr Val Ser Ser
        115


<210> SEQ ID NO 113
<211> LENGTH: 118
<212> TYPE: PRT
<213> ORGANISM: Artificial sequence
<220> FEATURE:
<223> OTHER INFORMATION: VH of anti-PD-L1

<400> SEQUENCE: 113

Gln Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Ile Thr Ser Gly
            20                  25                  30

Tyr Trp Asn Trp Ile Arg Gln His Pro Gly Lys Gly Leu Glu Tyr Ile
        35                  40                  45

Gly Tyr Ile Ser Tyr Thr Gly Ser Thr Tyr Tyr Asn Leu Ser Leu Lys
    50                  55                  60

Ser Arg Ile Thr Ile Ser Arg Asp Thr Ser Lys Asn Gln Tyr Ser Leu
65                  70                  75                  80

Lys Leu Ser Ser Val Thr Ala Ala Asp Thr Ala Val Tyr Tyr Cys Ala
                85                  90                  95

Arg Tyr Ile Leu Trp Leu Arg His Phe Asp Tyr Trp Gly Gln Gly Thr
            100                 105                 110

Leu Val Thr Val Ser Ser
        115


<210> SEQ ID NO 114
<211> LENGTH: 118
```

<212> TYPE: PRT
<213> ORGANISM: Artificial sequence
<220> FEATURE:
<223> OTHER INFORMATION: VH of anti-PD-L1

<400> SEQUENCE: 114

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Ile Thr Ser Gly
            20                  25                  30

Tyr Trp Asn Trp Ile Arg Gln His Pro Gly Lys Gly Leu Glu Tyr Met
        35                  40                  45

Gly Tyr Ile Ser Tyr Thr Gly Ser Thr Tyr Tyr Asn Leu Ser Leu Lys
    50                  55                  60

Ser Arg Ile Thr Ile Ser Arg Asp Thr Ser Lys Asn Gln Tyr Ser Leu
65                  70                  75                  80

Lys Leu Ser Ser Val Thr Ala Ala Asp Thr Ala Val Tyr Tyr Cys Ala
                85                  90                  95

Arg Tyr Ile Leu Trp Leu Arg His Phe Asp Tyr Trp Gly Gln Gly Thr
            100                 105                 110

Leu Leu Thr Val Ser Ser
        115
```

<210> SEQ ID NO 115
<211> LENGTH: 113
<212> TYPE: PRT
<213> ORGANISM: Artificial sequence
<220> FEATURE:
<223> OTHER INFORMATION: VL of anti-PD-L1

<400> SEQUENCE: 115

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Ser Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Gly Tyr Pro Leu Thr Phe Gly Gly Gly Thr Lys Leu Glu Ile
            100                 105                 110

Lys
```

<210> SEQ ID NO 116
<211> LENGTH: 113
<212> TYPE: PRT
<213> ORGANISM: Artificial sequence
<220> FEATURE:
<223> OTHER INFORMATION: VL of anti-PD-L1

<400> SEQUENCE: 116

```
Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Tyr Ser
            20                  25                  30
```

```
Ser Asn Gln Lys Asn Ser Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Gly Tyr Pro Leu Thr Phe Gly Gly Gly Thr Lys Leu Glu Ile
            100                 105                 110

Lys


<210> SEQ ID NO 117
<211> LENGTH: 113
<212> TYPE: PRT
<213> ORGANISM: Artificial sequence
<220> FEATURE:
<223> OTHER INFORMATION: VL of anti-PD-L1

<400> SEQUENCE: 117

Asp Ile Val Met Thr Gln Ser Pro Asp Ser Leu Ala Val Ser Leu Gly
1               5                   10                  15

Glu Arg Val Thr Ile Ser Cys Lys Ser Ser Gln Ser Leu Leu Tyr Ser
            20                  25                  30

Ser Asn Gln Lys Asn Ser Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Gly Tyr Pro Leu Thr Phe Gly Gly Gly Thr Lys Leu Glu Ile
            100                 105                 110

Lys


<210> SEQ ID NO 118
<211> LENGTH: 113
<212> TYPE: PRT
<213> ORGANISM: Artificial sequence
<220> FEATURE:
<223> OTHER INFORMATION: VL of anti-PD-L1

<400> SEQUENCE: 118

Asp Ile Val Met Thr Gln Ser Pro Asp Ser Leu Ala Val Ser Leu Gly
1               5                   10                  15

Glu Arg Val Thr Met Ser Cys Lys Ser Ser Gln Ser Leu Leu Tyr Ser
            20                  25                  30

Ser Asn Gln Lys Asn Ser Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95
```

Tyr Tyr Gly Tyr Pro Leu Thr Phe Gly Gly Gly Thr Lys Leu Glu Ile
100 105 110

Lys

<210> SEQ ID NO 119
<211> LENGTH: 114
<212> TYPE: PRT
<213> ORGANISM: Artificial sequence
<220> FEATURE:
<223> OTHER INFORMATION: VH of anti-PD-L1

<400> SEQUENCE: 119

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Arg Asn
20 25 30

Thr Met His Trp Val Arg Gln Ala Pro Gly Gln Arg Leu Glu Trp Met
35 40 45

Gly Phe Ile Asp Pro His Asn Thr Tyr Thr Arg Tyr Asn Gln Lys Phe
50 55 60

Lys Asp Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Trp Pro Met Asp Tyr Trp Gly Gln Gly Thr Leu Val Thr Val
100 105 110

Ser Ser

<210> SEQ ID NO 120
<211> LENGTH: 114
<212> TYPE: PRT
<213> ORGANISM: Artificial sequence
<220> FEATURE:
<223> OTHER INFORMATION: VH of anti-PD-L1

<400> SEQUENCE: 120

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Arg Asn
20 25 30

Thr Met His Trp Val Arg Gln Ala Pro Gly Gln Arg Leu Glu Trp Met
35 40 45

Gly Phe Ile Asp Pro His Asn Thr Tyr Thr Arg Tyr Asn Gln Lys Phe
50 55 60

Lys Asp Arg Val Thr Ile Thr Ala Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Trp Pro Met Asp Tyr Trp Gly Gln Gly Thr Leu Val Thr Val
100 105 110

Ser Ser

<210> SEQ ID NO 121
<211> LENGTH: 114
<212> TYPE: PRT
<213> ORGANISM: Artificial sequence
<220> FEATURE:
<223> OTHER INFORMATION: VH of anti-PD-L1

<400> SEQUENCE: 121

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Asn
            20                  25                  30

Thr Met His Trp Ile Arg Gln Ala Pro Gly Gln Arg Leu Glu Trp Met
        35                  40                  45

Gly Phe Ile Asp Pro His Asn Thr Tyr Thr Arg Tyr Asn Gln Lys Phe
    50                  55                  60

Lys Asp Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Pro Met Asp Tyr Trp Gly Gln Gly Thr Leu Val Thr Val
            100                 105                 110

Ser Ser
```

<210> SEQ ID NO 122
<211> LENGTH: 114
<212> TYPE: PRT
<213> ORGANISM: Artificial sequence
<220> FEATURE:
<223> OTHER INFORMATION: VH of anti-PD-L1

<400> SEQUENCE: 122

```
Gln Val Gln Leu Val Gln Ser Gly Ala Glu Val Ala Lys Pro Gly Ala
1               5                   10                  15

Ser Val Lys Val Ser Cys Lys Ala Ser Gly Tyr Thr Phe Thr Arg Asn
            20                  25                  30

Thr Met His Trp Ile Arg Gln Ala Pro Gly Gln Arg Leu Glu Trp Ile
        35                  40                  45

Gly Phe Ile Asp Pro His Asn Thr Tyr Thr Arg Tyr Asn Gln Lys Phe
    50                  55                  60

Lys Asp Arg Ala Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Pro Met Asp Tyr Trp Gly Gln Gly Thr Leu Val Thr Val
            100                 105                 110

Ser Ser
```

<210> SEQ ID NO 123
<211> LENGTH: 114
<212> TYPE: PRT
<213> ORGANISM: Artificial sequence
<220> FEATURE:
<223> OTHER INFORMATION: VH of anti-PD-L1

<400> SEQUENCE: 123

```
Gln Val Gln Leu Val Gln Ser Gly Ala Glu Val Ala Lys Pro Gly Ala
1               5                   10                  15

Ser Val Lys Met Ser Cys Lys Ala Ser Gly Tyr Thr Phe Thr Arg Asn
            20                  25                  30

Thr Met His Trp Ile Lys Gln Ala Pro Gly Gln Arg Leu Glu Trp Ile
        35                  40                  45

Gly Phe Ile Asp Pro His Asn Thr Tyr Thr Arg Tyr Asn Gln Lys Phe
    50                  55                  60
```

```
Lys Asp Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Pro Met Asp Tyr Trp Gly Gln Gly Thr Leu Val Thr Val
            100                 105                 110

Ser Ser


<210> SEQ ID NO 124
<211> LENGTH: 115
<212> TYPE: PRT
<213> ORGANISM: Artificial sequence
<220> FEATURE:
<223> OTHER INFORMATION: VL of anti-PD-L1

<400> SEQUENCE: 124

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Ser Trp Ser
            20                  25                  30

Glu Asn Gln Asn Asn Tyr Leu Ser Trp Tyr Gln Gln Lys Pro Gly Gln
        35                  40                  45

Pro Pro Lys Leu Leu Ile Tyr Gly Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln His
                85                  90                  95

Asn His Gly Ser Phe Leu Pro Tyr Thr Phe Gly Gln Gly Thr Lys Leu
            100                 105                 110

Glu Ile Lys
        115


<210> SEQ ID NO 125
<211> LENGTH: 115
<212> TYPE: PRT
<213> ORGANISM: Artificial sequence
<220> FEATURE:
<223> OTHER INFORMATION: VL of anti-PD-L1

<400> SEQUENCE: 125

Asp Ile Val Met Thr Gln Ser Pro Asp Ser Leu Ala Val Ser Leu Gly
1               5                   10                  15

Glu Arg Val Thr Ile Asn Cys Lys Ser Ser Gln Ser Leu Ser Trp Ser
            20                  25                  30

Glu Asn Gln Asn Asn Tyr Leu Ser Trp Tyr Gln Gln Lys Pro Gly Gln
        35                  40                  45

Pro Pro Lys Leu Leu Ile Tyr Gly Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Gly Val Tyr Tyr Cys Gln His
                85                  90                  95

Asn His Gly Ser Phe Leu Pro Tyr Thr Phe Gly Gln Gly Thr Lys Leu
            100                 105                 110

Glu Ile Lys
        115
```

<210> SEQ ID NO 126
<211> LENGTH: 115
<212> TYPE: PRT
<213> ORGANISM: Artificial sequence
<220> FEATURE:
<223> OTHER INFORMATION: VL of anti-PD-L1

<400> SEQUENCE: 126

Asp Ile Val Met Thr Gln Ser Pro Asp Ser Leu Ala Val Ser Leu Gly
1 5 10 15

Glu Arg Val Thr Met Arg Cys Lys Ser Ser Gln Ser Leu Ser Trp Ser
20 25 30

Glu Asn Gln Asn Asn Tyr Leu Ser Trp Tyr Gln Gln Lys Pro Gly Gln
35 40 45

Pro Pro Lys Leu Leu Ile Tyr Gly Ala Ser Ile Arg Glu Ser Gly Val
50 55 60

Pro Asp Arg Phe Ser Gly Ser Gly Ser Gly Thr Asp Phe Thr Leu Thr
65 70 75 80

Ile Ser Ser Val Gln Ala Glu Asp Val Gly Val Tyr Tyr Cys Gln His
85 90 95

Asn His Gly Ser Phe Leu Pro Tyr Thr Phe Gly Gln Gly Thr Lys Leu
100 105 110

Glu Ile Lys
115

<210> SEQ ID NO 127
<211> LENGTH: 354
<212> TYPE: DNA
<213> ORGANISM: Artificial sequence
<220> FEATURE:
<223> OTHER INFORMATION: Nucleotide sequence encoding VH of anti-PD-L1

<400> SEQUENCE: 127
caggttcagc tgcaggagtc cggccctggc ctggtgaagc ccagccagac cctgagcctg 60
acctgtaccg tgagcggcga cagcatcact agcggctact ggaactggat caggcaacac 120
cccggcaagg gcctggagta catcggctac atcagctaca ccggcagcac ctactacaac 180
ctgagtctga agagcagggt gaccatcagc cgggacacca gcaagaacca gttctctctg 240
aagctgagca gcgtgactgc ggcggatacc gccgtgtact actgcgccag gtacatcctg 300
tggttgaggc acttcgacta ctggggccag ggcaccctgg tgaccgttag ctct 354

<210> SEQ ID NO 128
<211> LENGTH: 342
<212> TYPE: DNA
<213> ORGANISM: Artificial sequence
<220> FEATURE:
<223> OTHER INFORMATION: Nucleotide sequence encoding VH of anti-PD-L1

<400> SEQUENCE: 128
caggtgcagc tggtgcagag cggagctgag gtggccaagc caggcgccag cgtgaagatg 60
tcctgcaagg ccagcggcta cacctttacc cggaacacaa tgcactggat taagcaggcc 120
cccggccagc ggctggagtg gatcggcttc atcgacccac acaataccta caccagatac 180
aaccagaagt ttaaggaccg ggccaccctg accgccgata catcagcatc aacagcttac 240
atggagctga gtagtctgag atctgaggat acagccgtgt actattgcgc tagatggcct 300
atggattact ggggccaggg aaccctggtg accgtgtcta gc 342

<210> SEQ ID NO 129
<211> LENGTH: 339
<212> TYPE: DNA
<213> ORGANISM: Artificial sequence
<220> FEATURE:
<223> OTHER INFORMATION: Nucleotide sequence encoding VL of anti-PD-L1

<400> SEQUENCE: 129
gacatcgtga tgacccagag ccccgactcc ctggccgtga gcctgggcga gagggccacc 60
atctcctgca agagcagtca gagccttctg tatagctcca accagaagaa cagcctggcc 120
tggtatcaac agaagcccgg tcaacccccc aagctgctga tctactgggc ctcaaccagg 180
gaaagcggcg tgcccgacag gttcagcggc agtggcagcg gcaccgactt caccctgacc 240
atcagctcct tgcaggccga ggacgtggca gtgtactact gccagcagta ctacggctac 300
cccctgacat tcggaggggg aaccaagttg gagatcaag 339

<210> SEQ ID NO 130
<211> LENGTH: 345
<212> TYPE: DNA
<213> ORGANISM: Artificial sequence
<220> FEATURE:
<223> OTHER INFORMATION: Nucleotide sequence encoding VL of anti-PD-L1

<400> SEQUENCE: 130
gatatcgtga tgacccagag cccagatagc ctggccgtga gcctgggaga gagagtgacc 60
atgagatgta agtctagtca gagtctgagt tggagcgaga atcagaacaa ttacctgagc 120
tggtatcagc agaagcctgg ccagcctcca aagctgctga tctacggcgc ctccatccgg 180
gagagcggag tgcccgaccg cttcagcggc agcggcagcg gcacagactt caccctgacc 240
atcagcagcg tgcaggccga ggatgtgggc gtgtactact gtcagcacaa ccacggcagc 300
ttcctgccct acaccttcgg gcagggcacc aagctggaga tcaag 345

<210> SEQ ID NO 131
<211> LENGTH: 107
<212> TYPE: PRT
<213> ORGANISM: Artificial sequence
<220> FEATURE:
<223> OTHER INFORMATION: Constant region

<400> SEQUENCE: 131

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 132
<211> LENGTH: 327
<212> TYPE: PRT

```
<213> ORGANISM: Artificial sequence
<220> FEATURE:
<223> OTHER INFORMATION: IgG4 heavy chain constant region

<400> SEQUENCE: 132

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Cys Gln Glu Glu Met Thr Lys
225                 230                 235                 240

Asn Gln Val Ser Leu Trp Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 133
<211> LENGTH: 327
<212> TYPE: PRT
<213> ORGANISM: Artificial sequence
<220> FEATURE:
<223> OTHER INFORMATION: IgG4 heavy chain constant region

<400> SEQUENCE: 133
```

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Cys Thr Leu Pro Pro Ser Gln Glu Glu Met Thr Lys
225                 230                 235                 240

Asn Gln Val Ser Leu Ser Cys Ala Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Val Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 134
<211> LENGTH: 220
<212> TYPE: PRT
<213> ORGANISM: Artificial sequence
<220> FEATURE:
<223> OTHER INFORMATION: Human PD-L1 extracellular region

<400> SEQUENCE: 134

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30
```

-continued

```
Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg
    210                 215                 220
```